United States Patent
Cogan et al.

(10) Patent No.: US 8,609,696 B2
(45) Date of Patent: Dec. 17, 2013

(54) SEROTONIN 5-HT2B RECEPTOR INHIBITORS

(75) Inventors: Derek Cogan, Sandy Hook, CT (US); Neil Moss, Ridgefield, CT (US); Christopher Ronald Sarko, New Milford, CT (US); Samantha Jayne Bamford, Didcot (GB); Pui Leng Loke, Abingdon (GB); Heather Tye, East Hagbourne (GB); Mark Whittaker, Abingdon (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 129 days.

(21) Appl. No.: 13/139,363

(22) PCT Filed: Dec. 14, 2009

(86) PCT No.: PCT/US2009/067865
§ 371 (c)(1), (2), (4) Date: Jul. 11, 2011

(87) PCT Pub. No.: WO2010/080357
PCT Pub. Date: Jul. 15, 2010

(65) Prior Publication Data
US 2011/0269742 A1    Nov. 3, 2011

Related U.S. Application Data

(60) Provisional application No. 61/138,670, filed on Dec. 18, 2008.

(51) Int. Cl.
*A61K 31/445*    (2006.01)
*C07D 401/04*    (2006.01)

(52) U.S. Cl.
USPC .......................................... 514/322; 546/199

(58) Field of Classification Search
USPC .......................................... 514/322; 546/199
See application file for complete search history.

(56) References Cited

U.S. PATENT DOCUMENTS 5,434,169 A * 7/1995 Jegham et al. ................. 514/322
7,211,601 B2 * 5/2007 Halazy et ...................... 514/423
7,999,006 B2 * 8/2011 Lamb .............................. 514/477
2008/0166359 A1 * 7/2008 Lamb ............................ 424/158.1
2011/0269742 A1 11/2011 Cogan et al.

FOREIGN PATENT DOCUMENTS

| EP | 0591027 A1 | 4/1994 |
|---|---|---|
| WO | 03002559 A2 | 1/2003 |
| WO | 03002561 A1 | 1/2003 |
| WO | 03037274 A2 | 5/2003 |
| WO | 2005044797 A1 | 5/2005 |
| WO | 2006044509 A2 | 4/2006 |
| WO | 2008076415 A1 | 6/2008 |

OTHER PUBLICATIONS

Chem Spider ID 23337737, 23337733, 23337213, 23337698 (2013).*
Moss et al. "A new class of . . . " Bioorg. Med. Chem. Lett. v.19, p. 2206-2210 (2009).*
Improper Markush "supplemental examination guidelines" p. 1, 64-67 (2011).*
Silverman "Organ chem. drug design . . . " p. 65-73 (1993).*
Chemlin catalog containing KB546429) p. 1 (2013).*
SureChem p. 1 (2013).*
Chem Abstracts—Accession No. 2042667623 and Acession No. 2042698610. Catalog: Ryan Scientific Screening Library, 2008.
International Search Report and Written Opinion for PCT/US2009/067865 mailed Apr. 19, 2010.
Moss, N. et al. "A new class of 5-HT2B antagonists possesses favorable potency, selectivity, and rat pharmacokinetic properties," Bioorganic & Medicinal Chemistry Letters, Pergamon, Elsevier Science, GB, vol. 19, No. 8, 2009, pp. 2206-2210.

* cited by examiner

*Primary Examiner* — Celia Chang
(74) *Attorney, Agent, or Firm* — Michael P. Morris; Anthony P. Bottino

(57) ABSTRACT

Disclosed are Serotonin 5-HT2B receptor inhibitors of the formula I. Also disclosed are methods of making and methods of using these compounds.

(I)

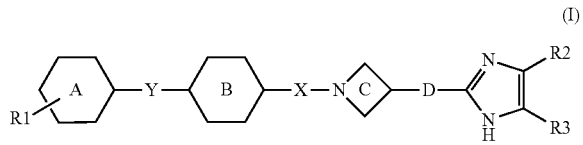

5 Claims, No Drawings

SEROTONIN 5-HT2B RECEPTOR INHIBITORS

APPLICATION DATA

This application claims benefit to U.S. provisional application Ser. No. 61/138,670 filed Dec. 18, 2008.

BACKGROUND OF THE INVENTION

1. Technical Field

This invention relates to compounds which are active against the serotonin 5-HT$_{2B}$ receptor. They may be used to treat diseases characterized by dysfunctional or overly active 5-HT$_{2B}$ receptors.

2. Background Information

The serotonin 5-HT$_{2B}$ receptor was first characterized as the serotonogenic GPCR that controlled contraction in the rat stomach fundus (Clineschmidt, et al., 1985, *J. Pharmacol. Exp. Ther.*, 235, 696). 5-HT$_{2B}$ has since been detected in human tissues including adipose tissue, central nervous system (CNS), heart, intestine, liver, lung, ovary, pancreas, prostate, salivary gland, skeletal muscle, spleen, testis, thymus, thyroid, trachea, uterus, and vasculature (Kursar et al., 1994, *Mol. Pharmacol.*, 46, 227; Sanden et al., 2000, *Neurochem Int.*, 36, 427-435; Borman et al., 2002 *Br. J. Pharmacol.*, 135, 1144; Schmuck et al., 1994, *FEBS Lett.*, 342, 85). Modulators of 5-HT$_{2B}$, which include antagonists, partial antagonists, inverse agonists, and 5-HT$_{2B}$ desensitizers, may be used as treatments for disorders in these tissues in which activation of 5-HT$_{2B}$ has a direct or indirect role.

Control of serotonin (5-HT) levels and signaling is used to treat disorders of the central nervous system. These diseases include alcoholism and other addiction disorders, anxiety, bipolar disorder, concentration and memory disorders, depression, eating disorders, obsessive compulsive disorder, panic disorders, prostate hyperplasia, schizophrenia, sexual dysfunction, sleep disorders, and social phobia. Antagonists of 5-HT$_{2B}$ may have a role in treating these diseases of the central nervous system by mitigating effects of 5-HT.

A selective antagonist of 5-HT$_{2B}$ increases wakefulness and motor activity in rats (Kantor et al., 2004, *Br. J. Pharmacol.*, 132, 1332). Thus 5-HT2B antagonists may treat sleep disorders such as narcolepsy, or be used to treat fatigue, lethargy, or poor concentration.

Modulation of 5-HT$_{2B}$ may control overeating. While the selective 5-HT$_{2B}$ agonist BW723C86 stimulates hyperphagia in rats, the 5-HT$_{2B/2C}$ antagonist SB206553 blocks the hyperphagic effect of BW723C86 (Kennett, 1997, *Neuropharmacology*, 36, 233). 5-HT also regulates both intestinal contraction and intestinal motility via regulation of proliferation of the interstitial cells of cajal (ICC). Antagonists of 5-HT$_{2B}$ block both the contractile response (Borman et al., 2002, *Br. J. Pharmacol.*, 135, 1144) and the proliferation of ICC that stimulate motility (Wouters et al., 2007, *Gastroenterology*, 133, 897). Therefore, 5-HT$_{2B}$ modulators may be used to treat gastric motility disorders such as irritable bowel syndrome.

5-HT has a role in vascular contraction and relaxation, and can impact vascular and function, growth, and morphology. Pulmonary arterial hypertension (PAH) is associated with abnormal vascular proliferation in the lung. PAH has an increased risk in patients exposed to a selective 5-HT$_{2B}$ agonist generated from the metabolism from dexfenfluramine. While wild-type mice develop symptoms of PAH under hypoxic conditions, 5-HT$_{2B}$ receptor knock-out mice do not. Moreover, the selective 5-HT$_{2B}$ antagonist RS127445 prevented the development of PAH symptoms in wild-type mice (Launay et al., 2002, *Nature Med.*, 1129; Esteve et al., 2007, *Cell Biochem. Biophys.*, 47, 33). This suggests modulation of 5-HT$_{2B}$ may be a treatment for PAH. Indeed, the selective 5-HT2B antagonist PRX-08066 has demonstrated primary efficacy in Phase IIa clinical trials for PAH in man (EPIX Pharmaceuticals Inc. Media Release, http://www.epixpharma.com).

Renal function is also dependent on the proper regulation of blood flow. The selective 5-HT$_{2B}$ agonist BW723C86 stimulates both an increase in renal nerve activity and decrease in renal blood pressure in rats. These effects are blocked by treatment with the 5-HT$_{2B/2C}$ antagonist SB204741 but not with a selective 5-HT$_{2C}$ antagonist (Knowles et al., 2000, *Br. J. Pharmacol.*, 129, 177). Therefore, modulation of 5-HT$_{2B}$ activity may treat diseases associated with renal hypotension such as acute renal failure.

Migraine headaches are associated with dysfunction of the meningeal blood flow and are associated with elevated 5-HT levels. Many treatments for migraine demonstrate affinity for multiple 5-HT receptors, including significant modulation of 5-HT$_{2B}$. Activation of 5-HT$_{2B}$ releases NO that is necessary for the genesis of migraine (Fozard et al., 1995, *Arch. Int. Pharmacodyn. Ther.*, 329, 111; Schmuck et al., 1996, *Eur. J. Neurosci.*, 8, 959). In a guinea pig model of migraine, the selective 5-HT$_{2B}$ antagonist LY202146 blocks mCPP induced dural plasma protein extravasation (Johnson et al., 2003, *Cephalagia*, 23, 117). In addition, the prophylactic migraine treatment dihydroergotamine modulates 5-HT2B activity by agonist-mediated desensitization via the metabolite 8'-hydroxy-dihydroergotamine (Schaerlinger et al., 2003, 140, 277).

Therefore, modulation of 5-HT2B may be a prophylactic treatment for migraine. Antagonism of 5-HT$_{2B}$ may additionally be used to treat hypertension. Rats treated with either deoxycorticosterone aceate-salt or N$^{\omega}$-nitro-L-arginine become hypertensive. Treatment of these hypertensive rats with the selective 5-HT$_{2B}$ antagonist LY272015 significantly reduces blood pressure. Moreover, the 5-HT$_{2B}$ protein levels are 2 to 3 fold higher in hypertensive rats than in the sham normotensive rats (Watts et al., 1999, *Am. J. Physio. Hear Circ. Physiol.*, 276, H944; Banes et al., 2002, *Hypertension*, 39, 394; Russell et al., 2002, *J. Pharmacol. Exp. Ther.*, 303, 179).

The phenotype of 5-HT$_{2B}$ receptor knock-out mice demonstrates the importance of this receptor for heart development. Surviving mice possess underdeveloped hearts resulting from impaired myocyte proliferation (Nebigil, et al., 2001, *Circulation*, 103, 2973). Conversely, 5-HT$_{2B}$ over expression in mice leads to cardiac hypertrophy (Nebigil, et al., 2003, *Circulation*, 107 (25), 3223). The selective antagonists of 5-HT$_{2B}$ SB206553 and SB215505 prevent isoproterenol induced cardiac hypertrophy (Jaffré et al., 2004, *Circulation*, 110, 969) Additionally, SB215505 was efficacious in a rat aortic banding model of cardiomyopathy (Liang et al., 2006, *Cardio. Res.*, 72, 303). More recently, genomics data from a model of tachypacing-induced decompensatory heart failure in dogs showed an upregulation of 5-HT$_{2B}$ mRNA (Ojaimi et al., 2007, *Physiol. Genomics* 29, 76). An upregulation of 5-HT$_{2B}$ mRNA has also been reported in humans with cardiomyopathies (Oxford et al., 2005, USPTO Application 20050176791). Therefore, modulation of 5-HT$_{2B}$ may treat disorders associated with cardiac hypertrophy such as congestive heart failure.

While compounds of this invention have not been exemplified in the chemical and patent literature, [4-(1H-benzimidazol-2-yl)-piperidin-1-yl]-biphenyl-4-yl-methanone is available for purchase from commercial vendors.

BRIEF SUMMARY OF THE INVENTION

It is therefore an object of the invention to provide compounds of the formula (I) as described herein below and compositions containing such compounds which are active against the serotonin 5-HT$_{2B}$ receptor.

It is a further object of the invention to provide methods using and methods of making compounds of the formula (I).

DETAILED DESCRIPTION OF THE INVENTION

In the broadest generic embodiment, there is provided a compound of the formula (I)

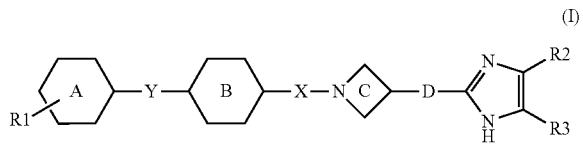

wherein:
Ring A is a 5-6 membered aryl or heteroaryl ring optionally each substituted by one to three $R^1$;
Ring B is aryl or a 5-6 membered heteroaryl ring each optionally substituted by one to three $R^1$;
Ring C is an azetidine, pyrrolidine or piperidine ring optionally substituted with $R^4$;
Y is a bond, $CH_2$, O, NH, or $S(O)_m$ wherein m is 0-2;
X is C=O or $SO_2$;
D is a bond or $C(R^6)_2$;
$R^1$ is independently halogen, CN, $C_{1-6}$alkyl, $C_{3-6}$ cycloalkyl $C_{1-6}$alkoxy, $C_{1-3}$alkoxy$C_{1-3}$alkoxy, hydroxy, oxo, substituted amino, $C_{1-6}$acylamino, $C_{1-6}$ acyl, —$CO_2H$, —$CO_2$ ($C_{1-6}$alkyl) or —$CO_2NR^7{}_2$;
$R^2$ and $R^3$ are independently $C_{1-6}$alkyl, hydrogen, halogen, CN, aryl, heteroaryl, $C_{1-6}$alkoxy, hydroxy, substituted amino, $C_{1-6}$acylamino, $C_{1-6}$ acyl, substituted carboxamido or $R^2$ and $R^3$ may be taken together to form a fused carbocyclic, heterocylic or heteroaryl ring further substituted with one or more $R^5$;
$R^4$ is halogen, hydroxy, $C_{1-4}$alkoxy or $C_{1-6}$alkyl;
$R^5$ is halogen, —$CO_2H$, —$CO_2(C_{1-6}$alkyl), —$CO_2NR_2$, hydroxy, $C_{1-6}$alkoxy, $C_{1-6}$alkyl, wherein 2 $R^5$'s may be taken together to form a carbocyclic, heterocylic or heteroaryl ring;
$R^6$ is hydrogen, halogen, hydroxy, $C_{1-4}$alkoxy or $C_{1-6}$alkyl wherein 2 $R^6$'s may be taken together to form a carbocyclic, heterocylic or heteroaryl ring;
$R^7$ is hydrogen, or $C_{1-6}$alkyl wherein two $R^7$'s may be taken together to form a 3-7 membered heterocycle.
wherein each $R^1$-$R^6$ is optionally partially or fully halogenated where possible;
or a pharmaceutically acceptable salt thereof;
with the proviso that [4-(1H-benzimidazol-2-yl)-piperidin-1-yl]-biphenyl-4-yl-methanone is excluded.

The compound of the formula (I) according to the embodiment immediately described above and wherein:
Ring A is phenyl, oxazolyl, isoxazolyl, oxadiazolyl, thiazolyl, pyrazolyl, pyrrolyl, imidazolyl, thienyl, thiadiazolyl, triazolyl, pyridinyl, pyrimidinyl, pyridazinyl, pyrazinyl or triazinyl each optionally substituted by one to two $R^1$;
Ring B is a phenyl, oxazolyl, isoxazolyl, oxadiazolyl, thiazolyl, pyrazolyl, pyrrolyl, imidazolyl, thienyl, thiadiazolyl, triazolyl, pyridinyl, pyrimidinyl, pyridazinyl, pyrazinyl or triazinyl each optionally substituted by one $R^1$;
Ring C is an azetidine, pyrrolidine or piperidine ring;
Y is a bond, $CH_2$, O, NH, or $SO_2$;
X is C=O or $SO_2$;
D is a bond or $C(R^6)_2$;
$R^1$ is independently halogen, $C_{1-3}$alkyl, —$OCF_3$, cyclopropyl, $C_{1-3}$alkoxy, $C_{1-3}$alkoxy$C_{1-3}$alkoxy, oxo or $C_{1-3}$acylamino;
$R^2$ and $R^3$ are independently $C_{1-6}$alkyl, $CF_3$, hydrogen, halogen, CN, aryl, heteroaryl, $C_{1-6}$alkoxy, hydroxy, substituted amino, $C_{1-6}$acylamino, $C_{1-6}$ acyl, substituted carboxamido or $R^2$ and $R^3$ may be taken together to form a fused benzo ring further substituted with one or more $R^5$;
$R^5$ is halogen, —$CO_2H$, —$CO_2(C_{1-6}$alkyl), —$CO_2NR_2$, hydroxy, $C_{1-6}$alkoxy or $C_{1-6}$alkyl;
$R^6$ is hydrogen, halogen, hydroxy, $C_{1-4}$alkoxy or $C_{1-6}$alkyl.

The compound of the formula (I) according to the embodiment immediately described above and wherein:
Ring A is phenyl, isoxazolyl, oxadiazolyl, pyrazolyl, thienyl, pyridinyl or pyrimidinyl, each optionally substituted by one to two $R^1$;
Ring B is a phenyl, isoxazolyl, oxadiazolyl, thiazolyl, pyrazolyl, thienyl, pyridinyl or pyrimidinyl, each optionally substituted by one $R^1$.

The compound of the formula (I) according to the embodiment immediately described above and wherein:
Ring A is phenyl, pyridine-2-yl, pyridine-3-yl, pyrimidin-2-yl, 2-thienyl, oxadiazol-3-yl, pyrazol-4-yl or isoxazol-4-yl each optionally substituted by one to two $R^1$;
Ring B is phenyl, pyridine-2-yl, pyridine-3-yl, pyridin-2(1H)-one, 2-thienyl, oxadiazol-3-yl, pyrazol-4-yl, 1,3-thiazol-2-yl or pyrimidin-5-yl each optionally substituted by one $R^1$;
$R^1$ is independently F, Cl, $C_{1-3}$alkyl, —$OCF_3$, cyclopropyl, $C_{1-3}$alkoxy, $C_{1-3}$alkoxy$C_{1-3}$alkoxy or $C_{1-3}$acylamino;
$R^2$ and $R^3$ are independently $C_{1-3}$alkyl, $CF_3$, hydrogen, halogen, CN or phenyl, or $R^2$ and $R^3$ may be taken together to form a fused benzo ring further substituted with one or more $R^5$;
$R^5$ is F, —$CO_2H$, —$CO_2(C_{1-6}$alkyl), —$CO_2NR_2$, hydroxy, $C_{1-6}$alkoxy or $C_{1-6}$alkyl.

In another embodiment, the invention provides compounds of the formula (I) in Table I which can be made in view of the general synthesis and examples provided herein, and materials and methods known in the art.

TABLE I

| # | Structure | Name |
|---|-----------|------|
| 1 | 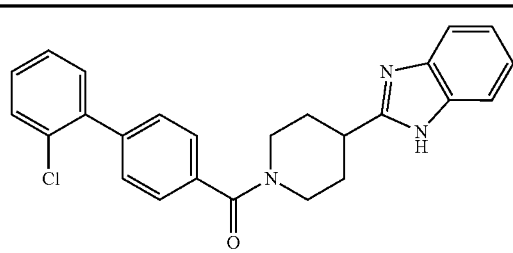 | [4-(1H-benzimidazol-2-yl)piperidin-1-yl](2'-chlorobiphenyl-4-yl)methanone |

TABLE I-continued

| # | Structure | Name |
|---|---|---|
| 2 | 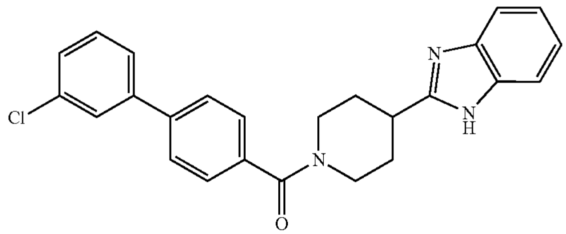 [SMILES: O=C(c1ccc(-c2cccc(Cl)c2)cc1)N1CCC(c2nc3ccccc3[nH]2)CC1] | [4-(1H-benzimidazol-2-yl)piperidin-1-yl](3'-chlorobiphenyl-4-yl)methanone |
| 3 | 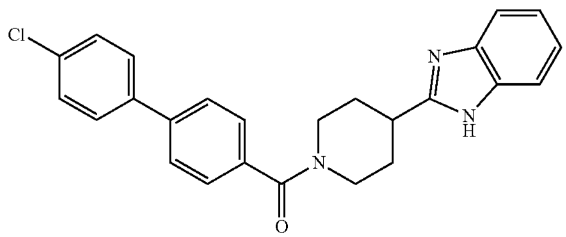 [SMILES: O=C(c1ccc(-c2ccc(Cl)cc2)cc1)N1CCC(c2nc3ccccc3[nH]2)CC1] | [4-(1H-benzimidazol-2-yl)piperidin-1-yl](4'-chlorobiphenyl-4-yl)methanone |
| 4 | 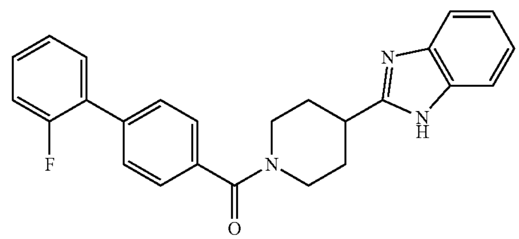 | [4-(1H-benzimidazol-2-yl)piperidin-1-yl](2'-fluorobiphenyl-4-yl)methanone |
| 5 | 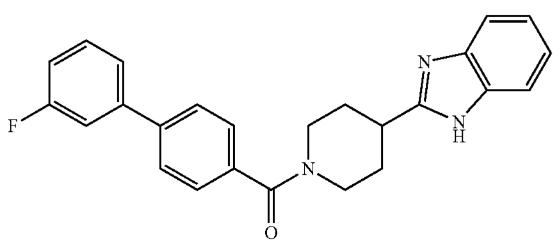 [SMILES: O=C(c1ccc(-c2cccc(F)c2)cc1)N1CCC(c2nc3ccccc3[nH]2)CC1] | [4-(1H-benzimidazol-2-yl)piperidin-1-yl](3'-fluorobiphenyl-4-yl)methanone |
| 6 | 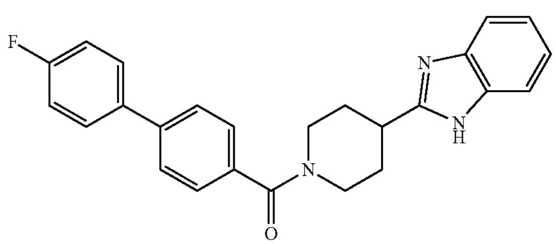 [SMILES: O=C(c1ccc(-c2ccc(F)cc2)cc1)N1CCC(c2nc3ccccc3[nH]2)CC1] | [4-(1H-benzimidazol-2 yl)piperidin-1-yl](4'-fluorobiphenyl-4-yl)methanone |
| 7 | 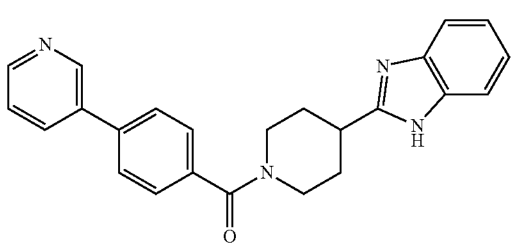 [SMILES: O=C(c1ccc(-c2cccnc2)cc1)N1CCC(c2nc3ccccc3[nH]2)CC1] | [4-(1H-benzimidazol-2-yl)piperidin-1-yl][4-(pyridin-3-yl)phenyl]methanone |

TABLE I-continued

| # | Structure | Name |
|---|---|---|
| 8 | 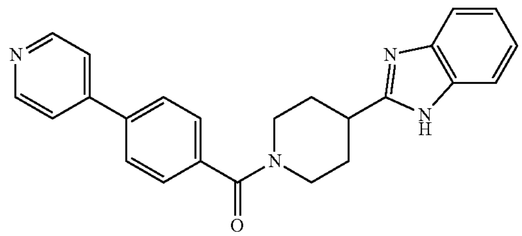 [SMILES: O=C(c1ccc(-c2ccncc2)cc1)N1CCC(c2nc3ccccc3[nH]2)CC1] | [4-(1H-benzimidazol-2-yl)piperidin-1-yl][4-(pyridin-4-yl)phenyl]methanone |
| 9 | 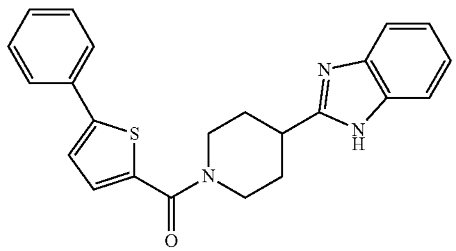 | [4-(1H-Benzimidazol-2-yl)piperidin-1-yl](5-phenyl-2-thienyl)methanone |
| 10 | 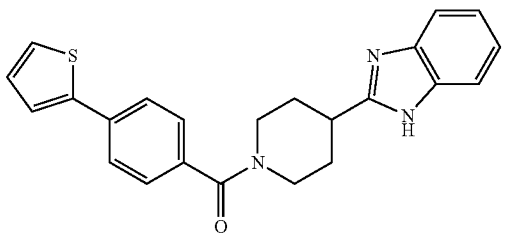 [SMILES: O=C(c1ccc(-c2cccs2)cc1)N1CCC(c2nc3ccccc3[nH]2)CC1] | [4-(1H-Benzimidazol-2-yl)piperidin-1-yl][4-(2-thienyl)phenyl]methanone |
| 11 | 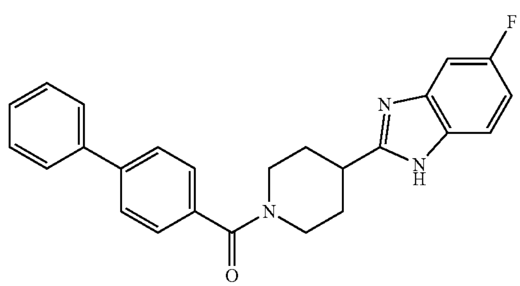 [SMILES: O=C(c1ccc(-c2ccccc2)cc1)N1CCC(c2nc3cc(F)ccc3[nH]2)CC1] | biphenyl-4-yl[4-(5-fluoro-1H-benzimidazol-2-yl)piperidin-1-yl]methanone |
| 12 | 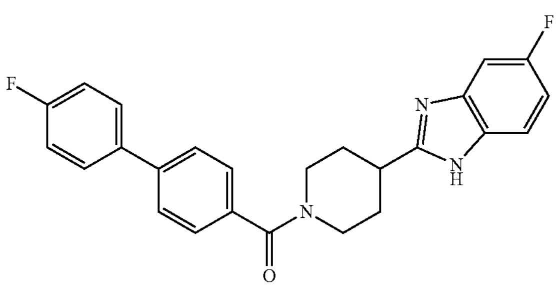 [SMILES: O=C(c1ccc(-c2ccc(F)cc2)cc1)N1CCC(c2nc3cc(F)ccc3[nH]2)CC1] | [4-(5-fluoro-1H-benzimidazol-2-yl)piperidin-1-yl](4'-fluorobiphenyl-4-yl)methanone |
| 13 | 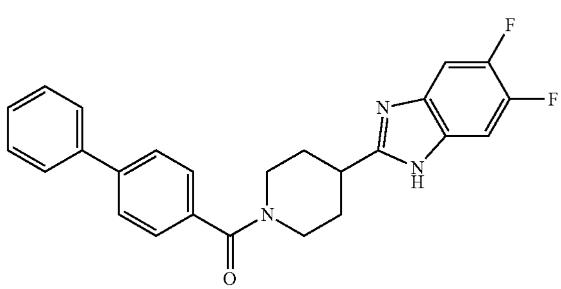 [SMILES: O=C(c1ccc(-c2ccccc2)cc1)N1CCC(c2nc3cc(F)c(F)cc3[nH]2)CC1] | biphenyl-4-yl[4-(5,6-difluoro-1H-benzimidazol-2-yl)piperidin-1-yl]methanone |

TABLE I-continued

| # | Structure | Name |
|---|---|---|
| 14 | 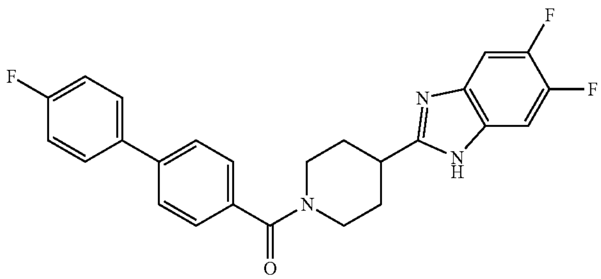 [SMILES: O=C(c1ccc(-c2ccc(F)cc2)cc1)N1CCC(c2nc3cc(F)c(F)cc3[nH]2)CC1] | [4-(5,6-difluoro-1H-benzimidazol-2-yl)piperidin-1-yl](4'-fluorohiphenyl-4-yl)methanone |
| 15 | 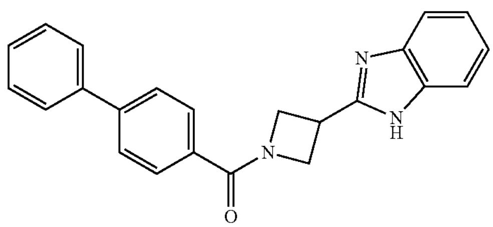 [SMILES: O=C(c1ccc(-c2ccccc2)cc1)N1CC(c2nc3ccccc3[nH]2)C1] | [3-(1H-benzimidazol-2-yl)azetidin-1-yl](biphenyl-4-yl)methanone |
| 16 | 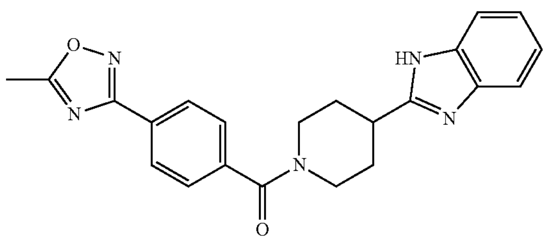 [SMILES: Cc1nc(-c2ccc(C(=O)N3CCC(c4nc5ccccc5[nH]4)CC3)cc2)no1] | [4-(1H-benzimidazol-2-yl)piperidin-1-yl][4-(5-methyl-1,2,4-oxadiazol-3-yl)phenyl]methanone |
| 17 | 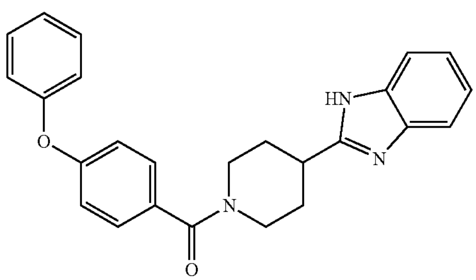 [SMILES: O=C(c1ccc(Oc2ccccc2)cc1)N1CCC(c2nc3ccccc3[nH]2)CC1] | [4-(1H-benzimidazol-2-yl)piperidin-1-yl](4-phenoxyphenyl)methanone |
| 18 | 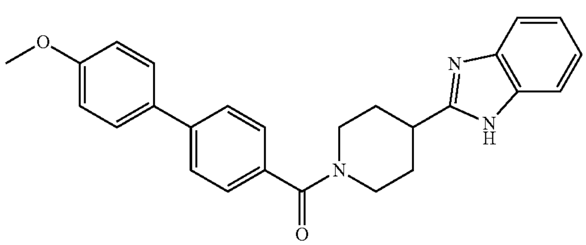 [SMILES: COc1ccc(-c2ccc(C(=O)N3CCC(c4nc5ccccc5[nH]4)CC3)cc2)cc1] | [4-(1H-benzimidazol-2-yl)piperidin-1-yl](4'-methoxybiphenyl-4-yl)methanone |
| 19 | 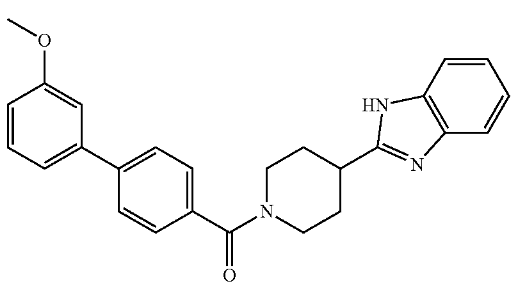 [SMILES: COc1cccc(-c2ccc(C(=O)N3CCC(c4nc5ccccc5[nH]4)CC3)cc2)c1] | [4-(1H-benzimidazol-2-yl)piperidin-1-yl](3'-methoxybiphenyl-4-yl)methanone |

TABLE I-continued

| # | Structure | Name |
|---|---|---|
| 20 | 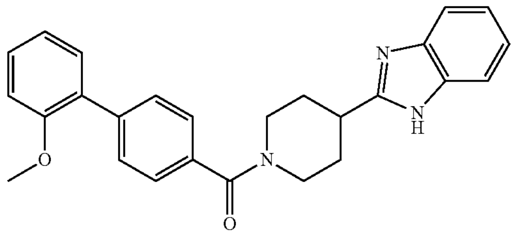 [SMILES: COc1ccccc1-c1ccc(C(=O)N2CCC(c3nc4ccccc4[nH]3)CC2)cc1] | [4-(1H-benzimidazol-2-yl)piperidin-1-yl](2'-methoxybiphenyl-4-yl)methanone |
| 21 | 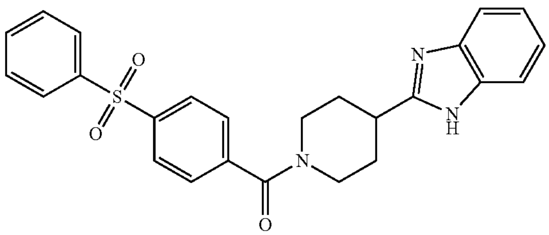 [SMILES: O=C(c1ccc(S(=O)(=O)c2ccccc2)cc1)N1CCC(c2nc3ccccc3[nH]2)CC1] | [4-(1H-benzimidazol-2-yl)piperidin-1-yl][4-(phenylsulfonyl)phenyl]methanone |
| 22 | 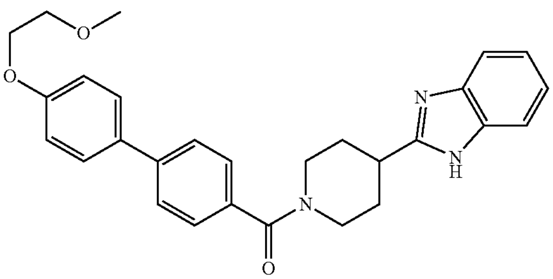 [SMILES: COCCOc1ccc(-c2ccc(C(=O)N3CCC(c4nc5ccccc5[nH]4)CC3)cc2)cc1] | [4-(1H-benzimidazol-2-yl)piperidin-1-yl][4'-(2-methoxyethoxy)biphenyl-4-yl]methanone |
| 23 | 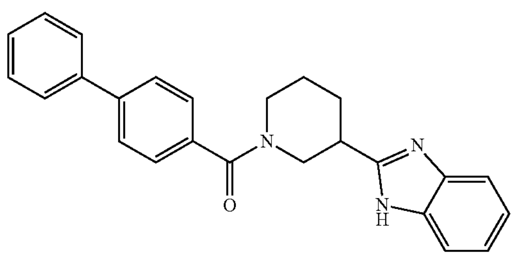 [SMILES: O=C(c1ccc(-c2ccccc2)cc1)N1CCCC(c2nc3ccccc3[nH]2)C1] | [3-(1H-benzimidazol-2-yl)piperidin-1-yl](biphenyl-4-yl)methanone |
| 24 | 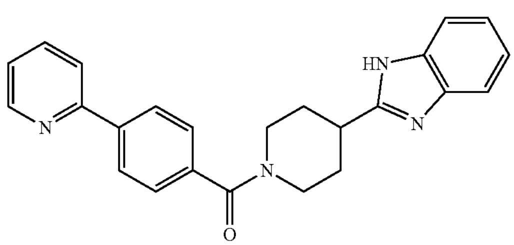 [SMILES: O=C(c1ccc(-c2ccccn2)cc1)N1CCC(c2nc3ccccc3[nH]2)CC1] | [4-(1H-benzimidazol-2-yl)piperidin-1-yl][4-(pyridin-2-yl)phenyl]methanone |
| 25 | 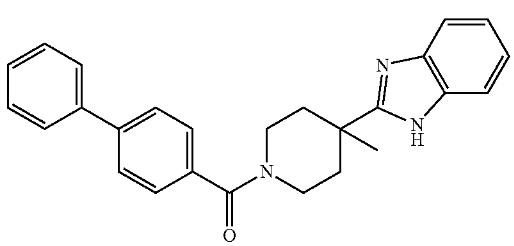 [SMILES: CC1(c2nc3ccccc3[nH]2)CCN(C(=O)c2ccc(-c3ccccc3)cc2)CC1] | [4-(1H-Benzimidazol-2-yl)-4-methylpiperidin-1-yl](biphenyl-4-yl)methanone |

TABLE I-continued

| # | Structure | Name |
|---|---|---|
| 26 | 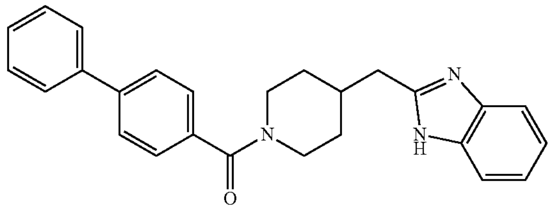 [SMILES: O=C(c1ccc(-c2ccccc2)cc1)N1CCC(Cc2nc3ccccc3[nH]2)CC1] | [4-(1H-benzimidazol-2-ylmethyl)piperidin-1-yl](biphenyl-4-yl)methanone |
| 27 | 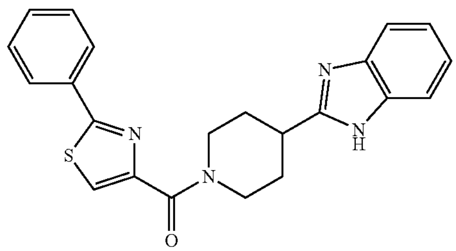 | [4-(1H-benzimidazol-2-yl)piperidin-1-yl](2-phenyl-1,3-thiazol-4-yl)methanone |
| 28 | 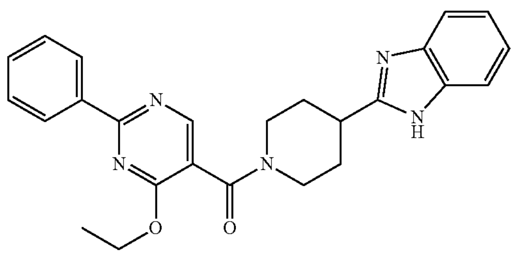 [SMILES: CCOc1nc(-c2ccccc2)ncc1C(=O)N1CCC(c2nc3ccccc3[nH]2)CC1] | [4-(1H-benzimidazol-2-yl)piperidin-1-yl](4-ethoxy-2-phenylpyrimidin-5-yl)methanone |
| 29 | 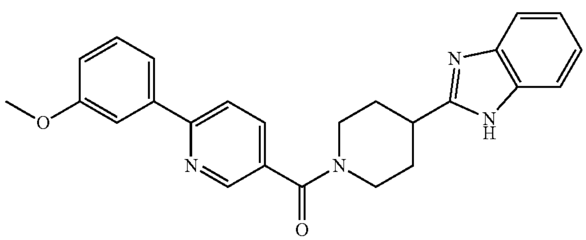 [SMILES: COc1cccc(-c2ccc(C(=O)N3CCC(c4nc5ccccc5[nH]4)CC3)cn2)c1] | [4-(1H-benzimidazol-2-yl)piperidin-1-yl][6-(3-methoxyphenyl)pyridin-3-yl]methanone |
| 30 | 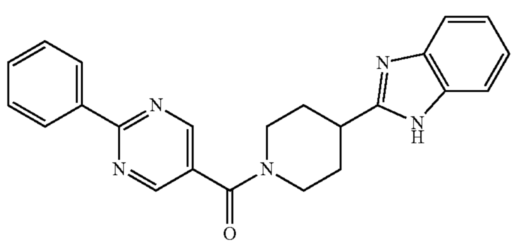 [SMILES: O=C(c1cnc(-c2ccccc2)nc1)N1CCC(c2nc3ccccc3[nH]2)CC1] | [4-(1H-benzimidazol-2-yl)piperidin-1-yl](2-phenylpyrimidin-5-yl)methanone |
| 31 | 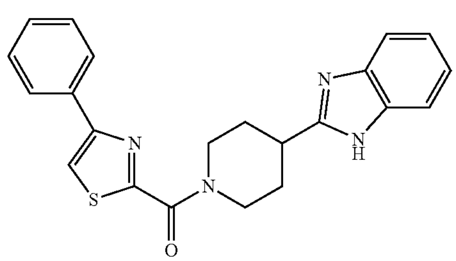 [SMILES: O=C(c1nc(-c2ccccc2)cs1)N1CCC(c2nc3ccccc3[nH]2)CC1] | [4-(1H-benzimidazol-2-yl)piperidin-1-yl](4-phenyl-1,3-thiazol-2-yl)methanone |

TABLE I-continued

| # | Structure | Name |
|---|---|---|
| 32 | 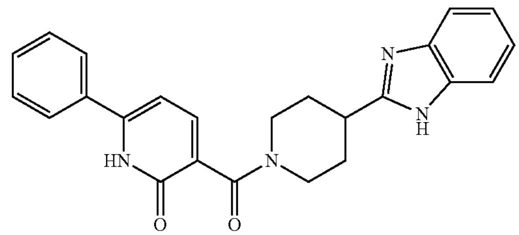 [SMILES: O=C(c1ccc(-c2ccccc2)[nH]c1=O)N1CCC(c2nc3ccccc3[nH]2)CC1] | 3-{[4-(1H-benzimidazol-2-yl)piperidin-1-yl]carbonyl}-6-phenylpyridin-2(1H)-one |
| 33 | 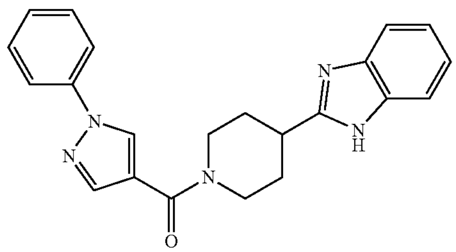 [SMILES: O=C(c1cnn(-c2ccccc2)c1)N1CCC(c2nc3ccccc3[nH]2)CC1] | [4-(1H-Benzimidazol-2-yl)piperidin-1-yl](1-phenyl-1H-pyrazol-4-yl)methanone |
| 34 | 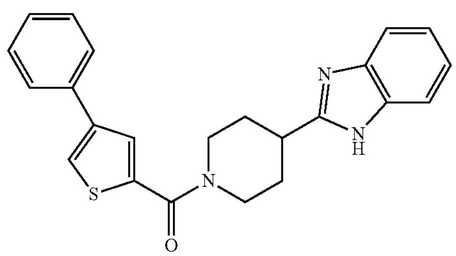 | [4-(1H-Benzimidazol-2-yl)piperidin-1-yl](4-phenyl-2-thienyl)methanone |
| 35 | 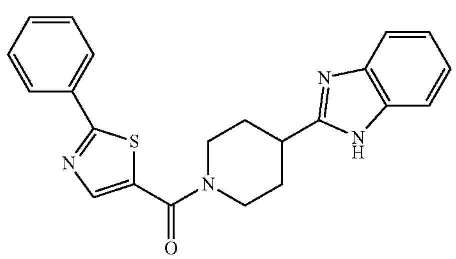 [SMILES: O=C(c1cnc(-c2ccccc2)s1)N1CCC(c2nc3ccccc3[nH]2)CC1] | [4-(1H-benzimidazol-2-yl)piperidin-1-yl](2-phenyl-1,3-thiazol-5-yl)methanone |
| 36 | 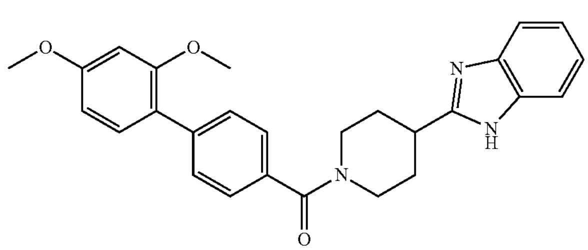 [SMILES: COc1ccc(-c2ccc(C(=O)N3CCC(c4nc5ccccc5[nH]4)CC3)cc2)c(OC)c1] | [4-(1H-benzimidazol-2-yl)piperidin-1-yl](2',4'-dimethoxybiphenyl-4-yl)methanone |
| 37 | 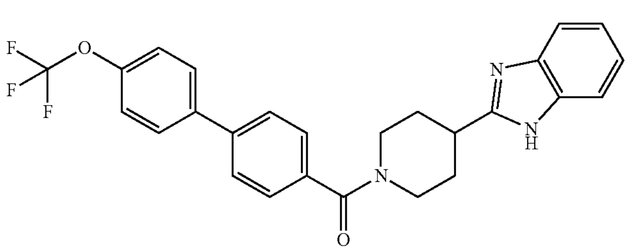 [SMILES: O=C(c1ccc(-c2ccc(OC(F)(F)F)cc2)cc1)N1CCC(c2nc3ccccc3[nH]2)CC1] | [4-(1H-benzimidazol-2-yl)piperidin-1-yl][4'-(trifluoromethoxy)biphenyl-4-yl)methanone |

TABLE I-continued

| # | Structure | Name |
|---|---|---|
| 38 | 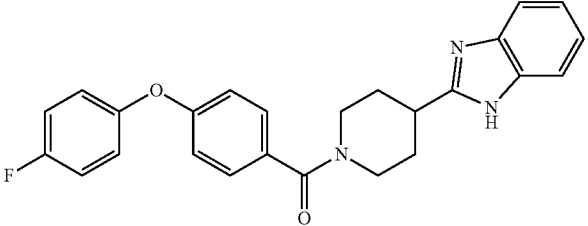 [SMILES: O=C(c1ccc(Oc2ccc(F)cc2)cc1)N1CCC(c2nc3ccccc3[nH]2)CC1] | [4-(1H-benzimidazol-2-yl)piperidin-1-yl][4-(4-fluorophenoxy)phenyl]methanone |
| 39 | 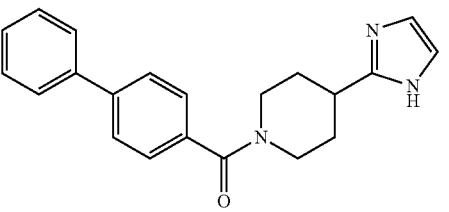 [SMILES: O=C(c1ccc(-c2ccccc2)cc1)N1CCC(c2ncc[nH]2)CC1] | biphenyl-4-yl[4-(1H-imidazol-2-yl)piperidin-1-yl]methanone |
| 40 | 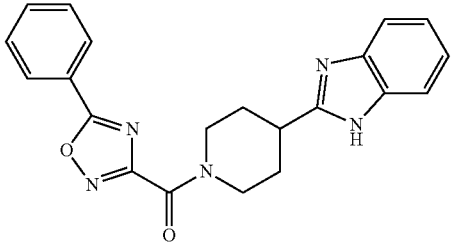 [SMILES: O=C(c1noc(-c2ccccc2)n1)N1CCC(c2nc3ccccc3[nH]2)CC1] | [4-(1H-benzimidazol-2-yl)piperidin-1-yl](5-phenyl-1,2,4-oxadiazol-3-yl)methanone |
| 41 | 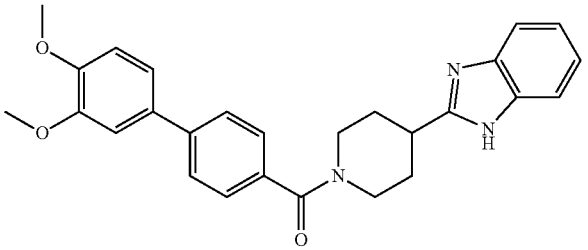 [SMILES: COc1ccc(-c2ccc(C(=O)N3CCC(c4nc5ccccc5[nH]4)CC3)cc2)cc1OC] | [4-(1H-benzimidazol-2-yl)piperidin-1-yl](3',4'-dimethoxybiphenyl-4-yl)methanone |
| 42 | 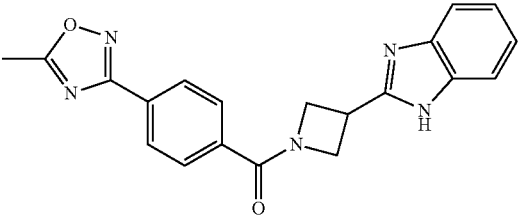 [SMILES: Cc1nc(-c2ccc(C(=O)N3CC(c4nc5ccccc5[nH]4)C3)cc2)no1] | [3-(1H-benzimidazol-2-yl)azetidin-1-yl][4-(5-methyl-1,2,4-oxadiazol-3-yl)phenyl]methanone |
| 43 | Chiral 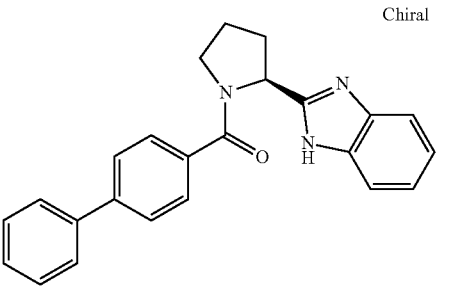 [SMILES: O=C(c1ccc(-c2ccccc2)cc1)N1CCC[C@H]1c1nc2ccccc2[nH]1] | [(2S)-2-(1H-benzimidazol-2-yl)pyrrolidin-1-yl](biphenyl-4-yl)methanone |

TABLE I-continued

| # | Structure | Name |
|---|---|---|
| 44 | 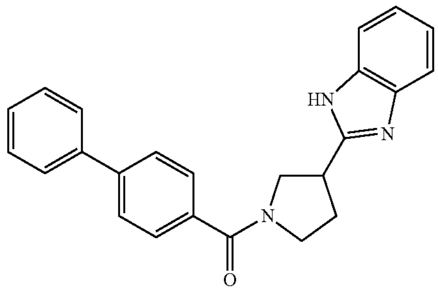 [SMILES: O=C(c1ccc(-c2ccccc2)cc1)N1CCC(c2nc3ccccc3[nH]2)C1] | [3-(1H-benzimidazol-2-yl)pyrrolidin-1-yl](biphenyl-4-yl)methanone |
| 45 | 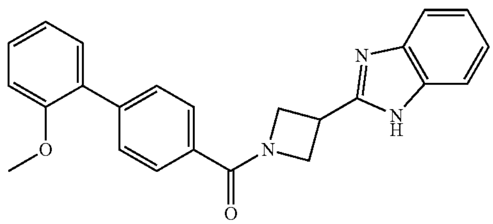 [SMILES: COc1ccccc1-c1ccc(C(=O)N2CC(c3nc4ccccc4[nH]3)C2)cc1] | [3-(1H-benzimidazol-2-yl)azetidin-1-yl](2'-methoxybiphenyl-4-yl)methanone |
| 46 | 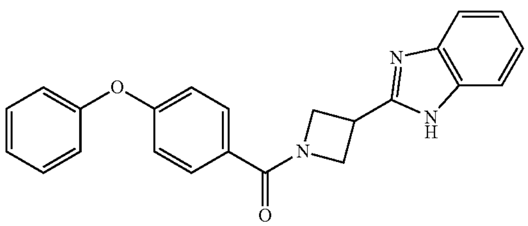 [SMILES: O=C(c1ccc(Oc2ccccc2)cc1)N1CC(c2nc3ccccc3[nH]2)C1] | [3-(1H-benzimidazol-2-yl)azetidin-1-yl](4-phenoxyphenyl)methanone |
| 47 | 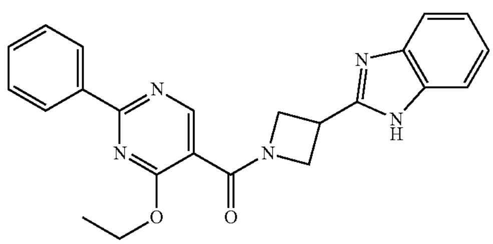 [SMILES: CCOc1nc(-c2ccccc2)ncc1C(=O)N1CC(c2nc3ccccc3[nH]2)C1] | [3-(1H-benzimidazol-2-yl)azetidin-1-yl](4-ethoxy-2-phenylpyrimidin-5-yl)methanone |
| 48 | 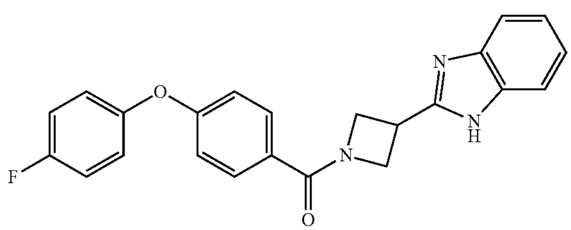 [SMILES: O=C(c1ccc(Oc2ccc(F)cc2)cc1)N1CC(c2nc3ccccc3[nH]2)C1] | [3-(1H-benzimidazol-2-yl)azetidin-1-yl][4-(4-fluorophenoxy)phenyl]methanone |
| 49 | Chiral | [(3S)-3-(1H-benzimidazol-2-yl)piperidin-1-yl](biphenyl-4-yl)methanone |

TABLE I-continued

| # | Structure | Name |
|---|---|---|
| 50 | Chiral | [(3R)-3-(1H-benzimidazol-2-yl)piperidin-1-yl](biphenyl-4-yl)methanone |
| 51 | Chiral | [(2R)-2-(1H-benzimidazol-2-yl)pyrrolidin-1-yl](biphenyl-4-yl)methanone |
| 52 | 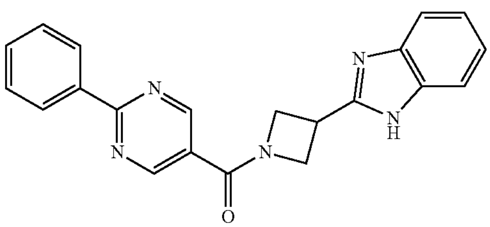 [SMILES: O=C(c1cnc(-c2ccccc2)nc1)N1CC(c2nc3ccccc3[nH]2)C1] | [3-(1H-benzimidazol-2-yl)azetidin-1-yl](2-phenylpyrimidin-5-yl)methanone |
| 53 | 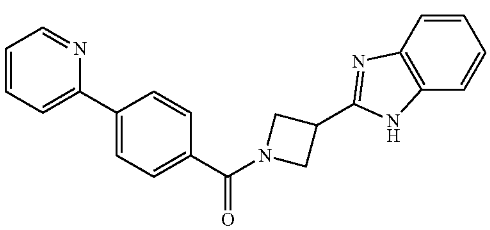 | [3-(1H-benzimidazol-2-yl)azetidin-1-yl][4-(pyridin-2-yl)phenyl]methanone |
| 54 | 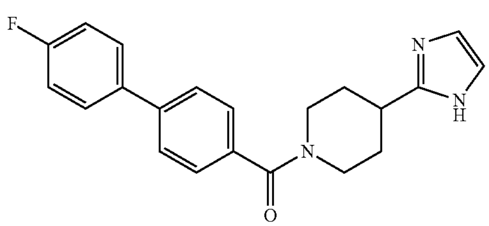 [SMILES: O=C(c1ccc(-c2ccc(F)cc2)cc1)N1CCC(c2ncc[nH]2)CC1] | (4'-fluorobiphenyl-4-yl)[4-(1H-imidazol-2-yl)piperidin-1-yl]methanone |
| 55 | 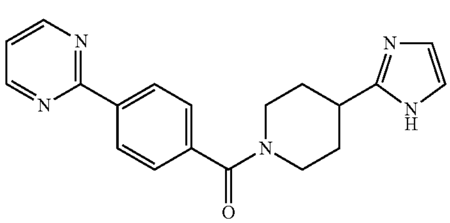 [SMILES: O=C(c1ccc(-c2ncccn2)cc1)N1CCC(c2ncc[nH]2)CC1] | [4-(1H-imidazol-2-yl)piperidin-1-yl][4-(pyrimidin-2-yl)phenyl]methanone |

TABLE I-continued

| # | Structure | Name |
|---|---|---|
| 56 | 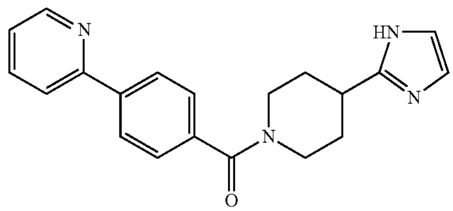 [SMILES: O=C(c1ccc(-c2ccccn2)cc1)N1CCC(c2ncc[nH]2)CC1] | [4-(1H-imidazol-2-yl)piperidin-1-yl][4-(pyridin-2-yl)phenyl]methanone |
| 57 | 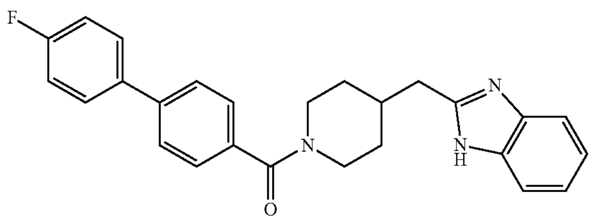 [SMILES: O=C(c1ccc(-c2ccc(F)cc2)cc1)N1CCC(Cc2nc3ccccc3[nH]2)CC1] | [4-(1H-benzimidazol-2-ylmethyl)piperidin-1-yl](4'-fluorobiphenyl-4-yl)methanone |
| 58 | Chiral | [(2S)-2-(1H-benzimidazol-2-yl)pyrrolidin-1-yl](4'-fluorobiphenyl-4-yl)methanone |
| 59 | Chiral | [(2S)-2-(1H-benzimidazol-2-yl)pyrrolidin-1-yl][4-(pyridin-2-yl)phenyl]methanone |
| 60 | 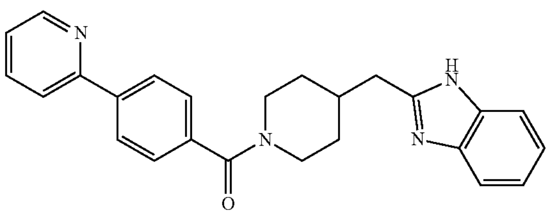 [SMILES: O=C(c1ccc(-c2ccccn2)cc1)N1CCC(Cc2nc3ccccc3[nH]2)CC1] | [4-(1H-benzimidazol-2-ylmethyl)piperidin-1-yl][4-(pyridin-2-yl)phenyl]methanone |

TABLE I-continued

| # | Structure | Name |
|---|---|---|
| 61 | Chiral | biphenyl-4-yl[(2S)-2-(1H-imidazol-2-yl)pyrrolidin-1-yl]methanone |
| 62 | 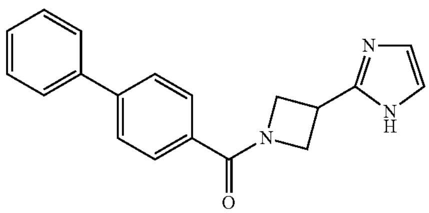 [SMILES: O=C(c1ccc(-c2ccccc2)cc1)N1CC(c2ncc[nH]2)C1] | biphenyl-4-yl[3-(1H-imidazol-2-yl)azetidin-1-yl]methanone |
| 63 | 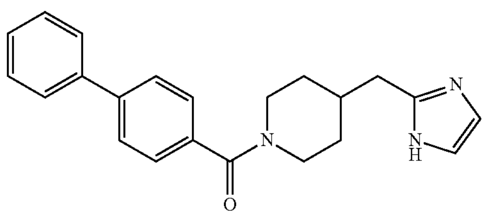 [SMILES: O=C(c1ccc(-c2ccccc2)cc1)N1CCC(Cc2ncc[nH]2)CC1] | biphenyl-4-yl[4-(1H-imidazol-2-ylmethyl)piperidin-1-yl]methanone |
| 64 | 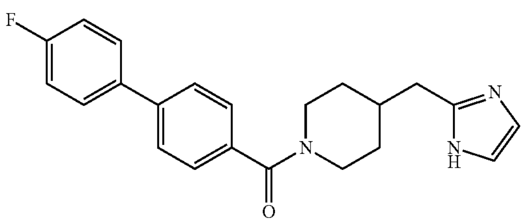 [SMILES: O=C(c1ccc(-c2ccc(F)cc2)cc1)N1CCC(Cc2ncc[nH]2)CC1] | (4'-fluorobiphenyl-4-yl)[4-(1H-imidazol-2-ylmethyl)piperidin-1-yl]methanone |
| 65 | 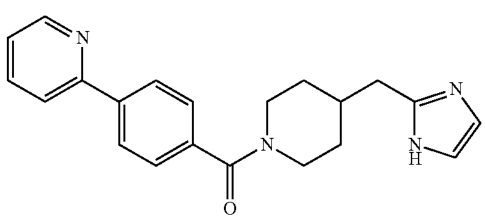 [SMILES: O=C(c1ccc(-c2ccccn2)cc1)N1CCC(Cc2ncc[nH]2)CC1] | [4-(1H-imidazol-2-ylmethyl)piperidin-1-yl][4-(pyridin-2-yl)phenyl]methanone |
| 66 | Chiral | (4'-fluorobiphenyl-4-yl)[(2S)-2-(1H-imidazol-2-yl)pyrrolidin-1-yl]methanone |

TABLE I-continued

| # | Structure | Name |
|---|---|---|
| 67 | 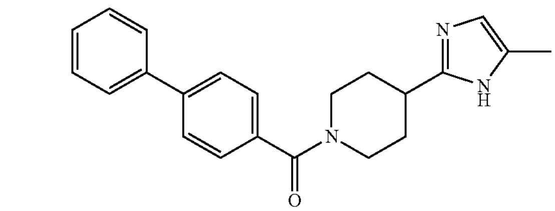 [SMILES: Cc1cnc(C2CCN(C(=O)c3ccc(-c4ccccc4)cc3)CC2)[nH]1] | Biphenyl-4-yl[4-(4-methyl-1H-imidazol-2-yl)piperidin-1-yl]methanone |
| 68 | 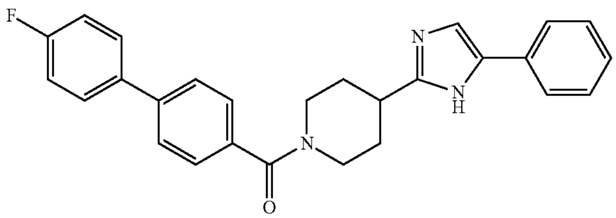 [SMILES: O=C(c1ccc(-c2ccc(F)cc2)cc1)N1CCC(c2ncc(-c3ccccc3)[nH]2)CC1] | (4'-Fluorobiphenyl-4-yl)[4-(4-phenyl-1H-imidazol-2-yl)piperidin-1-yl]methanone |
| 69 | 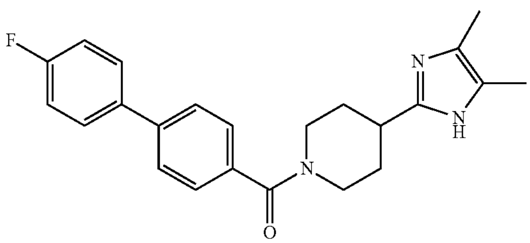 [SMILES: Cc1nc(C2CCN(C(=O)c3ccc(-c4ccc(F)cc4)cc3)CC2)[nH]c1C] | [4-(4,5-dimethyl-1H-imidazol-2-yl)piperidin-1-yl](4'-fluorobiphenyl-4-yl)methanone |
| 70 | 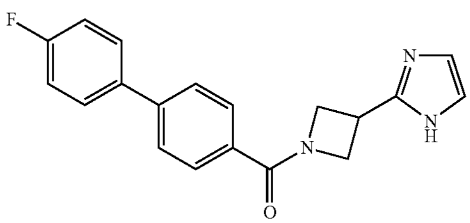 [SMILES: O=C(c1ccc(-c2ccc(F)cc2)cc1)N1CC(c2ncc[nH]2)C1] | (4'-fluorobiphenyl-4-yl)[3-(1H-imidazol-2-yl)azetidin-1-yl]methanone |
| 71 | 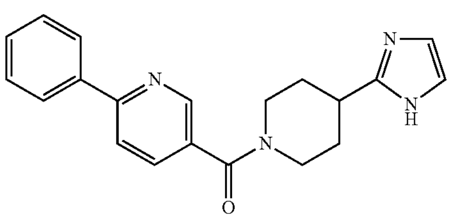 [SMILES: O=C(c1ccc(-c2ccccc2)nc1)N1CCC(c2ncc[nH]2)CC1] | [4-(1H-imidazol-2-yl)piperidin-1-yl](6-phenylpyridin-3-yl)methanone |
| 72 | 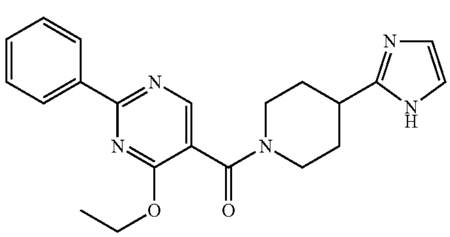 [SMILES: CCOc1nc(-c2ccccc2)ncc1C(=O)N1CCC(c2ncc[nH]2)CC1] | (4-ethoxy-2-phenylpyrimidin-5-yl)[4-(1H-imidazol-2-yl)piperidin-1-yl]methanone |
| 73 | 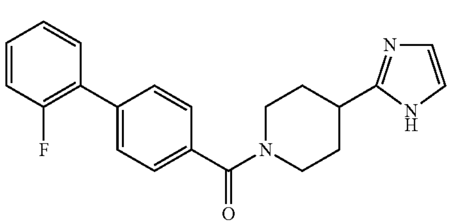 [SMILES: O=C(c1ccc(-c2ccccc2F)cc1)N1CCC(c2ncc[nH]2)CC1] | (2'-fluorobiphenyl-4-yl)[4-(1H-imidazol-2-yl)piperidin-1-yl]methanone |

TABLE I-continued

| # | Structure | Name |
|---|---|---|
| 74 | 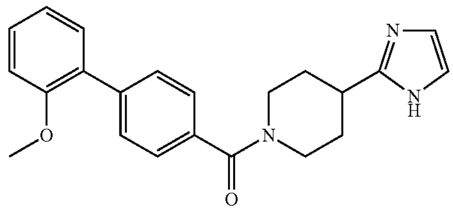 [SMILES: COc1ccccc1-c1ccc(C(=O)N2CCC(c3ncc[nH]3)CC2)cc1] | [4-(1H-imidazol-2-yl)piperidin-1-yl](2'-methoxybiphenyl-4-yl)methanone |
| 75 | 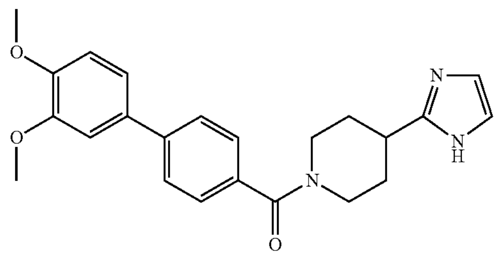 [SMILES: COc1ccc(-c2ccc(C(=O)N3CCC(c4ncc[nH]4)CC3)cc2)cc1OC] | (3',4'-dimethoxybiphenyl-4-yl)[4-(1H-imidazol-2-yl)piperidin-1-yl]methanone |
| 76 | 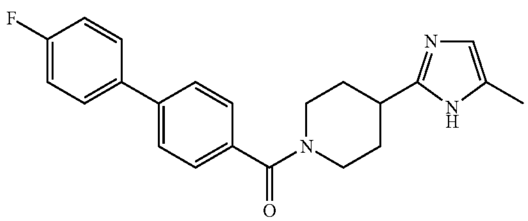 [SMILES: Cc1cnc(C2CCN(C(=O)c3ccc(-c4ccc(F)cc4)cc3)CC2)[nH]1] | (4'-Fluorobiphenyl-4-yl)[4-(4-methyl-1H-imidazol-2-yl)piperidin-1-yl]methanone |
| 77 | 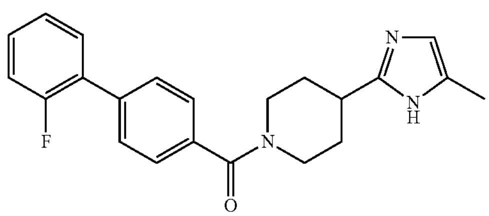 [SMILES: Cc1cnc(C2CCN(C(=O)c3ccc(-c4ccccc4F)cc3)CC2)[nH]1] | (2'-Fluorobiphenyl-4-yl)[4-(4-methyl-1H-imidazol-2-yl)piperidin-1-yl]methanone |
| 78 | 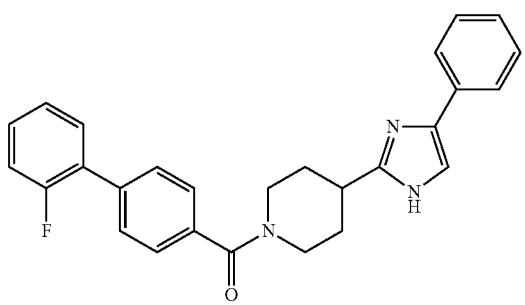 [SMILES: O=C(c1ccc(-c2ccccc2F)cc1)N1CCC(c2nc(-c3ccccc3)c[nH]2)CC1] | (2'-fluorobiphenyl-4-yl)[4-(4-phenyl-1H-imidazol-2-yl)piperidin-1-yl]methanone |
| 79 | 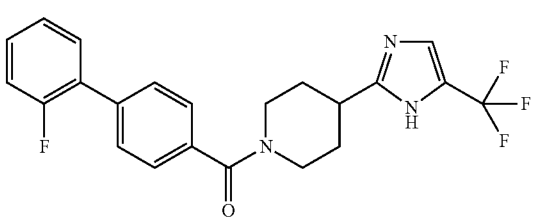 [SMILES: O=C(c1ccc(-c2ccccc2F)cc1)N1CCC(c2ncc(C(F)(F)F)[nH]2)CC1] | (2'-Fluorobiphenyl-4-yl){4-[4-(trifluoromethyl)-1H-imidazol-2-yl]piperidin-1-yl}methanone |

TABLE I-continued

| # | Structure | Name |
|---|---|---|
| 80 | 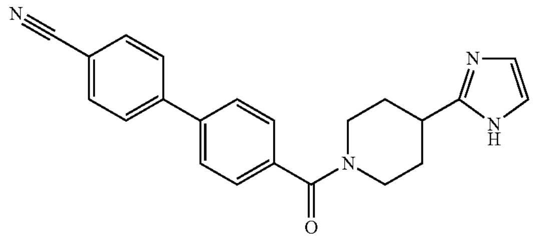 [SMILES: N#Cc1ccc(-c2ccc(C(=O)N3CCC(c4ncc[nH]4)CC3)cc2)cc1] | 4'-{[4-(1H-imidazol-2-yl)piperidin-1-yl]carbonyl}biphenyl-4-carbonitrile |
| 81 | 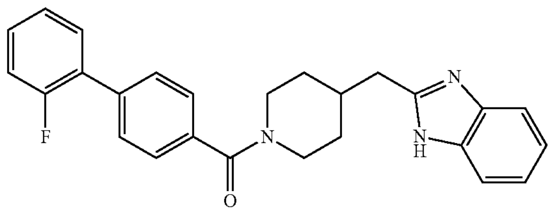 [SMILES: O=C(c1ccc(-c2ccccc2F)cc1)N1CCC(Cc2nc3ccccc3[nH]2)CC1] | [4-(1H-benzimidazol-2-ylmethyl)piperidin-1-yl](2'-fluorobiphenyl-4-yl)methanone |
| 82 | 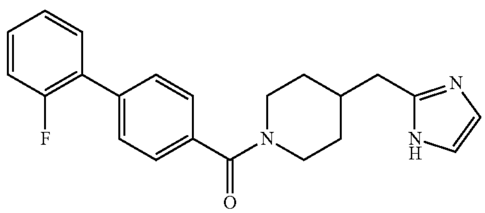 [SMILES: O=C(c1ccc(-c2ccccc2F)cc1)N1CCC(Cc2ncc[nH]2)CC1] | (2'-fluorobiphenyl-4-yl)[4-(1H-imidazol-2-ylmethyl)piperidin-1-yl]methanone |
| 83 | 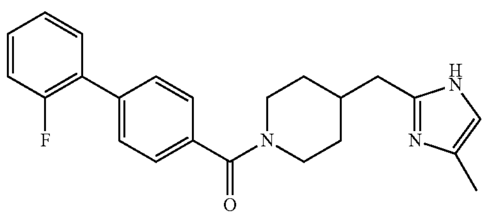 [SMILES: Cc1c[nH]c(CC2CCN(C(=O)c3ccc(-c4ccccc4F)cc3)CC2)n1] | (2'-fluorobiphenyl-4-yl){4-[(4-methyl-1H-imidazol-2-yl)methyl]piperidin-1-yl}methanone |
| 84 | 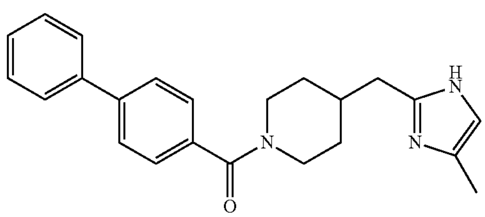 [SMILES: Cc1c[nH]c(CC2CCN(C(=O)c3ccc(-c4ccccc4)cc3)CC2)n1] | biphenyl-4-yl{4-[(4-methyl-1H-imidazol-2-yl)methyl]piperidin-1-yl}methanone |
| 85 | 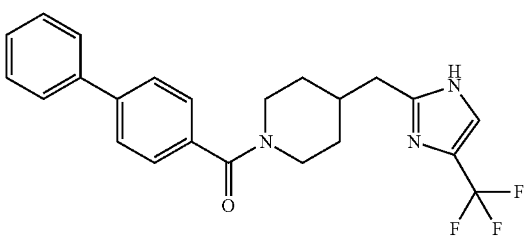 [SMILES: O=C(c1ccc(-c2ccccc2)cc1)N1CCC(Cc2nc(C(F)(F)F)c[nH]2)CC1] | biphenyl-4-yl(4-{[4-(trifluoromethyl)-1H-imidazol-2-yl]methyl}piperidin-1-yl)methanone |
| 86 | 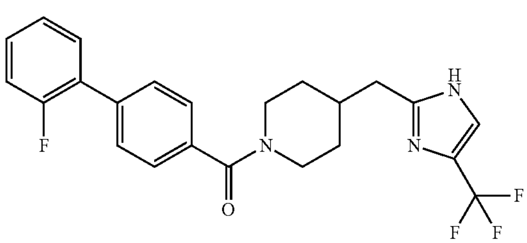 [SMILES: O=C(c1ccc(-c2ccccc2F)cc1)N1CCC(Cc2nc(C(F)(F)F)c[nH]2)CC1] | (2'-fluorobiphenyl-4-yl)(4-{[4-(trifluoromethyl)-1H-imidazol-2-yl]methyl}piperidin-1-yl)methanone |

TABLE I-continued

| # | Structure | Name |
|---|---|---|
| 87 | 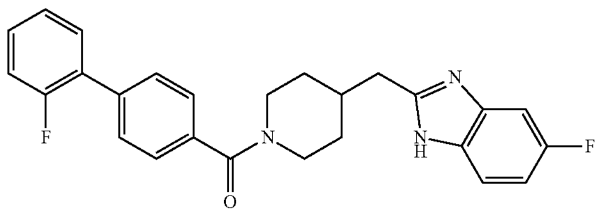 [SMILES: O=C(c1ccc(-c2ccccc2F)cc1)N1CCC(Cc2nc3cc(F)ccc3[nH]2)CC1] | {4-[(5-fluoro-1H-benzimidazol-2-yl)methyl]piperidin-1-yl}(2'-fluorobiphenyl-4-yl)methanone |
| 88 | 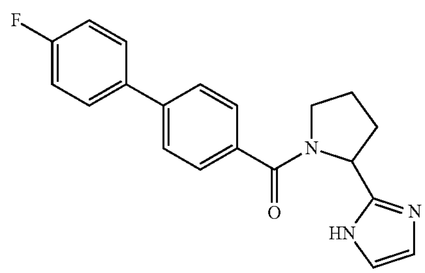 [SMILES: O=C(c1ccc(-c2ccc(F)cc2)cc1)N1CCCC1c1ncc[nH]1] | (4'-fluorobiphenyl-4-yl)[2-(1H-imidazol-2-yl)pyrrolidin-1-yl]methanone |
| 89 | 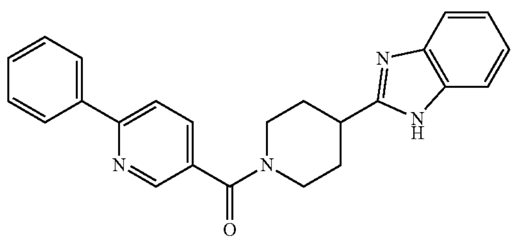 [SMILES: O=C(c1ccc(-c2ccccc2)nc1)N1CCC(c2nc3ccccc3[nH]2)CC1] | [4-(1H-benzimidazol-2-yl)piperidin-1-yl](6-phenylpyridin-3-yl)methanone |
| 90 | 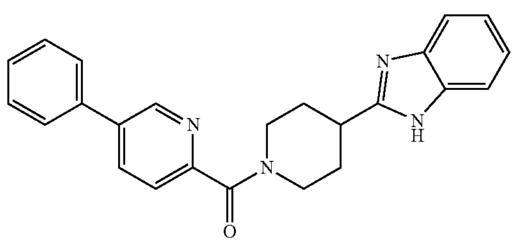 [SMILES: O=C(c1ccc(-c2ccccc2)cn1)N1CCC(c2nc3ccccc3[nH]2)CC1] | [4-(1H-benzimidazol-2-yl)piperidin-1-yl](5-phenylpyridin-2-yl)methanone |
| 91 | 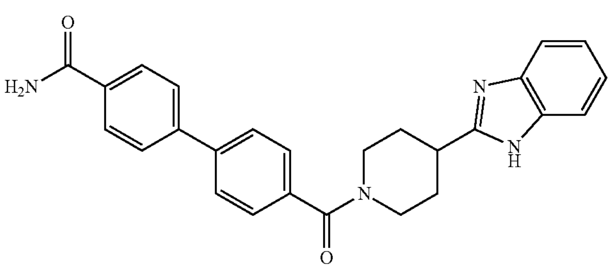 [SMILES: NC(=O)c1ccc(-c2ccc(C(=O)N3CCC(c4nc5ccccc5[nH]4)CC3)cc2)cc1] | 4'-{[4-(1H-benzimidazol-2-yl)piperidin-1-yl]carbonyl}biphenyl-4-carboxamide |
| 92 | 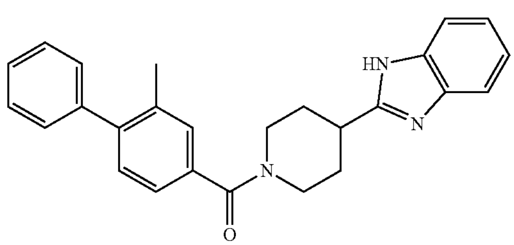 [SMILES: Cc1cc(C(=O)N2CCC(c3nc4ccccc4[nH]3)CC2)ccc1-c1ccccc1] | [4-(1H-benzimidazol-2-yl)piperidin-1-yl](2-methylbiphenyl-4-yl)methanone |

TABLE I-continued

| # | Structure | Name |
|---|---|---|
| 93 | 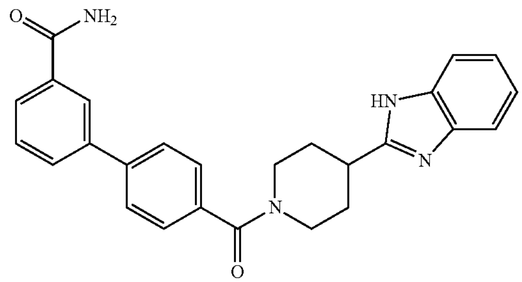 [SMILES: NC(=O)c1cccc(-c2ccc(C(=O)N3CCC(c4nc5ccccc5[nH]4)CC3)cc2)c1] | 4'-{[4-(1H-benzimidazol-2-yl)piperidin-1-yl]carbonyl}biphenyl-3-carboxamide |
| 94 | 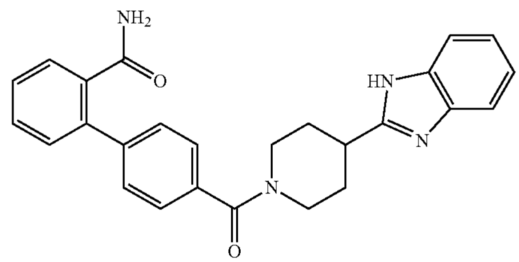 [SMILES: NC(=O)c1ccccc1-c1ccc(C(=O)N2CCC(c3nc4ccccc4[nH]3)CC2)cc1] | 4'-{[4-(1H-benzimidazol-2-yl)piperidin-1-yl]carbonyl}biphenyl-2-carboxamide |
| 95 | 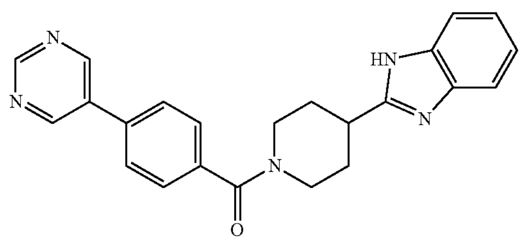 [SMILES: O=C(c1ccc(-c2cncnc2)cc1)N1CCC(c2nc3ccccc3[nH]2)CC1] | [4-(1H-benzimidazol-2-yl)piperidin-1-yl][4-(pyrimidin-5-yl)phenyl]methanone |
| 96 | 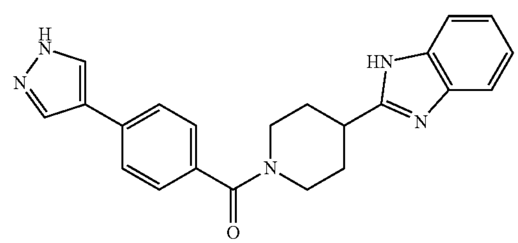 [SMILES: O=C(c1ccc(-c2cn[nH]c2)cc1)N1CCC(c2nc3ccccc3[nH]2)CC1] | [4-(1H-benzimidazol-2-yl)piperidin-1-yl][4-(1H-pyrazol-4-yl)phenyl]methanone |
| 97 | 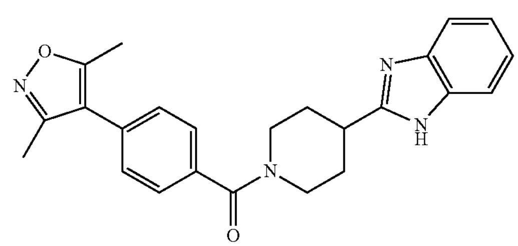 [SMILES: Cc1noc(C)c1-c1ccc(C(=O)N2CCC(c3nc4ccccc4[nH]3)CC2)cc1] | [4-(1H-benzimidazol-2-yl)piperidin-1-yl][4-(3,5-dimethylisoxazol-4-yl)phenyl]methanone |
| 98 | 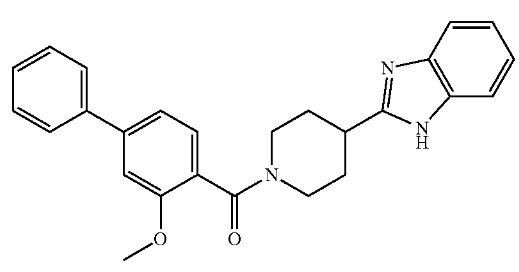 [SMILES: COc1cc(-c2ccccc2)ccc1C(=O)N1CCC(c2nc3ccccc3[nH]2)CC1] | [4-(1H-benzimidazol-2-yl)piperidin-1-yl](3-methoxybiphenyl-4-yl)methanone |

TABLE I-continued

| # | Structure | Name |
|---|---|---|
| 99 | 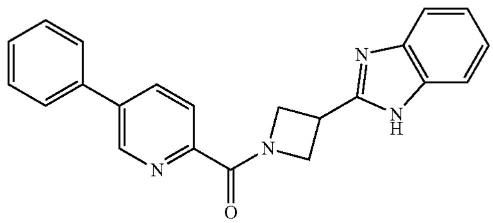 | [3-(1H-benzimidazol-2-yl)azetidin-1-yl](5-phenylpyridin-2-yl)methanone |
| 100 | 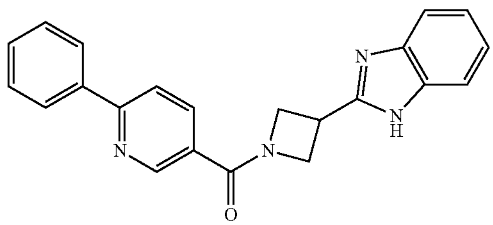 [SMILES: O=C(c1ccc(-c2ccccc2)nc1)N1CC(c2nc3ccccc3[nH]2)C1] | [3-(1H-benzimidazol-2-yl)piperidin-1-yl](6-phenylpyridin-3-yl)methanone |
| 101 | 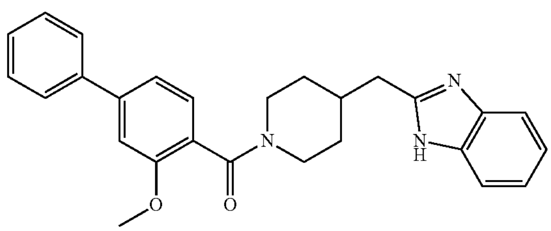 [SMILES: COc1cc(-c2ccccc2)ccc1C(=O)N1CCC(Cc2nc3ccccc3[nH]2)CC1] | [4-(1H-benzimidazol-2-ylmethyl)piperidin-1-yl](3-methoxybiphenyl-4-yl)methanone |
| 102 | 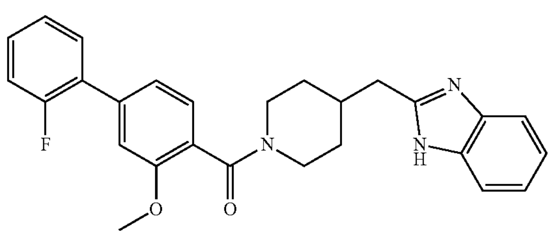 | [4-(1H-benzimidazol-2-ylmethyl)piperidin-1-yl](2'-fluoro-3-methoxybiphenyl-4-yl)methanone |
| 103 | 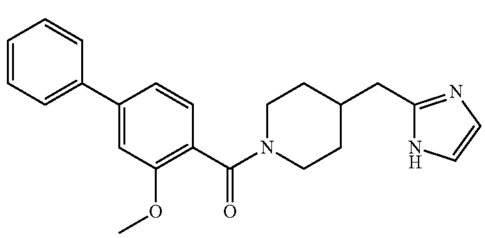 [SMILES: COc1cc(-c2ccccc2)ccc1C(=O)N1CCC(Cc2ncc[nH]2)CC1] | [4-(1H-imidazol-2-ylmethyl)piperidin-1-yl](3-methoxybiphenyl-4-yl)methanone |
| 104 | 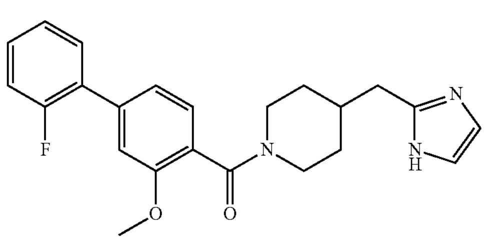 [SMILES: COc1cc(-c2ccccc2F)ccc1C(=O)N1CCC(Cc2ncc[nH]2)CC1] | (2'-fluoro-3-methoxybiphenyl-4-yl)[4-(1H-imidazol-2-ylmethyl)piperidin-1-yl]methanone |

TABLE I-continued

| # | Structure | Name |
|---|---|---|
| 105 | 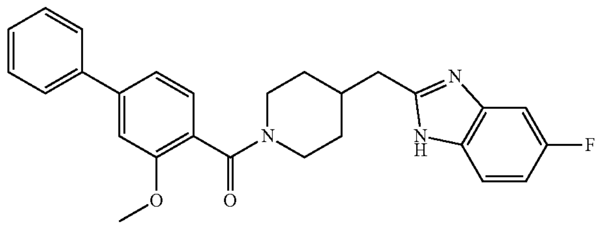 [SMILES: COc1cc(-c2ccccc2)ccc1C(=O)N1CCC(Cc2nc3cc(F)ccc3[nH]2)CC1] | {4-[(5-fluoro-1H-benzimidazol-2-yl)methyl]piperidin-1-yl}(3-methoxybiphenyl-4-yl)methanone |
| 106 | 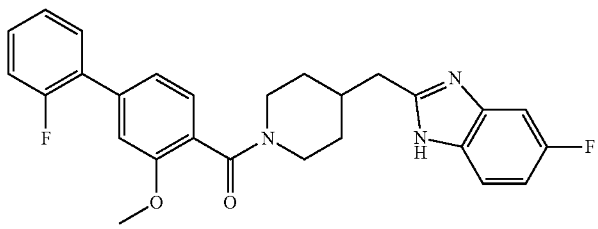 [SMILES: COc1cc(-c2ccccc2F)ccc1C(=O)N1CCC(Cc2nc3cc(F)ccc3[nH]2)CC1] | {4-[(5-fluoro-1H-benzimidazol-2-yl)methyl]piperidin-1-yl}(2'-fluoro-3-methoxybiphenyl-4-yl)methanone |
| 107 | 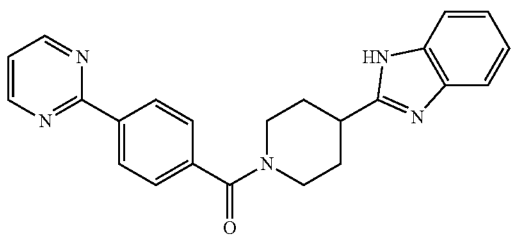 [SMILES: O=C(c1ccc(-c2ncccn2)cc1)N1CCC(c2nc3ccccc3[nH]2)CC1] | [4-(1H-benzimidazol-2-yl)piperidin-1-yl][4-(pyrimidin-2-yl)phenyl]methanone |
| 108 | 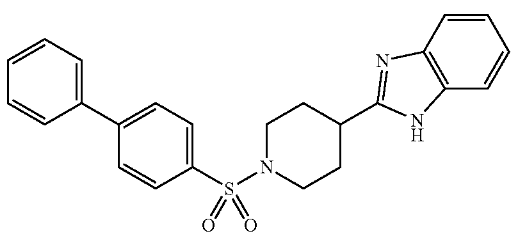 [SMILES: O=S(=O)(c1ccc(-c2ccccc2)cc1)N1CCC(c2nc3ccccc3[nH]2)CC1] | 2-[1-(biphenyl-4-ylsulfonyl)piperidin-4-yl]-1H-benzimidazole |
| 109 | 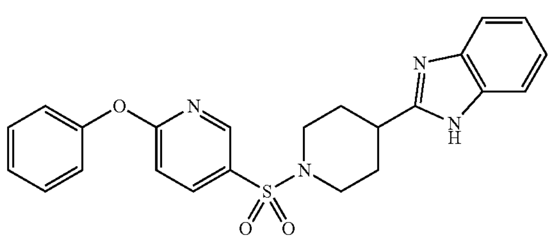 [SMILES: O=S(=O)(c1ccc(Oc2ccccc2)nc1)N1CCC(c2nc3ccccc3[nH]2)CC1] | 2-{1-[(6-phenoxypyridin-3-yl)sulfonyl]piperidin-4-yl}-1H-benzimidazole |
| 110 | 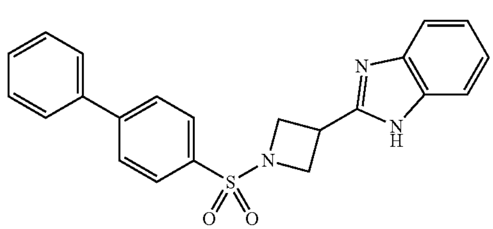 [SMILES: O=S(=O)(c1ccc(-c2ccccc2)cc1)N1CC(c2nc3ccccc3[nH]2)C1] | 2-[1-(biphenyl-4-ylsulfonyl)azetidin-3-yl]-1H-benzimidazole |

TABLE I-continued

| # | Structure | Name |
|---|---|---|
| 111 | 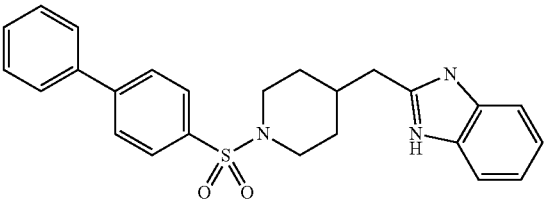 [SMILES: O=S(=O)(c1ccc(-c2ccccc2)cc1)N1CCC(Cc2nc3ccccc3[nH]2)CC1] | 2-{[1-(biphenyl-4-ylsulfonyl)piperidin-4-yl]methyl}-1H-benzimidazole |
| 112 | 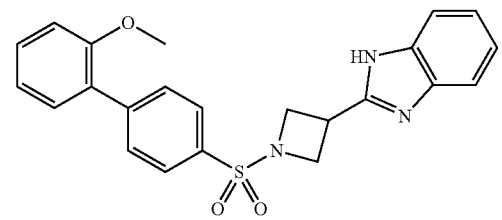 [SMILES: COc1ccccc1-c1ccc(S(=O)(=O)N2CC(c3nc4ccccc4[nH]3)C2)cc1] | 2-{1-[(2'-methoxybiphenyl-4-yl)sulfonyl]azetidin-3-yl}-1H-benzimidazole |
| 113 | 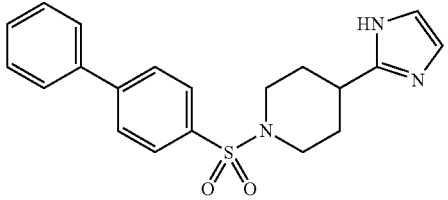 [SMILES: O=S(=O)(c1ccc(-c2ccccc2)cc1)N1CCC(c2ncc[nH]2)CC1] | 1-(biphenyl-4-ylsulfonyl)-4-(1H-imidazol-2-yl)piperidine |
| 114 | Chiral<br>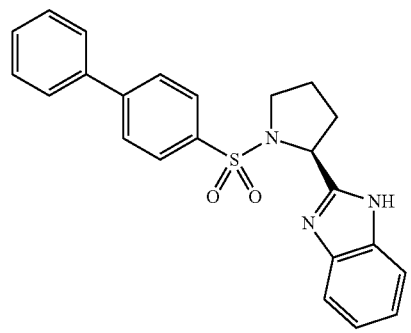 | 2-[(2S)-1-(biphenyl-4-ylsulfonyl)pyrrolidin-2-yl]-1H-benzimidazole |
| 115 | 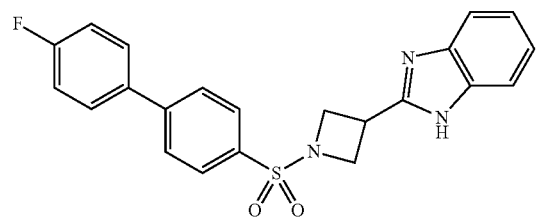 [SMILES: O=S(=O)(c1ccc(-c2ccc(F)cc2)cc1)N1CC(c2nc3ccccc3[nH]2)C1] | 2-{1-[(4'-fluorobiphenyl-4-yl)sulfonyl]azetidin-3-yl}-1H-benzimidazole |
| 116 | 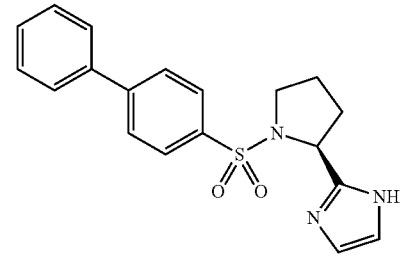 [SMILES: O=S(=O)(c1ccc(-c2ccccc2)cc1)N1CCC[C@H]1c1ncc[nH]1] | 2-[(2S)-1-(biphenyl-4-ylsulfonyl)pyrrolidin-2-yl]-1H-imidazole |

TABLE I-continued

| # | Structure | Name |
|---|---|---|
| 117 | 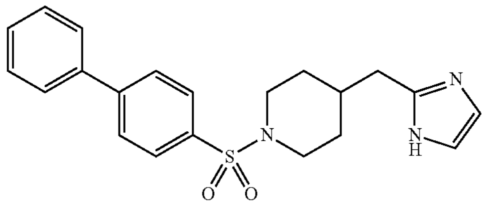 [SMILES: O=S(=O)(c1ccc(-c2ccccc2)cc1)N1CCC(Cc2ncc[nH]2)CC1] | 1-(biphenyl-4-ylsulfonyl)-4-(1H-imidazol-2-ylmethyl)piperidine |
| 118 | 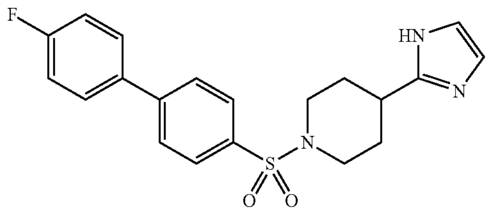 [SMILES: O=S(=O)(c1ccc(-c2ccc(F)cc2)cc1)N1CCC(c2ncc[nH]2)CC1] | 1-[(4'-fluorobiphenyl-4-yl)sulfonyl]-4-(1H-imidazol-2-yl)piperidine |
| 119 | Chiral | 2-{(2S)-1-[(4'-fluorobiphenyl-4-yl)sulfonyl]pyrrolidin-2-yl}-1H-imidazole |
| 120 | 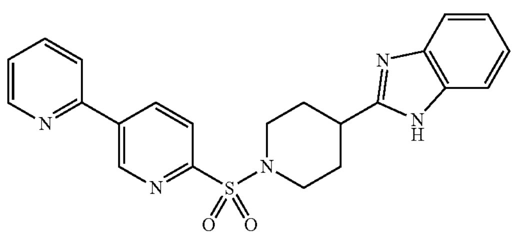 [SMILES: O=S(=O)(c1ccc(-c2ccccn2)cn1)N1CCC(c2nc3ccccc3[nH]2)CC1] | [4-(1H-benzimidazol-2-yl)piperidin-1-yl](2,3'-bipyridin-6'-yl)methanone |
| 121 | 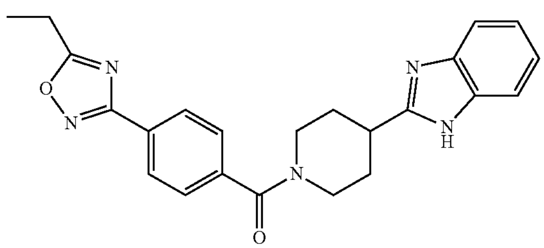 [SMILES: CCc1nc(-c2ccc(C(=O)N3CCC(c4nc5ccccc5[nH]4)CC3)cc2)no1] | [4-(1H-benzimidazol-2-yl)piperidin-1-yl][4-(5-ethyl-1,2,4-oxadiazol-3-yl)phenyl]methanone |
| 122 | 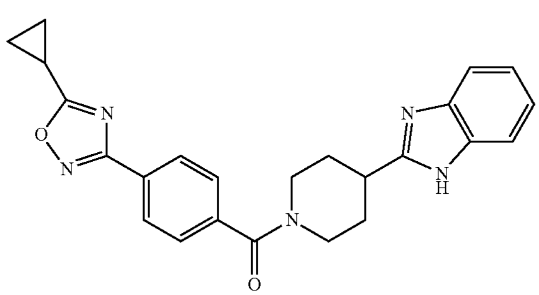 [SMILES: O=C(c1ccc(-c2noc(C3CC3)n2)cc1)N1CCC(c2nc3ccccc3[nH]2)CC1] | [4-(1H-benzimidazol-2-yl)piperidin-1-yl][4-(5-cyclopropyl-1,2,4-oxadiazol-3-yl)phenyl]methanone |

TABLE I-continued

| # | Structure | Name |
|---|---|---|
| 123 | 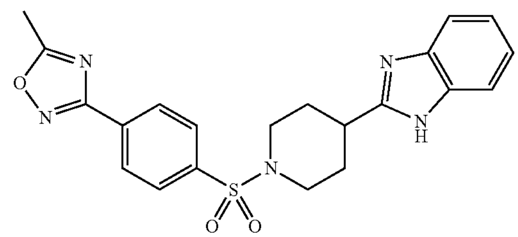 [SMILES: Cc1nc(-c2ccc(S(=O)(=O)N3CCC(c4nc5ccccc5[nH]4)CC3)cc2)no1] | 2-(1-{[4-(5-methyl-1,2,4-oxadiazol-3-yl)phenyl]sulfonyl}piperidin-4-yl)-1H-benzimidazole |
| 124 | 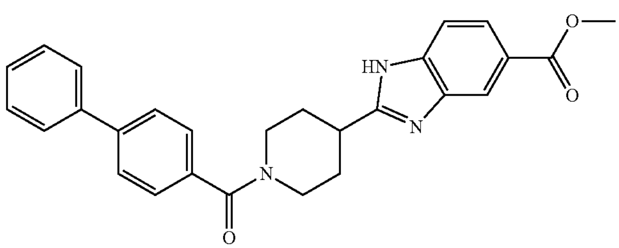 [SMILES: COC(=O)c1ccc2[nH]c(C3CCN(C(=O)c4ccc(-c5ccccc5)cc4)CC3)nc2c1] | methyl 2-[1-(biphenyl-4-ylcarbonyl)piperidin-4-yl]-1H-benzimidazole-5-carboxylate |
| 125 | 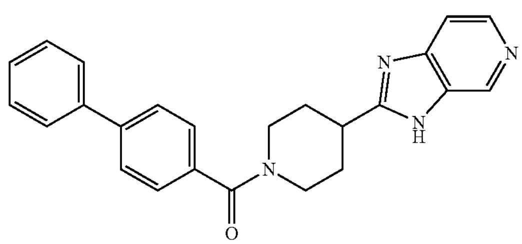 [SMILES: O=C(c1ccc(-c2ccccc2)cc1)N1CCC(c2nc3ccncc3[nH]2)CC1] | Biphenyl-4-yl[4-(1H-imidazo[4,5-c]pyridin-2-yl)piperidin-1-yl]methanone |
| 126 | 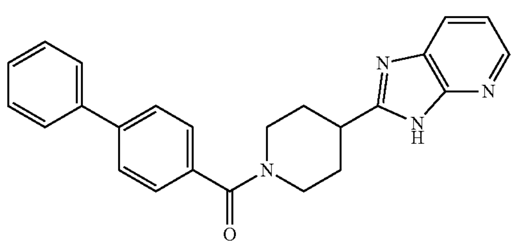 [SMILES: O=C(c1ccc(-c2ccccc2)cc1)N1CCC(c2nc3cccnc3[nH]2)CC1] | Biphenyl-4-yl[4-(1H-imidazo[4,5-b]pyridin-2-yl)piperidin-1-yl]methanone |
| 127 | 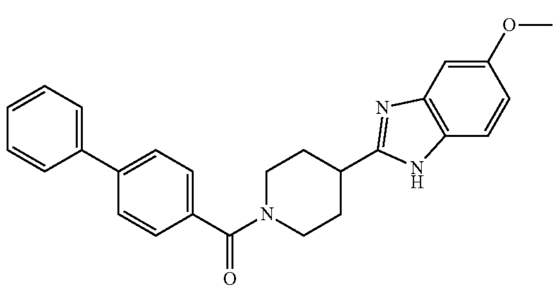 [SMILES: COc1ccc2[nH]c(C3CCN(C(=O)c4ccc(-c5ccccc5)cc4)CC3)nc2c1] | biphenyl-4-yl[4-(5-methoxy-1H-benzimidazol-2-yl)piperidin-1-yl]methanone |
| 128 | 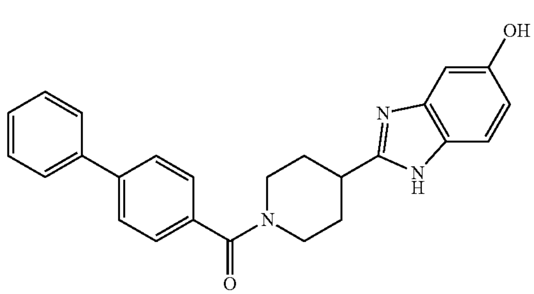 [SMILES: O=C(c1ccc(-c2ccccc2)cc1)N1CCC(c2nc3cc(O)ccc3[nH]2)CC1] | biphenyl-4-yl[4-(5-hydroxy-1H-benzimidazol-2-yl)piperidin-1-yl]methanone |

TABLE I-continued

| # | Structure | Name |
|---|---|---|
| 129 | 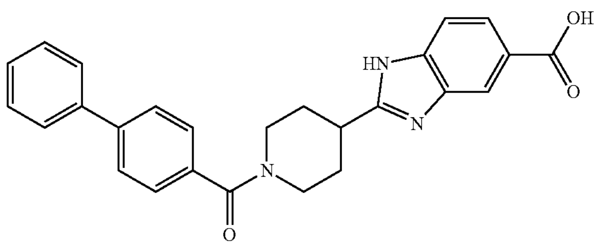 [SMILES: O=C(O)c1ccc2[nH]c(C3CCN(C(=O)c4ccc(-c5ccccc5)cc4)CC3)nc2c1] | 2-[1-(biphenyl-4-ylcarbonyl)piperidin-4-yl]-1H-benzimidazole-5-carboxylic acid |
| 130 | 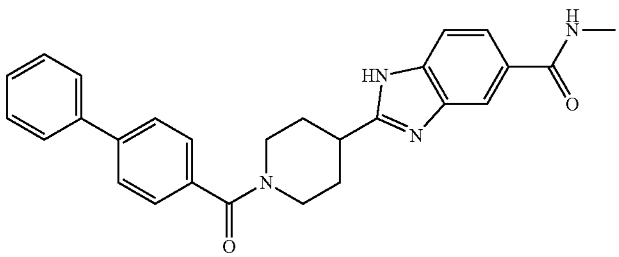 [SMILES: CNC(=O)c1ccc2[nH]c(C3CCN(C(=O)c4ccc(-c5ccccc5)cc4)CC3)nc2c1] | 2-[1-(biphenyl-4-ylcarbonyl)piperidin-4-yl]-N-methyl-1H-benzimidazole-5-carboxamide |
| 131 | 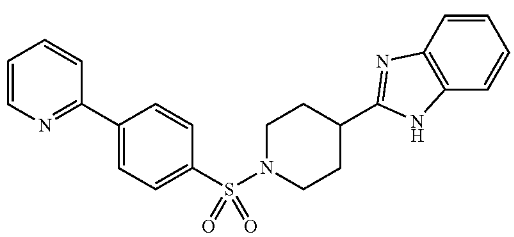 [SMILES: O=S(=O)(c1ccc(-c2ccccn2)cc1)N1CCC(c2nc3ccccc3[nH]2)CC1] | 2-(1-{[4-(pyridin-2-yl)phenyl]sulfonyl}piperidin-4-yl)-1H-benzimidazole |
| 132 | 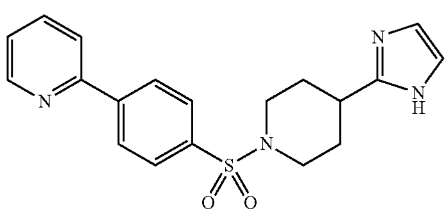 [SMILES: O=S(=O)(c1ccc(-c2ccccn2)cc1)N1CCC(c2ncc[nH]2)CC1] | 2-(4-{[4-(1H-imidazol-2-yl)piperidin-1-yl]sulfonyl}phenyl)pyridine |
| 133 | 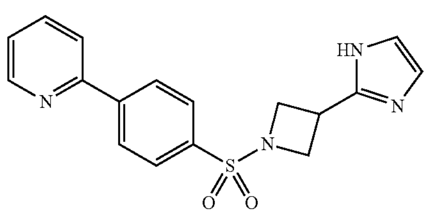 [SMILES: O=S(=O)(c1ccc(-c2ccccn2)cc1)N1CC(c2ncc[nH]2)C1] | 2-(4-{[3-(1H-imidazol-2-yl)azetidin-1-yl]sulfonyl}phenyl)pyridine |
| 134 | 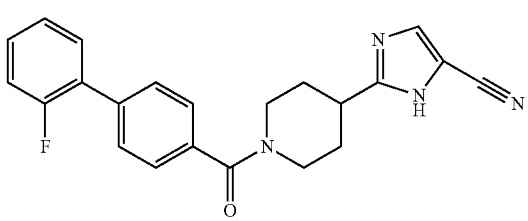 [SMILES: N#Cc1cnc(C2CCN(C(=O)c3ccc(-c4ccccc4F)cc3)CC2)[nH]1] | 2-{1-[(2'-Fluorobiphenyl-4-yl)carbonyl]piperidin-4-yl}-1H-imidazole-4-carbonitrile |

TABLE I-continued

| # | Structure | Name |
|---|---|---|
| 135 | 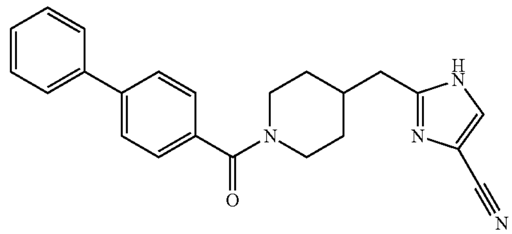 [SMILES: N#Cc1c[nH]c(CC2CCN(C(=O)c3ccc(-c4ccccc4)cc3)CC2)n1] | 2-{[1-(biphenyl-4-ylcarbonyl)piperidin-4-yl]methyl}-1H-imidazole-4-carbonitrile |
| 136 | 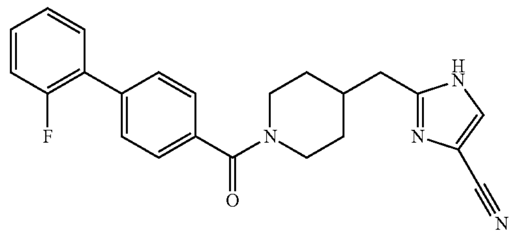 [SMILES: N#Cc1c[nH]c(CC2CCN(C(=O)c3ccc(-c4ccccc4F)cc3)CC2)n1] | 2-({1-[(2'-fluorobiphenyl-4-yl)carbonyl]piperidin-4-yl}methyl)-1H-imidazole-4-carbonitrile |

In another embodiment, the invention provides "preferred" compounds of the formula (I) listed immediately below that can be made in view of the general synthesis and examples provided herein, and materials and methods known in the art.

[4-(1H-benzimidazol-2-yl)piperidin-1-yl](2'-chlorobiphenyl-4-yl)methanone
[4-(1H-benzimidazol-2-yl)piperidin-1-yl](3'-chlorobiphenyl-4-yl)methanone
[4-(1H-benzimidazol-2-yl)piperidin-1-yl](4'-chlorobiphenyl-4-yl)methanone
[4-(1H-benzimidazol-2-yl)piperidin-1-yl](2'-fluorobiphenyl-4-yl)methanone
[4-(1H-benzimidazol-2-yl)piperidin-1-yl](3'-fluorobiphenyl-4-yl)methanone
[4-(1H-benzimidazol-2-yl)piperidin-1-yl](4'-fluorobiphenyl-4-yl)methanone
[4-(1H-benzimidazol-2-yl)piperidin-1-yl][4-(pyridin-3-yl)phenyl]methanone
[4-(1H-Benzimidazol-2-yl)piperidin-1-yl](5-phenyl-2-thienyl)methanone
[4-(1H-Benzimidazol-2-yl)piperidin-1-yl][4-(2-thienyl)phenyl]methanone
[4-(5-fluoro-1H-benzimidazol-2-yl)piperidin-1-yl](4'-fluorobiphenyl-4-yl)methanone
biphenyl-4-yl[4-(5,6-difluoro-1H-benzimidazol-2-yl)piperidin-1-yl]methanone
[4-(5,6-difluoro-1H-benzimidazol-2-yl)piperidin-1-yl](4'-fluorobiphenyl-4-yl)methanone
[3-(1H-benzimidazol-2-yl) azetidin-1-yl](biphenyl-4-yl)methanone
[4-(1H-benzimidazol-2-yl)piperidin-1-yl][4-(5-methyl-1,2,4-oxadiazol-3-yl)phenyl]methanone
[4-(1H-benzimidazol-2-yl)piperidin-1-yl](4-phenoxyphenyl)methanone
[4-(1H-benzimidazol-2-yl)piperidin-1-yl](4'-methoxybiphenyl-4-yl)methanone
[4-(1H-benzimidazol-2-yl)piperidin-1-yl](3'-methoxybiphenyl-4-yl)methanone
[4-(1H-benzimidazol-2-yl)piperidin-1-yl](2'-methoxybiphenyl-4-yl)methanone
[4-(1H-benzimidazol-2-yl)piperidin-1-yl][4-(phenylsulfonyl)phenyl]methanone
[4-(1H-benzimidazol-2-yl)piperidin-1-yl][4'-(2-methoxyethoxy)biphenyl-4-yl]methanone
[3-(1H-benzimidazol-2-yl)piperidin-1-yl](biphenyl-4-yl)methanone
[4-(1H-benzimidazol-2-yl)piperidin-1-yl][4-(pyridin-2-yl)phenyl]methanone
[4-(1H-Benzimidazol-2-yl)-4-methylpiperidin-1-yl](biphenyl-4-yl)methanone
[4-(1H-benzimidazol-2-ylmethyl)piperidin-1-yl](biphenyl-4-yl)methanone
[4-(1H-benzimidazol-2-yl)piperidin-1-yl](2-phenyl-1,3-thiazol-4-yl)methanone
[4-(1H-benzimidazol-2-yl)piperidin-1-yl](4-ethoxy-2-phenylpyrimidin-5-yl)methanone
[4-(1H-benzimidazol-2-yl)piperidin-1-yl][6-(3-methoxyphenyl)pyridin-3-yl]methanone
[4-(1H-benzimidazol-2-yl)piperidin-1-yl](2-phenylpyrimidin-5-yl)methanone
[4-(1H-benzimidazol-2-yl)piperidin-1-yl](4-phenyl-1,3-thiazol-2-yl)methanone
3-{[4-(1H-benzimidazol-2-yl)piperidin-1-yl]carbonyl}-6-phenylpyridin-2(1H)-one
[4-(1H-Benzimidazol-2-yl)piperidin-1-yl](1-phenyl-1H-pyrazol-4-yl)methanone
[4-(1H-Benzimidazol-2-yl)piperidin-1-yl](4-phenyl-2-thienyl)methanone
[4-(1H-benzimidazol-2-yl)piperidin-1-yl](2-phenyl-1,3-thiazol-5-yl)methanone
[4-(1H-benzimidazol-2-yl)piperidin-1-yl](2',4'-dimethoxybiphenyl-4-yl)methanone
[4-(1H-benzimidazol-2-yl)piperidin-1-yl][4'-(trifluoromethoxy)biphenyl-4-yl]methanone
[4-(1H-benzimidazol-2-yl)piperidin-1-yl][4-(4-fluorophenoxy)phenyl]methanone
biphenyl-4-yl[4-(1H-imidazol-2-yl)piperidin-1-yl]methanone
[4-(1H-benzimidazol-2-yl)piperidin-1-yl](3',4'-dimethoxybiphenyl-4-yl)methanone
[(2S)-2-(1H-benzimidazol-2-yl)pyrrolidin-1-yl](biphenyl-4-yl)methanone
[3-(1H-benzimidazol-2-yl)pyrrolidin-1-yl](biphenyl-4-yl)methanone

[3-(1H-benzimidazol-2-yl)azetidin-1-yl](2'-methoxybiphenyl-4-yl)methanone
[3-(1H-benzimidazol-2-yl)azetidin-1-yl](4-phenoxyphenyl)methanone
[3-(1H-benzimidazol-2-yl)azetidin-1-yl](4-ethoxy-2-phenylpyrimidin-5-yl)methanone
[3-(1H-benzimidazol-2-yl)azetidin-1-yl][4-(4-fluorophenoxy)phenyl]methanone
[(3S)-3-(1H-benzimidazol-2-yl)piperidin-1-yl](biphenyl-4-yl)methanone
[(3R)-3-(1H-benzimidazol-2-yl)piperidin-1-yl](biphenyl-4-yl)methanone
[(2R)-2-(1H-benzimidazol-2-yl)pyrrolidin-1-yl](biphenyl-4-yl)methanone
[3-(1H-benzimidazol-2-yl)azetidin-1-yl](2-phenylpyrimidin-5-yl)methanone
[3-(1H-benzimidazol-2-yl)azetidin-1-yl][4-(pyridin-2-yl)phenyl]methanone
(4'-fluorobiphenyl-4-yl)[4-(1H-imidazol-2-yl)piperidin-1-yl]methanone
[4-(1H-imidazol-2-yl)piperidin-1-yl][4-(pyrimidin-2-yl)phenyl]methanone
[4-(1H-imidazol-2-yl)piperidin-1-yl][4-(pyridin-2-yl)phenyl]methanone
[4-(1H-benzimidazol-2-ylmethyl)piperidin-1-yl](4'-fluorobiphenyl-4-yl)methanone
[(2S)-2-(1H-benzimidazol-2-yl)pyrrolidin-1-yl](4'-fluorobiphenyl-4-yl)methanone
[(2S)-2-(1H-benzimidazol-2-yl)pyrrolidin-1-yl][4-(pyridin-2-yl)phenyl]methanone
[4-(1H-benzimidazol-2-ylmethyl)piperidin-1-yl][4-(pyridin-2-yl)phenyl]methanone
biphenyl-4-yl[4-(1H-imidazol-2-ylmethyl)piperidin-1-yl]methanone
(4'-fluorobiphenyl-4-yl)[4-(1H-imidazol-2-ylmethyl)piperidin-1-yl]methanone
[4-(1H-imidazol-2-ylmethyl)piperidin-1-yl][4-(pyridin-2-yl)phenyl]methanone
Biphenyl-4-yl[4-(4-methyl-1H-imidazol-2-yl)piperidin-1-yl]methanone
(4'-Fluorobiphenyl-4-yl)[4-(4-phenyl-1H-imidazol-2-yl)piperidin-1-yl]methanone
[4-(4,5-dimethyl-1H-imidazol-2-yl)piperidin-1-yl](4'-fluorobiphenyl-4-yl)methanone
(4'-fluorobiphenyl-4-yl)[3-(1H-imidazol-2-yl)azetidin-1-yl]methanone
[4-(1H-imidazol-2-yl)piperidin-1-yl](6-phenylpyridin-3-yl)methanone
(4-ethoxy-2-phenylpyrimidin-5-yl)[4-(1H-imidazol-2-yl)piperidin-1-yl]methanone
(2'-fluorobiphenyl-4-yl)[4-(1H-imidazol-2-yl)piperidin-1-yl]methanone
[4-(1H-imidazol-2-yl)piperidin-1-yl](2'-methoxybiphenyl-4-yl)methanone
(3',4'-dimethoxybiphenyl-4-yl)[4-(1H-imidazol-2-yl)piperidin-1-yl]methanone
(4'-Fluorobiphenyl-4-yl)[4-(4-methyl-1H-imidazol-2-yl)piperidin-1-yl]methanone
(2'-Fluorobiphenyl-4-yl)[4-(4-methyl-1H-imidazol-2-yl)piperidin-1-yl]methanone
(2'-fluorobiphenyl-4-yl)[4-(4-phenyl-1H-imidazol-2-yl)piperidin-1-yl]methanone
(2'-Fluorobiphenyl-4-yl){4-[4-(trifluoromethyl)-1H-imidazol-2-yl]piperidin-1-yl}methanone
4'-{[4-(1H-imidazol-2-yl)piperidin-1-yl]carbonyl}biphenyl-4-carbonitrile
[4-(1H-benzimidazol-2-ylmethyl)piperidin-1-yl](2'-fluorobiphenyl-4-yl)methanone
(2'-fluorobiphenyl-4-yl)[4-(1H-imidazol-2-ylmethyl)piperidin-1-yl]methanone
(2'-fluorobiphenyl-4-yl){4-[(4-methyl-1H-imidazol-2-yl)methyl]piperidin-1-yl}methanone
biphenyl-4-yl{4-[(4-methyl-1H-imidazol-2-yl)methyl]piperidin-1-yl}methanone
biphenyl-4-yl(4-{[4-(trifluoromethyl)-1H-imidazol-2-yl]methyl}piperidin-1-yl)methanone
(2'-fluorobiphenyl-4-yl)(4-{[4-(trifluoromethyl)-1H-imidazol-2-yl]methyl}piperidin-1-yl)methanone
{4-[(5-fluoro-1H-benzimidazol-2-yl)methyl]piperidin-1-yl}(2'-fluorobiphenyl-4-yl)methanone
[4-(1H-benzimidazol-2-yl)piperidin-1-yl](6-phenylpyridin-3-yl)methanone
[4-(1H-benzimidazol-2-yl)piperidin-1-yl](5-phenylpyridin-2-yl)methanone
[4-(1H-benzimidazol-2-yl)piperidin-1-yl](2-methylbiphenyl-4-yl)methanone
4'-{[4-(1H-benzimidazol-2-yl)piperidin-1-yl]carbonyl}biphenyl-3-carboxamide
[4-(1H-benzimidazol-2-yl)piperidin-1-yl](3-methoxybiphenyl-4-yl)methanone
[3-(1H-benzimidazol-2-yl)azetidin-1-yl](6-phenylpyridin-3-yl)methanone
[4-(1H-benzimidazol-2-ylmethyl)piperidin-1-yl](3-methoxybiphenyl-4-yl)methanone
[4-(1H-benzimidazol-2-ylmethyl)piperidin-1-yl](2'-fluoro-3-methoxybiphenyl-4-yl)methanone
[4-(1H-imidazol-2-ylmethyl)piperidin-1-yl](3-methoxybiphenyl-4-yl)methanone
(2'-fluoro-3-methoxybiphenyl-4-yl)[4-(1H-imidazol-2-ylmethyl)piperidin-1-yl]methanone
{4-[(5-fluoro-1H-benzimidazol-2-yl)methyl]piperidin-1-yl}(3-methoxybiphenyl-4-yl)methanone
{4-[(5-fluoro-1H-benzimidazol-2-yl)methyl]piperidin-1-yl}(2'-fluoro-3-methoxybiphenyl-4-yl)methanone
[4-(1H-benzimidazol-2-yl)piperidin-1-yl][4-(pyrimidin-2-yl)phenyl]methanone
2-[1-(biphenyl-4-ylsulfonyl)piperidin-4-yl]-1H-benzimidazole
2-{1-[(6-phenoxypyridin-3-yl)sulfonyl]piperidin-4-yl}-1H-benzimidazole
2-[1-(biphenyl-4-ylsulfonyl)azetidin-3-yl]-1H-benzimidazole
2-{1-[(2'-methoxybiphenyl-4-yl)sulfonyl]azetidin-3-yl}-1H-benzimidazole
1-(biphenyl-4-ylsulfonyl)-4-(1H-imidazol-2-yl)piperidine
2-[(2S)-1-(biphenyl-4-ylsulfonyl)pyrrolidin-2-yl]-1H-benzimidazole
2-{1-[(4'-fluorobiphenyl-4-yl)sulfonyl]azetidin-3-yl}-1H-benzimidazole
1-(biphenyl-4-ylsulfonyl)-4-(1H-imidazol-2-ylmethyl)piperidine
1-[(4'-fluorobiphenyl-4-yl)sulfonyl]-4-(1H-imidazol-2-yl)piperidine
[4-(1H-benzimidazol-2-yl)piperidin-1-yl](2,3'-bipyridin-6'-yl)methanone
[4-(1H-benzimidazol-2-yl)piperidin-1-yl][4-(5-ethyl-1,2,4-oxadiazol-3-yl)phenyl]methanone
[4-(1H-benzimidazol-2-yl)piperidin-1-yl][4-(5-cyclopropyl-1,2,4-oxadiazol-3-yl)phenyl]methanone
2-(1-{[4-(5-methyl-1,2,4-oxadiazol-3-yl)phenyl]sulfonyl}piperidin-4-yl)-1H-benzimidazole
Biphenyl-4-yl[4-(1H-imidazo[4,5-c]pyridin-2-yl)piperidin-1-yl]methanone Biphenyl-4-yl[4-(1H-imidazo[4,5-b]pyridin-2-yl)piperidin-1-yl]methanone
biphenyl-4-yl[4-(5-methoxy-1H-benzimidazol-2-yl)piperidin-1-yl]methanone
biphenyl-4-yl[4-(5-hydroxy-1H-benzimidazol-2-yl)piperidin-1-yl]methanone
2-[1-(biphenyl-4-ylcarbonyl)piperidin-4-yl]-1H-benzimidazole-5-carboxylic acid
2-(1-{[4-(pyridin-2-yl)phenyl]sulfonyl}piperidin-4-yl)-1H-benzimidazole
2-(4-{[4-(1H-imidazol-2-yl)piperidin-1-yl]sulfonyl}phenyl)pyridine
2-(4-{[3-(1H-imidazol-2-yl)azetidin-1-yl]sulfonyl}phenyl)pyridine
2-{1-[(2'-Fluorobiphenyl-4-yl)carbonyl]piperidin-4-yl}-1H-imidazole-4-carbonitrile
2-{[1-(biphenyl-4-ylcarbonyl)piperidin-4-yl]methyl}-1H-imidazole-4-carbonitrile
2-({1-[(2'-fluorobiphenyl-4-yl)carbonyl]piperidin-4-yl}methyl)-1H-imidazole-4-carbonitrile,
or a pharmaceutically acceptable salt thereof.

In another embodiment, the invention provides "most preferred" compounds of the formula (I) listed immediately below that can be made in view of the general synthesis and examples provided herein, and materials and methods known in the art.

[4-(1H-benzimidazol-2-yl)piperidin-1-yl](2'-chlorobiphenyl-4-yl)methanone
[4-(1H-benzimidazol-2-yl)piperidin-1-yl](3'-chlorobiphenyl-4-yl)methanone
[4-(1H-benzimidazol-2-yl)piperidin-1-yl](4'-chlorobiphenyl-4-yl)methanone
[4-(1H-benzimidazol-2-yl)piperidin-1-yl](2'-fluorobiphenyl-4-yl)methanone
[4-(1H-benzimidazol-2-yl)piperidin-1-yl](3'-fluorobiphenyl-4-yl)methanone
[4-(1H-benzimidazol-2-yl)piperidin-1-yl](4'-fluorobiphenyl-4-yl)methanone
[4-(5-fluoro-1H-benzimidazol-2-yl)piperidin-1-yl](4'-fluorobiphenyl-4-yl)methanone
biphenyl-4-yl[4-(5,6-difluoro-1H-benzimidazol-2-yl)piperidin-1-yl]methanone
[4-(5,6-difluoro-1H-benzimidazol-2-yl)piperidin-1-yl](4'-fluorobiphenyl-4-yl)methanone
[4-(1H-benzimidazol-2-yl)piperidin-1-yl](4-phenoxyphenyl)methanone
[4-(1H-benzimidazol-2-yl)piperidin-1-yl](4'-methoxybiphenyl-4-yl)methanone
[4-(1H-benzimidazol-2-yl)piperidin-1-yl](3'-methoxybiphenyl-4-yl)methanone
[4-(1H-benzimidazol-2-yl)piperidin-1-yl](2'-methoxybiphenyl-4-yl)methanone
[4-(1H-benzimidazol-2-yl)piperidin-1-yl][4-(pyridin-2-yl)phenyl]methanone
[4-(1H-benzimidazol-2-ylmethyl)piperidin-1-yl](biphenyl-4-yl)methanone
[4-(1H-benzimidazol-2-yl)piperidin-1-yl](4-ethoxy-2-phenylpyrimidin-5-yl)methanone
[4-(1H-benzimidazol-2-yl)piperidin-1-yl][6-(3-methoxyphenyl)pyridin-3-yl]methanone
[4-(1H-benzimidazol-2-yl)piperidin-1-yl](2-phenylpyrimidin-5-yl)methanone
3-{[4-(1H-benzimidazol-2-yl)piperidin-1-yl]carbonyl}-6-phenylpyridin-2(1H)-one
[4-(1H-benzimidazol-2-yl)piperidin-1-yl](2-phenyl-1,3-thiazol-5-yl)methanone
[4-(1H-benzimidazol-2-yl)piperidin-1-yl](2',4'-dimethoxybiphenyl-4-yl)methanone
biphenyl-4-yl[4-(1H-imidazol-2-yl)piperidin-1-yl]methanone
[4-(1H-benzimidazol-2-yl)piperidin-1-yl](3',4'-dimethoxybiphenyl-4-yl)methanone
[(2S)-2-(1H-benzimidazol-2-yl)pyrrolidin-1-yl](biphenyl-4-yl)methanone
[3-(1H-benzimidazol-2-yl)pyrrolidin-1-yl](biphenyl-4-yl)methanone
[3-(1H-benzimidazol-2-yl)azetidin-1-yl](4-ethoxy-2-phenylpyrimidin-5-yl)methanone
(4'-fluorobiphenyl-4-yl)[4-(1H-imidazol-2-yl)piperidin-1-yl]methanone
[4-(1H-benzimidazol-2-ylmethyl)piperidin-1-yl](4'-fluorobiphenyl-4-yl)methanone
[4-(1H-benzimidazol-2-ylmethyl)piperidin-1-yl][4-(pyridin-2-yl)phenyl]methanone
biphenyl-4-yl[4-(1H-imidazol-2-ylmethyl)piperidin-1-yl]methanone
(4'-fluorobiphenyl-4-yl)[4-(1H-imidazol-2-ylmethyl)piperidin-1-yl]methanone
[4-(1H-imidazol-2-ylmethyl)piperidin-1-yl][4-(pyridin-2-yl)phenyl]methanone
Biphenyl-4-yl[4-(4-methyl-1H-imidazol-2-yl)piperidin-1-yl]methanone
[4-(1H-imidazol-2-yl)piperidin-1-yl](6-phenylpyridin-3-yl)methanone
(4-ethoxy-2-phenylpyrimidin-5-yl)[4-(1H-imidazol-2-yl)piperidin-1-yl]methanone
(2'-fluorobiphenyl-4-yl)[4-(1H-imidazol-2-yl)piperidin-1-yl]methanone
[4-(1H-imidazol-2-yl)piperidin-1-yl](2'-methoxybiphenyl-4-yl)methanone
(3',4'-dimethoxybiphenyl-4-yl)[4-(1H-imidazol-2-yl)piperidin-1-yl]methanone
(4'-Fluorobiphenyl-4-yl)[4-(4-methyl-1H-imidazol-2-yl)piperidin-1-yl]methanone
(2'-Fluorobiphenyl-4-yl)[4-(4-methyl-1H-imidazol-2-yl)piperidin-1-yl]methanone
(2'-fluorobiphenyl-4-yl)[4-(4-phenyl-1H-imidazol-2-yl)piperidin-1-yl]methanone
(2'-Fluorobiphenyl-4-yl){4-[4-(trifluoromethyl)-1H-imidazol-2-yl]piperidin-1-yl}methanone
[4-(1H-benzimidazol-2-ylmethyl)piperidin-1-yl](2'-fluorobiphenyl-4-yl)methanone
(2'-fluorobiphenyl-4-yl)[4-(1H-imidazol-2-ylmethyl)piperidin-1-yl]methanone
(2'-fluorobiphenyl-4-yl){4-[(4-methyl-1H-imidazol-2-yl)methyl]piperidin-1-yl}methanone
biphenyl-4-yl{4-[(4-methyl-1H-imidazol-2-yl)methyl]piperidin-1-yl}methanone
biphenyl-4-yl(4-{[4-(trifluoromethyl)-1H-imidazol-2-yl]methyl}piperidin-1-yl)methanone
(2'-fluorobiphenyl-4-yl)(4-{[4-(trifluoromethyl)-1H-imidazol-2-yl]methyl}piperidin-1-yl)methanone
{4-[(5-fluoro-1H-benzimidazol-2-yl)methyl]piperidin-1-yl}(2'-fluorobiphenyl-4-yl)methanone
[4-(1H-benzimidazol-2-yl)piperidin-1-yl](6-phenylpyridin-3-yl)methanone
[4-(1H-benzimidazol-2-yl)piperidin-1-yl](5-phenylpyridin-2-yl)methanone
[4-(1H-benzimidazol-2-yl)piperidin-1-yl](3-methoxybiphenyl-4-yl)methanone
[4-(1H-benzimidazol-2-ylmethyl)piperidin-1-yl](3-methoxybiphenyl-4-yl)methanone

[4-(1H-benzimidazol-2-ylmethyl)piperidin-1-yl](2'-fluoro-3-methoxybiphenyl-4-yl)methanone
[4-(1H-imidazol-2-ylmethyl)piperidin-1-yl](3-methoxybiphenyl-4-yl)methanone
(2'-fluoro-3-methoxybiphenyl-4-yl)[4-(1H-imidazol-2-ylmethyl)piperidin-1-yl]methanone
{4-[(5-fluoro-1H-benzimidazol-2-yl)methyl]piperidin-1-yl}(3-methoxybiphenyl-4-yl)methanone
{4-[(5-fluoro-1H-benzimidazol-2-yl)methyl]piperidin-1-yl}(2'-fluoro-3-methoxybiphenyl-4-yl)methanone
2-[1-(biphenyl-4-ylsulfonyl)piperidin-4-yl]-1H-benzimidazole
2-{1-[(6-phenoxypyridin-3-yl)sulfonyl]piperidin-4-yl}-1H-benzimidazole
2-[1-(biphenyl-4-ylsulfonyl)azetidin-3-yl]-1H-benzimidazole
2-{1-[(2'-methoxybiphenyl-4-yl)sulfonyl]azetidin-3-yl}-1H-benzimidazole
1-(biphenyl-4-ylsulfonyl)-4-(1H-imidazol-2-yl)piperidine
2-{1-[(4'-fluorobiphenyl-4-yl)sulfonyl]azetidin-3-yl}-1H-benzimidazole
1-(biphenyl-4-ylsulfonyl)-4-(1H-imidazol-2-ylmethyl)piperidine
1-[(4'-fluorobiphenyl-4-yl)sulfonyl]-4-(1H-imidazol-2-yl)piperidine
[4-(1H-benzimidazol-2-yl)piperidin-1-yl][4-(5-ethyl-1,2,4-oxadiazol-3-yl)phenyl]methanone
[4-(1H-benzimidazol-2-yl)piperidin-1-yl][4-(5-cyclopropyl-1,2,4-oxadiazol-3-yl)phenyl]methanone
2-(1-{[4-(pyridin-2-yl)phenyl]sulfonyl}piperidin-4-yl)-1H-benzimidazole
2-(4-{[4-(1H-imidazol-2-yl)piperidin-1-yl]sulfonyl}phenyl)pyridine
2-{[1-(biphenyl-4-ylcarbonyl)piperidin-4-yl]methyl}-1H-imidazole-4-carbonitrile
2-({1-[(2'-fluorobiphenyl-4-yl)carbonyl]piperidin-4-yl}methyl)-1H-imidazole-4-carbonitrile,
or a pharmaceutically acceptable salt thereof.

In all the compounds disclosed hereinabove in this application, in the event the nomenclature is in conflict with the structure, it shall be understood that the compound is defined by the structure.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example benzoxazolyl, benzothiazolyl, benzimidazolyl, tetrahydropyranyl, dioxanyl, tetrahydrofuranyl, oxadiazolyl, oxazolyl, isoxazolyl, thiazolyl, pyrazolyl, pyrrolyl, imidazolyl, thienyl, thiadiazolyl, triazolyl, thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, isoquinolinyl, quinazolinyl, indazolyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle preferably phenyl or naphthyl.

Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The compounds of the invention may be prepared by the methods described below. In each of the schemes below, the groups $R^1$ to $R^3$, A, B, C and D are as defined above for general formula I unless noted otherwise. Optimum reaction conditions and reaction times may vary depending on the particular reactants used. Unless otherwise specified, solvents, temperatures, pressures and other reaction conditions may be readily selected by one of ordinary skill in the art. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety). Specific procedures are provided in the Synthetic Examples section. Typically, reaction progress may be monitored by thin layer chromatography (TLC) or HPLC-MS if desired. Intermediates and products may be purified by chromatography on silica gel, recrystallization, HPLC and/or reverse phase HPLC.

Starting materials and reagents are either commercially available or may be prepared by one skilled in the art using methods described in the chemical literature. Initial products of formula I may be modified further by methods known in the art to produce additional compounds of formula I.

Compounds of formula I may be prepared as illustrated in Scheme 1

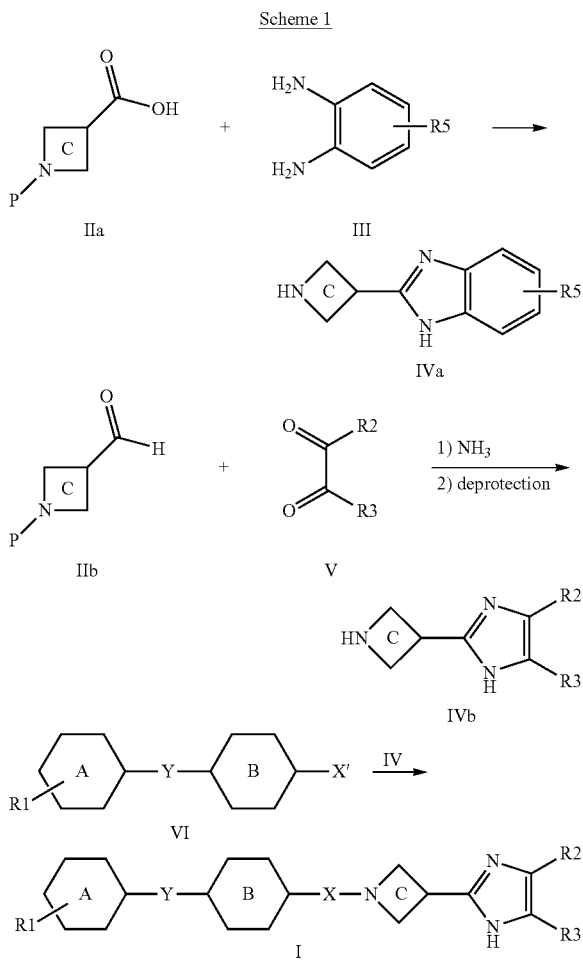

As illustrated above, intermediate IIa, where P=H and n=0-2 may be reacted with an optionally substituted 1,2-diaminobenzene III in refluxing 4 N HCl to provide IVa ($R_2$ and $R_3$ form a fused carbocyclic ring). Alternatively, if P is a protecting group such as a t-Boc group, II may be reacted with III in refluxing pyridine in the presence of triphenyl phosphine, followed by removal of the protecting group, for example by treatment with acid if P is a t-Boc group, to provide IVa. Imidazole intermediate IVb ($R_2$ and $R_3$ does not form a fused carbocyclic ring) may be prepared by reaction of intermediate IIb with ammonia and a 1,2-dicarbonyl compound V.

Reaction of intermediate VI having X'=CO₂H with the desired intermediate IV (a or b) under peptide coupling conditions well known in the art provides the compound of formula I having X=C=O. Reacting intermediate V having X'=SO₂Cl with the desired intermediate IV in a suitable solvent such as methylene chloride, in the presence of a suitable base such as diisopropylethylamine, provides the compound of formula I having X=SO₂.

An alternate approach to compounds of formula I is illustrated in Scheme 2.

Scheme 2

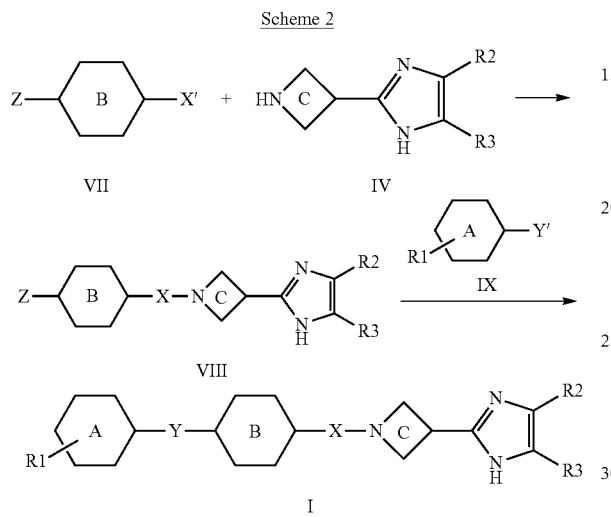

As illustrated above, the B ring is combined with intermediate IV first and then ring A is added in a separate step. For example, intermediate VII having B=aryl or heteroaryl, X'=CO₂H and Z=B(OH)₂, may be reacted with intermediate IV under standard coupling conditions to provide VIII (X=C=O). Intermediate VIII may then be reacted with IX under Suzuki coupling conditions, where A is an aryl or heteroaryl ring and Y' is a Br or other group capable of undergoing Suzuki coupling such as Cl, I or a triflate group to provide the compound of formula I where Y is a bond and A is aryl or heteroaryl and B is phenyl. Specific examples of the methods illustrated above as well as additional variations are illustrated in the synthetic examples below.

Preparation of Intermediates

Method A

Synthesis of 2-(Piperidin-4-yl)-1H-benzimidazole

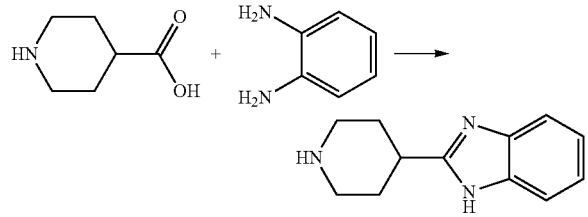

This compound is synthesized as described by adaptation of the following reference: *J. Heterocyclic Chem.,* 1989, 26, 54. A mixture of benzene-1,2-diamine (12.6 g, 116 mmol), piperidine-4-carboxylic acid (15 g, 116 mmol) and 4M aqueous HCl (250 mL) is stirred and heated under reflux for 48 h. The reaction mixture is cooled to room temperature and is made basic by addition of 5M aqueous NaOH. The precipitate formed is collected by suction filtration, washed with water and dried in the vacuum oven to afford 8.8 g (38%) of 2-(piperidin-4-yl)-1H-benzimidazole. m/z=202 [M⁺+H].

Method B

Synthesis of 5-Fluoro-2-piperidine-4-yl-1H-1,3-benzodiazole hydrochloride salt

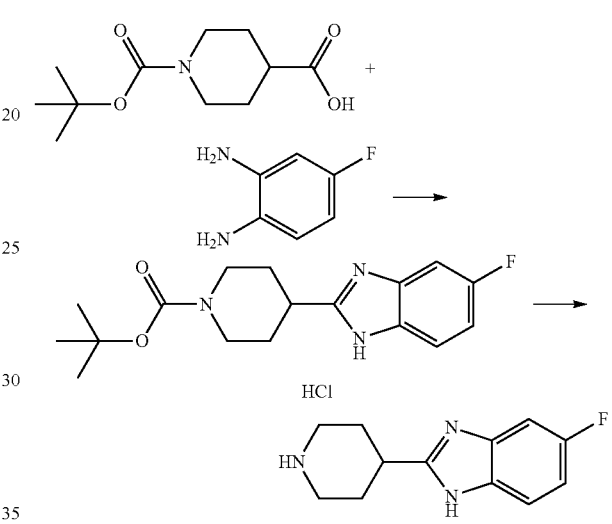

Step 1: Synthesis of tert-butyl-4-(5-fluoro-1H-1,3-benzodiazol-2-yl)piperidine-1-carboxylate This compound is synthesized as described by adaptation of the following reference: Lin et al, *Tetrahedron Lett.,* 2006, 47, 17, 2883. To a stirred mixture of 4-fluorobenzene-1,2-diamine (1.0 g, 7.93 mmol) and 1-[(tert-butoxy)carbonyl]piperidine-4-carboxylic acid (1.82 g, 7.93 mmol) in pyridine (4 mL) is added triphenyl phosphite (2.49 mL, 9.51 mmol). The reaction mixture is heated under reflux for 18 h. The reaction mixture is cooled to room temperature and diluted with EtOAc (40 mL). The solution is washed with 1M aqueous HCl (8 mL) followed by saturated aqueous NaHCO₃ (8 mL) and water (5 mL) to give an oily residue. The crude product is purified by column chromatography (Isolute column, eluent: DCM, 3% MeOH) to afford 0.81 g of tert-butyl-4-(5-fluoro-1H-1,3-benzodiazol-2-yl)piperidine-1-carboxylate.

TABLE 1

Benizimidazoles prepared via Method B step 1

| Compound | Yield (%) | m/z [M⁺ + H] |
|---|---|---|
| tert-Butyl 4-(5-fluoro-1H-benzimidazol-2-yl)piperidine-1-carboxylate | 32 | 320 |
| tert-Butyl 4-(5,6-difluoro-1H-benzimidazol-2-yl)piperidine-1-carboxylate | 5 | 338 |

TABLE 1-continued

Benizimidazoles prepared via Method B step 1

| Compound | Yield (%) | m/z [M+ + H] |
|---|---|---|
| tert-Butyl (3R)-3-(1H-benzimidazol-2-yl)piperidine-1-carboxylate | 68 | 302 |
| tert-Butyl (3S)-3-(1H-benzimidazol-2-yl)piperidine-1-carboxylate | 53 | 302 |
| tert-Butyl 4-(1H-benzimidazol-2-yl)-4-methylpiperidine-1-carboxylate | not isolated | 316 |
| tert-Butyl 4-(1H-benzimidazol-2-ylmethyl)piperidine-1-carboxylate | 50 | 316 |
| tert-Butyl 4-[(5-fluoro-1H-benzimidazol-2-yl)methyl]piperidine-1-carboxylate | 37 | 334 |
| tert-Butyl 3-(1H-benzimidazol-2-yl)pyrrolidine-1-carboxylate | 33 | 288 |
| tert-Butyl (2S)-2-(1H-benzimidazol-2-yl)pyrrolidine-1-carboxylate | 31 | 288 |
| tert-Butyl (2R)-2-(1H-benzimidazol-2-yl)pyrrolidine-1-carboxylate | 47 | 288 |
| tert-Butyl 3-(1H-benzimidazol-2-yl)azetidine-1-carboxylate | 21 | 274 |

Step 2: Synthesis of 5-Fluoro-2-(piperidin-4-yl)-1H-benzimidazole

To a stirred solution of tert-butyl 4-(5-fluoro-1H-benzimidazol-2-yl)piperidine-1-carboxylate (0.81 g, 2.53 mmol) in DCM (8 mL) is added a solution of 4M HCl in dioxane (2 mL). The reaction mixture is stirred at room temperature for 18 h. The reaction mixture is concentrated under reduced pressure to give 0.74 g of 5-fluoro-2-(piperidin-4-yl)-1H-benzimidazole. This product is used in the next step without further purification.

TABLE 2

Compounds prepared via variations of Method B step 2 by using acids such as 4M HCl in dioxane, 50% TFA in $CH_2Cl_2$, and $BF_3 \cdot OEt_2$.

| Compound | Yield (%) | m/z [M+ + H] |
|---|---|---|
| 5-Fluoro-2-(piperidin-4-yl)-1H-benzimidazole dihydrochloride | 88 | 220 |
| 5,6-Difluoro-2-(piperidin-4-yl)-1H-benzimidazole dihydrochloride | 94 | 238 |
| 2-[(3R)-Piperidin-3-yl]-1H-benzimidazole dihydrochloride | Not isolated. Used crude | 202 |
| 2-[(3S)-Piperidin-3-yl]-1H-benzimidazole dihydrochloride | Not isolated. Used crude | 202 |
| 2-(4-Methylpiperidin-4-yl)-1H-benzimidazole | Not isolated. Used crude | 216 |
| 2-(Piperidin-4-ylmethyl)-1H-benzimidazole dihydrochloride | Not isolated. Used crude | 216 |
| 5-Fluoro-2-(piperidin-4-ylmethyl)-1H-benzimidazole dihydrochloride | Not isolated. Used crude | not available |
| 2-(Pyrrolidin-3-yl)-1H-benzimidazole ditrifluoroacetate | Not isolated. Used crude | 188 |
| 2-[(2S)-Pyrrolidin-2-yl]-1H-benzimidazole dihydrochloride | Not isolated. Used crude | 188 |
| 2-[(2R)-Pyrrolidin-2-yl]-1H-benzimidazole dihydrochloride | Not isolated. Used crude | 188 |

TABLE 2-continued

Compounds prepared via variations of Method B step 2 by using acids such as 4M HCl in dioxane, 50% TFA in $CH_2Cl_2$, and $BF_3 \cdot OEt_2$.

| Compound | Yield (%) | m/z [M+ + H] |
|---|---|---|
| 2-(Azetidin-3-yl)-1H-benzimidazole | Not isolated. Used crude | 174 |

Method C

Synthesis of 2-(Azetidin-3-yl)-1H-imidazole

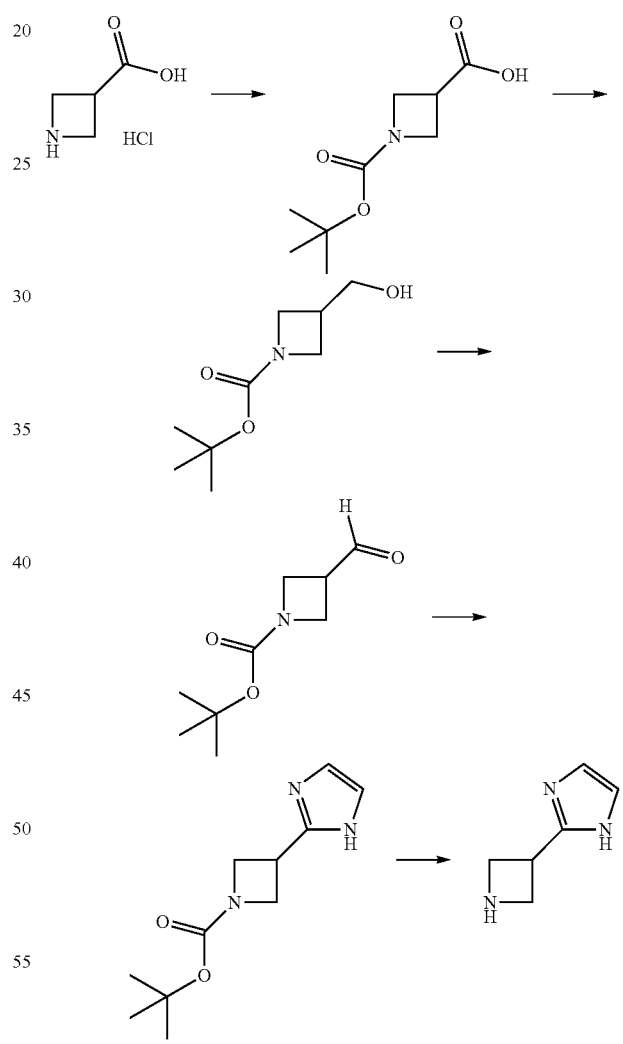

Step 1: Synthesis of 1-(tert-Butoxycarbonyl)azetidine-3-carboxylic acid

To a stirred solution of azetidine-3-carboxylic acid hydrochloride salt (1.0 g, 7.27 mmol) in DCM (35 mL) is added di-tert-butyl dicarbonate (1.74 g, 8.0 mmol) followed by triethylamine (2.2 mL, 16 mmol). Stirring is continued at room temperature for 18 h. Solvent is removed under reduced pressure. The residue is redissolved in EtOAc (50 mL), washed with saturated aqueous potassium hydrogen sulphate (10 mL) followed by water (20 mL), dried ($Na_2SO_4$), filtered and concentrated under reduced pressure to afford 1.0 g (58%) of 1-(tert-butoxycarbonyl)azetidine-3-carboxylic acid. m/z=146 [$M^+$+H-tBu], 187 [$M^+$+H-tBu+MeCN].

Step 2: Synthesis of tert-Butyl 3-(hydroxymethyl)azetidine-1-carboxylate

To a stirred suspension of sodium borohydride (1.92 g, 50.6 mmol) in dry THF (20 mL) is added a solution of 1-(tert-butoxycarbonyl)azetidine-3-carboxylic acid in dry THF (20 mL) at 0° C. A solution of iodine (4.71 g, 18.6 mmol) in THF (20 mL) is added dropwise (caution: gas evolution) under $N_2$ atmosphere. The reaction mixture is allowed to warm to room temperature then heated under reflux for 18 h. The resulting white suspension is cooled to room temperature. MeOH is added until the suspension dissolved. The mixture is concentrated under reduced pressure, then quenched with 1M aqueous KOH (100 mL) and extracted with DCM (3×150 mL). The organic phases are combined, washed with water followed by brine and concentrated under reduced pressure to give 2.13 g (27%) of tert-butyl 3-(hydroxymethyl)azetidine-1-carboxylate.

Step 3: Synthesis of tert-Butyl 3-formylazetidine-1-carboxylate

To a stirred solution of oxalyl chloride (4.28 mL, 4.98 mmol) in DCM (5 mL) at −78° C. is added DMSO (0.71 mL, 9.96 mL) dropwise. After stirring for 15 mins tert-butyl 3-(hydroxymethyl)azetidine-1-carboxylate (0.69 g, 3.69 mmol) is added followed immediately by triethylamine (2.1 mL, 14.75 mmol). The reaction mixture is allowed to warm to room temperature, diluted with DCM (30 mL), washed with water, dried ($Na_2SO_4$), filtered and concentrated under reduced pressure. The crude product is purified by column chromatography (Isolute column, eluent: heptane, 0-100% EtOAc) to give 0.19 g of tert-butyl 3-formylazetidine-1-carboxylate (27%).

Step 4: Synthesis of tert-Butyl 3-(1H-imidazol-2-yl)azetidine-1-carboxylate

This compound is synthesized as described by adaptation of the following reference: Rothenberg et al., *Angew. Chem. Int., Engl,* 1983, 22, 560. Ammonia gas was bubbled through a mixture of tert-butyl 3-formylazetidine-1-carboxylate (0.19 g, 1.01 mmol) and glyoxal (40% aqueous solution, 0.81 mL, 7.07 mmol) at 0° C. for 5 mins. The reaction mixture is allowed to warm to room temperature. The reaction mixture is concentrated under reduced pressure, diluted with EtOAc. The EtOAc solution is washed with brine and water, dried ($Na_2SO_4$), filtered and concentrated under reduced pressure. Purification by column chromatography (Isolute column, eluent DCM, 0-4% MeOH) gives 76.2 mg of tert-butyl 3-(1H-imidazol-2-yl)azetidine-1-carboxylate.

TABLE 3

Imidazoles prepared via Method C step 4.

| Compound | Yield (%) | m/z [$M^+$ + H] |
|---|---|---|
| tert-Butyl 3-(1H-imidazol-2-yl)azetidine-1-carboxylate | 34 | 168 [$M^+$ + H-tBu], 224 |
| tert-Butyl 4-(1H-imidazol-2-yl)piperidine-1-carboxylate | 31 | 252 |
| tert-Butyl 4-(1H-imidazol-2-ylmethyl)piperidine-1-carboxylate | 100 | 266 |
| tert-Butyl (2S)-2-(1H-imidazol-2-yl)pyrrolidine-1-carboxylate | 31 | 238 |
| tert-Butyl 4-(4-methyl-1H-imidazol-2-yl)piperidine-1-carboxylate | 75 | 266 |
| tert-Butyl 4-(4,5-dimethyl-1H-imidazol-2-yl)piperidine-1-carboxylate | 90 | 280 |
| tert-Butyl 4-[4-(trifluoromethyl)-1H-imidazol-2-yl]piperidine-1-carboxylate | 40 | 264 [$M^+$ +H-tBu], 342 [$M^+$ + Na] |
| tert-Butyl 4-(4-phenyl-1H-imidazol-2-yl)piperidine-1-carboxylate | 30 | 328 |
| tert-Butyl 4-[(4-methyl-1H-imidazol-2-yl)methyl]piperidine-1-carboxylate | 94 | 280 |
| tert-Butyl 4-{[4-(trifluoromethyl)-1H-imidazol-2-yl]methyl}piperidine-1-carboxylate | 97 | 278 [$M^+$ + H-tBu], 356 [$M^+$ + Na] |

Step 5: Synthesis of 2-(Azetidin-3-yl)-1H-imidazole

To a stirred solution of tert-butyl 3-(1H-imidazol-2-yl)azetidine-1-carboxylate (36 mg, 0.16 mmol) in DCM (1 mL) is added boron trifluoride diethyl ether complex (40 μL, 0.318 mmol). After 2 h the reaction mixture is quenched with water (11 μL). MeOH is added and the reaction mixture is concentrated under reduced pressure to give crude 2-(azetidin-3-yl)-1H-imidazole.

TABLE 4

Compounds prepared via variations of Method C step 5 by using acids such as 4M HCl in dioxane, 50% TFA in $CH_2Cl_2$, and $BF_3 \cdot OEt_2$.

| Compound | Yield (%) | m/z [$M^+$ + H] |
|---|---|---|
| 4-(1H-Imidazol-2-yl)piperidine dihydrochloride | Not isolated. Used crude | 152 |
| 4-(1H-Imidazol-2-ylmethyl)piperidine | Not isolated. Used crude | 166 |
| 2-[(2S)-Pyrrolidin-2-yl]-1H-imidazole | Not isolated. Used crude | 138 |
| 4-(4-Methyl-1H-imidazol-2-yl)piperidine | Not isolated. Used crude | 166 |
| 4-(4,5-Dimethyl-1H-imidazol-2-yl)piperidine | Not isolated. Used crude | Not available |
| 4-[4-(Trifluoromethyl)-1H-imidazol-2-yl]piperidine | Not isolated. Used crude | Not available |
| 4-(4-Phenyl-1H-imidazol-2-yl)piperidine | Not isolated. Used crude | Not available |

TABLE 4-continued

Compounds prepared via variations of Method C step 5 by using acids such as 4M HCl in dioxane, 50% TFA in CH$_2$Cl$_2$, and BF$_3$·OEt$_2$.

| Compound | Yield (%) | m/z [M$^+$ + H] |
|---|---|---|
| 4-[(4-Methyl-1H-imidazol-2-yl)methyl]piperidine | Not isolated. Used crude | Not available |
| 4-{[4-(Trifluoromethyl)-1H-imidazol-2-yl]methyl}piperidine | Not isolated. Used crude | Not available |

Preparation of Examples in Table

Method D

Synthesis of [4-(1H-Benzimidazol-2-yl)piperidin-1-yl](biphenyl-4-yl)methanone

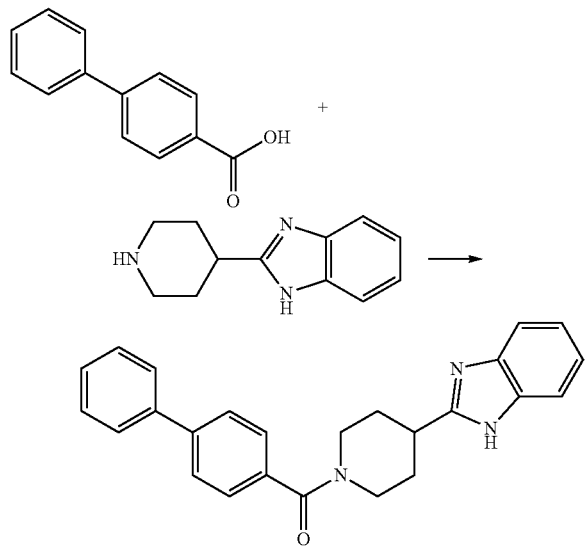

To a stirred mixture of 4-biphenyl carboxylic acid (10.0 g, 50.5 mmol) and 2-(piperidin-4-yl)-1H-benzimidazole (10.1 g, 50.5 mmol) in DCM (400 mL) is added 1-(3-dimethylaminopropyl)-3-ethylcarbodiimide hydrochloride (12.0 g, 62.7 mmol) and 4-dimethylaminopyridine (3.08 g, 25.2 mmol). After 3 h the reaction mixture is diluted with saturated aqueous NaHCO$_3$ (200 mL) and water (100 mL). The mixture is stirred for a few minutes. The organic layer is separated, washed with water, dried over Na$_2$SO$_4$, filtered and concentrated under reduced pressure. Trituration with EtOAc and further washing with EtOAc gives 14.1 g of [4-(1H-benzimidazol-2-yl)piperidin-1-yl](biphenyl-4-yl)methanone.

Examples listed in Table 6, Method D are made according to this procedure.

Method E

Synthesis of [4-(1H-Benzimidazol-2-yl)piperidin-1-yl](5-phenylpyridin-2-yl)methanone

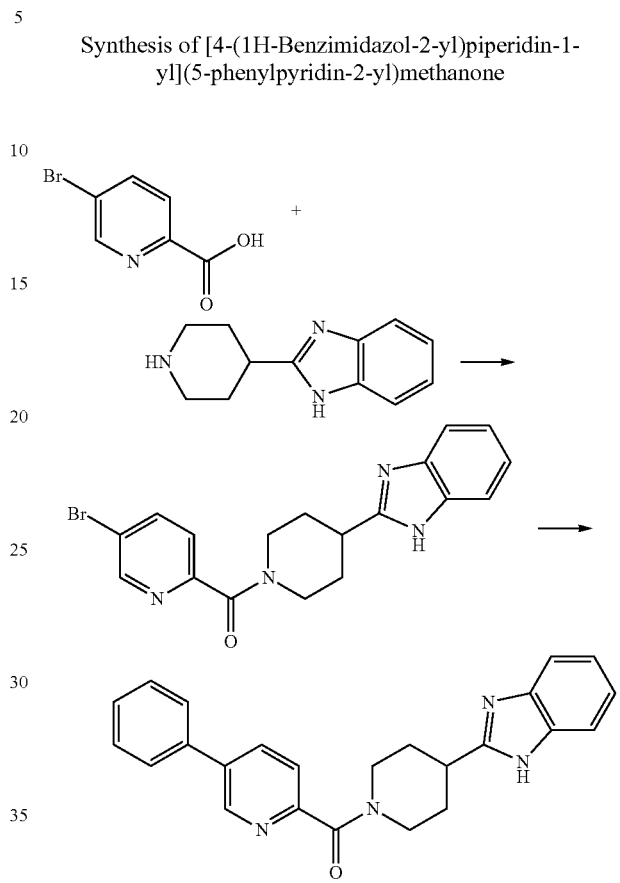

Step 1: Synthesis of [4-(1H-benzimidazol-2-yl)piperidin-1-yl](5-bromopyridin-2-yl)methanone To a stirred mixture of 5-bromopyridine-2-carboxylic acid (177 mg, 0.88 mmol) and 2-(piperidin-4-yl)-1H-benzimidazole dihydrochloride (200 mg, 0.73 mmol) in dichloroethane (5 mL) is added ethylcarbodiimide hydrochloride (168 mg, 0.88 mmol), triethylamine (0.25 mL, 1.82 mmol) and 4-dimethylaminopyridine (44.6 mg, 0.36 mmol). After 3 h the reaction mixture is washed with saturated aqueous NaHCO$_3$, water and brine. The organic layer is dried over Na$_2$SO$_4$, filtered and concentrated under reduced pressure. Trituration from hot EtOAc gives 39.4 mg of [4-(1H-benzimidazol-2-yl)piperidin-1-yl](5-bromopyridin-2-yl)methanone.

TABLE 5

Amides prepared via Method E step 1.

| Compound | Yield (%) | m/z [M$^+$ + H] |
|---|---|---|
| [4-(1H-Benzimidazol-2-yl)piperidin-1-yl](6-bromopyridin-3-yl)methanone | 20 | 385/387 |
| [4-(1H-Benzimidazol-2-yl)piperidin-1-yl](5-bromopyridin-2-yl)methanone | 14 | 385/387 |
| [4-(1H-Benzimidazol-2-yl)piperidin-1-yl](4-bromophenyl)methanone | 45 | 384/386 |

TABLE 5-continued

Amides prepared via Method E step 1.

| Compound | Yield (%) | m/z [M+ + H] |
|---|---|---|
| [4-(1H-Benzimidazol-2-yl)piperidin-1-yl](4-bromo-3-methylphenyl)methanone | 20 | 398/400 |
| [4-(1H-Benzimidazol-2-yl)piperidin-1-yl](4-bromo-2-methoxyphenyl)methanone | 42 | 414/416 |
| [3-(1H-Benzimidazol-2-yl)azetidin-1-yl](5-bromopyridin-2-yl)methanone | 65 | 357/359 |
| [3-(1H-Benzimidazol-2-yl)azetidin-1-yl](6-bromopyridin-3-yl)methanone | 61 | 357/359 |
| [4-(1H-Benzimidazol-2-ylmethyl)piperidin-1-yl](4-bromo-2-methoxyphenyl)methanone | Not isolated. Used crude | 428/430 |
| (4-Bromo-2-methoxyphenyl)[4-(1H-imidazol-2-ylmethyl)piperidin-1-yl]methanone | Not isolated. Used crude | 378/380 |
| (4-Bromo-2-methoxyphenyl){4-[(5-fluoro-1H-benzimidazol-2-yl)methyl]piperidin-1-yl}methanone | Not isolated. Used crude | 446/448 |

Step 2: Synthesis of [4-(1H-benzimidazol-2-yl)piperidin-1-yl](5-phenylpyridin-2-yl)methanone To a stirred mixture of [4-(1H-benzimidazol-2-yl)piperidin-1-yl](5-bromopyridin-2-yl)methanone (39 mg, 0.10 mmol) and phenylboronic acid (20.1 mg, 0.17 mmol) in a mixture of MeOH (0.5 mL) and 1,4-dioxane (1.5 mL) is added 2M aqueous NaHCO₃ (0.3 mL). The mixture is degassed with N₂. 1,1'-bis(diphenylphosphino)ferrocene-palladium (II) dichloride dichloromethane complex (5 mol %) is added and the mixture is heated at 100° C. under microwave irradiation for 30 mins. The mixture is filtered through a pad of celite and the filtrate is concentrated under reduced pressure. Purification by column chromatography (Isolute column, eluent DCM, 5% MeOH) affords 30.6 mg of [4-(1H-benzimidazol-2-yl)piperidin-1-yl](5-phenylpyridin-2-yl)methanone.

Examples listed in Table 6, Method E are made according to this procedure.

Method F

Synthesis of [4-(1H-Benzimidazol-2-yl)piperidin-1-yl][4-(pyrimidin-2-yl)phenyl]methanone

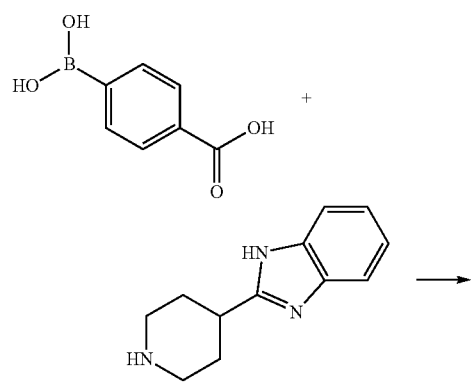

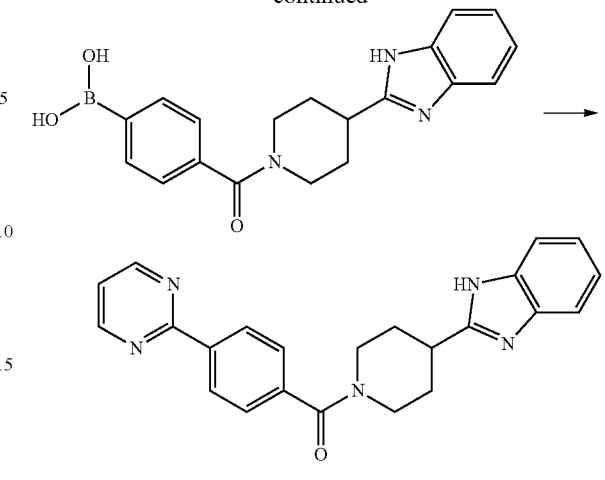

Step 1: Synthesis of (4-{[4-(1H-Benzimidazol-2-yl)piperidin-1-yl]carbonyl}phenyl)boronic acid This is synthesized according to the procedure described in Method D. Yield=80%. m/z=350 [M⁺+H].

Step 2: Synthesis of [4-(1H-Benzimidazol-2-yl)piperidin-1-yl][4-(pyrimidin-2-yl)phenyl]methanone A mixture of (4-{[4-(1H-benzimidazol-2-yl)piperidin-1-yl]carbonyl}phenyl)boronic acid (0.349 g, 1.00 mmol), 2-bromopyrimidine (0.175 g, 1.10 mmol) and sodium tert-butoxide (0.106 g, 1.10 mmol) are suspended in a mixture of MeOH/1,4-dioxane (1 mL/2 mL). The suspension is purged with N₂ before adding 1,1'-bis(diphenylphosphino)ferrocene-palladium (II) dichloride dichloromethane complex (41 mg, 5 mol %). The reaction is heated to 90° C. for 18 h. The mixture is diluted with EtOAc, washed with saturated aqueous NaHCO₃, dried over Na₂SO₄, filtered and concentrated under reduced pressure. The residue is triturated with MeCN and DCM to give 99 mg of [4-(1H-Benzimidazol-2-yl)piperidin-1-yl][4-(pyrimidin-2-yl)phenyl]methanone.

Examples listed in Table 6, Method F are made according to this procedure.

Method G

Synthesis of 2-[1-(biphenyl-4-ylsulfonyl)piperidin-4-yl]-1H-benzimidazole

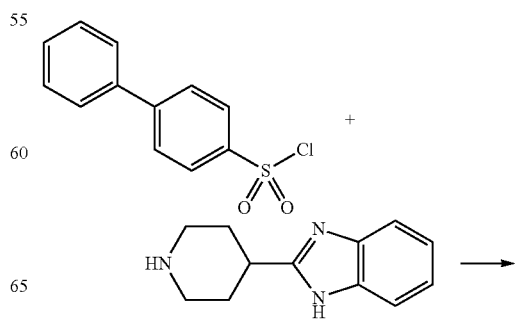

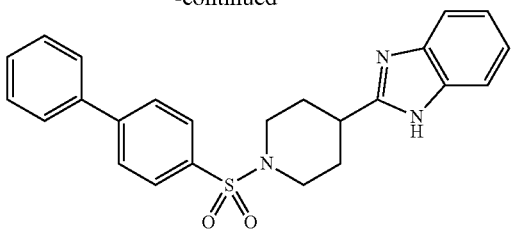

To a stirred mixture of 4-biphenylsulfonyl chloride (63 mg, 0.25 mmol) and 2-(piperidin-4-yl)-1H-benzimidazole (50 mg, 0.25 mmol) in DCM (10 mL) is added N,N-diisopropylethylamine (62 µL, 0.37 mmol). After 18 h the reaction mixture is washed with water and brine, dried over Na₂SO₄, filtered and concentrated under reduced pressure. Trituration with heptane gives 21 mg of 2-[1-(biphenyl-4-ylsulfonyl)piperidin-4-yl]-1H-benzimidazole.

Examples listed in Table 6, Method G are made according to this procedure.

Method H

Synthesis of [4-(1H-benzimidazol-2-yl)piperidin-1-yl](2,3'-bipyridin-6'-yl)methanone

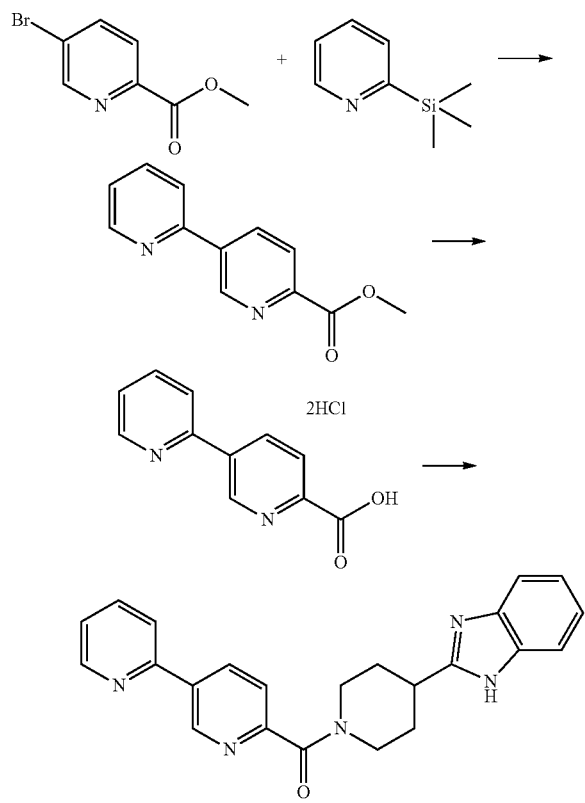

Step 1: Synthesis of Methyl 2,3'-bipyridine-6'-carboxylate

This compound is synthesized as described by adaptation of the following reference: Tye et al., *Tet. Lett.*, 2008, 49, 3939. To a stirred suspension of methyl-5-bromo-2-pyridine carboxylate (0.25 g, 1.16 mmol) and 2-(trimethylsilyl)pyridine (0.48 mL), 3.48 mmol) in anhydrous N,N-dimethyl formamide (7.5 mL) is added silver (I) oxide (0.27 g, 1.16 mmol), allyl palladium chloride dimer (21 mg, 5 mol %) and tetrabutyl ammonium fluoride (1M in THF, 0.116 mL). The reaction is heated at 90° C. for 18 h. The reaction mixture is filtered and washed with EtOAc. The filtrate is concentrated under reduced pressure. Purification by column chromatography (silica, eluent DCM, 0-2% MeOH) gives 0.12 g (48%) of methyl 2,3'-bipyridine-6'-carboxylate. m/z=215 [M⁺+H].

Step 2: Synthesis of 2,3'-bipyridine-6'-carboxylic acid dihydrochloride

A stirred solution of methyl 2,3'-bipyridine-6'-carboxylate (0.103 g, 0.48 mmol) in 5M aqueous HCl (2.5 mL) is heated at 80° C. for 2 h. The reaction is concentrated under reduced pressure and azeotroped with MeOH to give crude 2,3'-bipyridine-6'-carboxylic acid dihydrochloride which is used in the next step without further purification. m/z=201 [M⁺+H].

Step 3: Synthesis of [4-(1H-Benzimidazol-2-yl)piperidin-1-yl](2,3'-bipyridin-6'-yl)methanone This compound is synthesized according to the procedure described in Method D. Examples listed in Table 6, Method H are made according to this procedure.

Method I

Synthesis of 2-(1-{[4-(5-methyl-1,2,4-oxadiazol-3-yl)phenyl]sulfonyl}piperidin-4-yl)-1H-benzimidazole

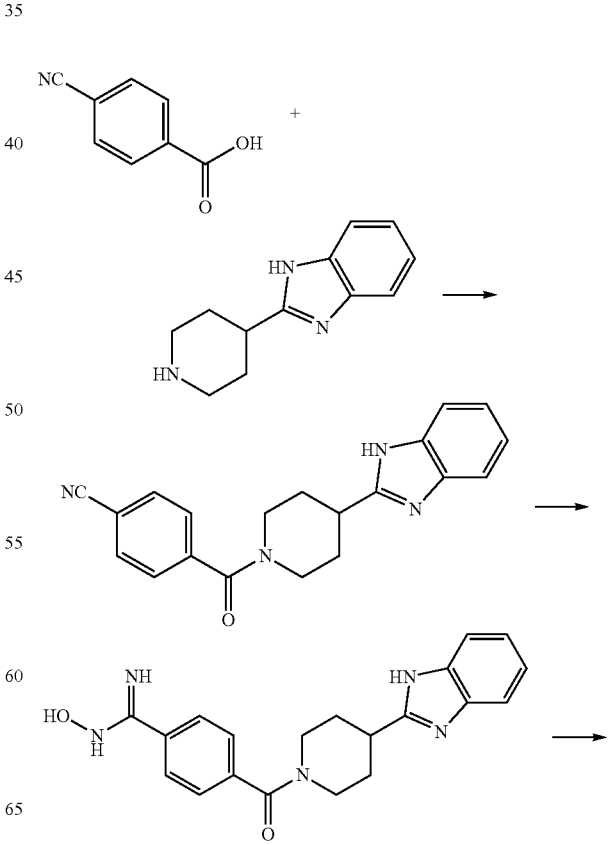

-continued

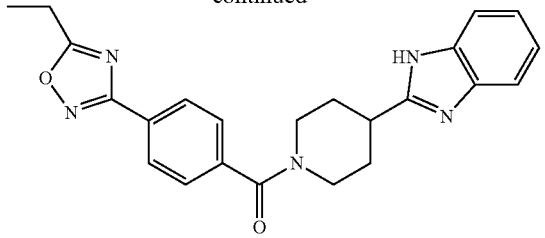

Step 1: Synthesis of 4-{[4-(1H-Benzimidazol-2-yl)
piperidin-1-yl]carbonyl}benzonitrile This compound is synthesized according to the procedure described in Method D. Yield=62%. m/z=331 [M$^+$+H].

Step 2: Synthesis of 4-{[4-(1H-Benzimidazol-2-yl)
piperidin-1-yl]carbonyl}-N-hydroxybenzene carboximidamide To a stirred suspension of 4-{[4-(1H-benzimidazol-2-yl)piperidin-1-yl]carbonyl}benzonitrile (0.30 g, 0.91 mmol) in ethanol (2 mL) is added 50% aqueous hydroxylamine (0.24 mL, 3.64 mmol). The reaction is heated at 80° C. for 18 h. The mixture is concentrated under reduced pressure to give 0.36 g (94%) of 4-{[4-(1H-benzimidazol-2-yl)piperidin-1-yl]carbonyl}-N-hydroxybenzene carboximidamide. m/z=364 [M$^+$+H].

Step 3: Synthesis of [4-(1H-Benzimidazol-2-yl)piperidin-1-yl][4-(5-ethyl-1,2,4-oxadiazol-3-yl)phenyl]methanone To a stirred solution of 4-{[4-(1H-benzimidazol-2-yl)piperidin-1-yl]carbonyl}-N-hydroxybenzene carboximidamide (0.15 g, 0.41 mmol) in anhydrous 1,4-dioxane (5 mL) is added dropwise propionyl chloride (34 μL, 0.39 mmol). The reaction is heated to 40° C. for 1 h before adding boron trifluoride etherate (10.5 μL, 0.083 mmol). Heating is continued at 80° C. for 4 h. The mixture is diluted with DCM and saturated aqueous NaHCO$_3$ giving a suspension which is filtered. The organic layer is separated, dried over Na$_2$SO$_4$, filtered and concentrated under reduced pressure to give 5 mg of [4-(1H-benzimidazol-2-yl)piperidin-1-yl][4-(5-ethyl-1,2,4-oxadiazol-3-yl)phenyl]methanone.

Examples listed in Table 6, Method I are made according to this procedure.

Method J

Synthesis of Biphenyl-4-yl[4-(1H-imidazo[4,5-c]pyridin-2-yl)piperidin-1-yl]methanone

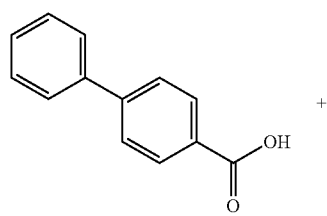

+

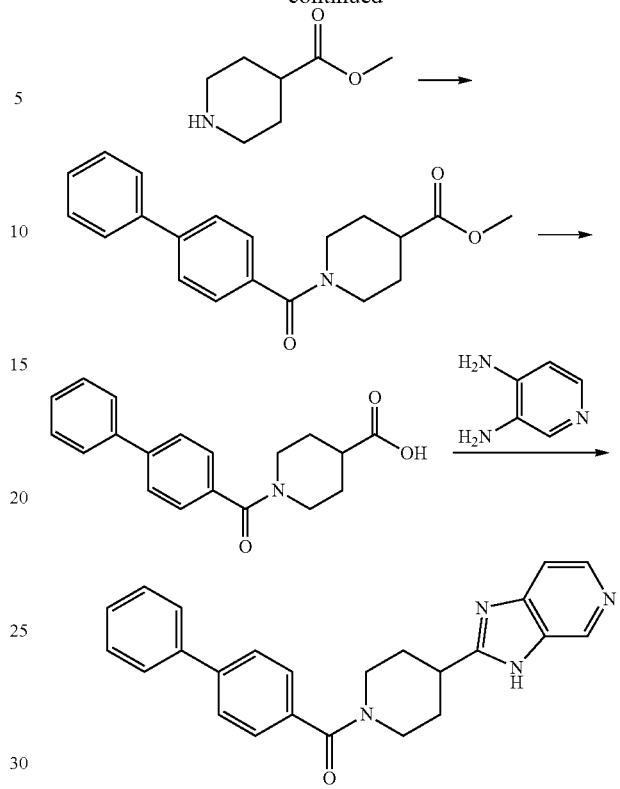

Step 1: Synthesis of Methyl
1-(biphenyl-4-ylcarbonyl)piperidine-4-carboxylate

This compound is synthesized according to the procedure described in Method D. Yield=70%. m/z=324 [M$^+$+H].

Step 2: Synthesis of
1-(Biphenyl-4-ylcarbonyl)piperidine-4-carboxylic acid

A stirred mixture of methyl 1-(biphenyl-4-ylcarbonyl)piperidine-4-carboxylate (0.10 g, 0.31 mmol), sodium hydroxide (25 mg, 0.62 mmol), water (4 mL) and tetrahydrofuran (1 mL) is heated at 50° C. for 3 h. Solvents are removed under reduced pressure giving a residue. The residue is redissolved 1M aqueous HCl (4 mL) and extracted with EtOAc (3×4 mL). The organic layers are combined, dried (Na$_2$SO$_4$), filtered and concentrated under reduced pressure to give 82 mg (93%) of 1-(biphenyl-4-ylcarbonyl)piperidine-4-carboxylic acid. m/z=310 [M$^+$+H].

Step 3: Synthesis of Biphenyl-4-yl[4-(1H-imidazo[4,5-c]pyridin-2-yl)piperidin-1-yl]methanone To a mixture of 1-(biphenyl-4-ylcarbonyl)piperidine-4-carboxylic acid (0.10 g, 0.32 mmol) and 3,4-diaminopyridine (35 mg, 0.32 mmol) in pyridine (1 mL) is added triphenyl phosphate (0.10 mL, 0.38 mmol). The mixture is heated under microwave irradiation at 120° C. for 50 mins. Purification by preparative HPLC gives 34 mg of biphenyl-4-yl[4-(1H-imidazo[4,5-c]pyridin-2-yl)piperidin-1-yl]methanone.

Examples listed in Table 6, Method J are made according to this procedure.

Method K

Synthesis of Biphenyl-4-yl[4-(5-hydroxy-1H-benzimidazol-2-yl)piperidin-1-yl]methanone

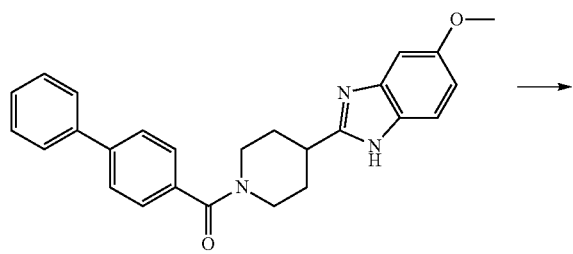

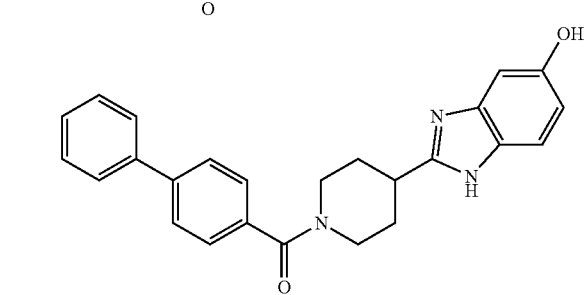

To a stirred solution of biphenyl-4-yl[4-(5-methoxy-1H-benzimidazol-2-yl)piperidin-1-yl]methanone (40 mg, 0.097 mmol) in DCM (1 mL) at −60° C. is added BBr (14 μL). After 30 mins the reaction mixture is warmed to room temperature, diluted with DCM and washed with water. The organic layer is concentrated under reduced pressure. Purification by preparative HPLC gives 6 mg of biphenyl-4-yl[4-(5-hydroxy-1H-benzimidazol-2-yl)piperidin-1-yl]methanone.

Examples listed in Table 6, Method K are made according to this procedure.

Method L

Synthesis of 2-[1-(Biphenyl-4-ylcarbonyl)piperidin-4-yl]-1H-benzimidazole-5-carboxylic acid

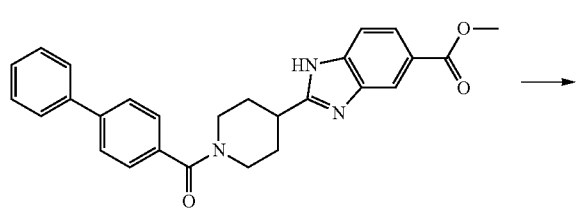

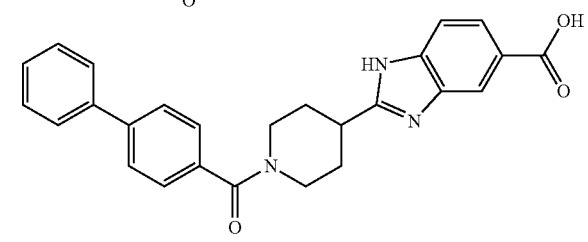

To a stirred solution of methyl 2-[1-(biphenyl-4-ylcarbonyl)piperidin-4-yl]-1H-benzimidazole-5-carboxylate (74 mg, 0.168 mmol) in THF (2 mL) is added 5M aqueous HCl (3 mL). The reaction is heated at 80° C. for 6 h. The mixture is concentrated under reduced pressure and the resulting residue is purified by preparative HPLC to give 4 mg of 2-[1-(biphenyl-4-ylcarbonyl)piperidin-4-yl]-1H-benzimidazole-5-carboxylic acid.

to Examples listed in Table 6, Method L are made according to this procedure.

Method M

Synthesis of 2-[1-(Biphenyl-4-ylcarbonyl)piperidin-4-yl]-N-methyl-1H-benzimidazole-5-carboxamide

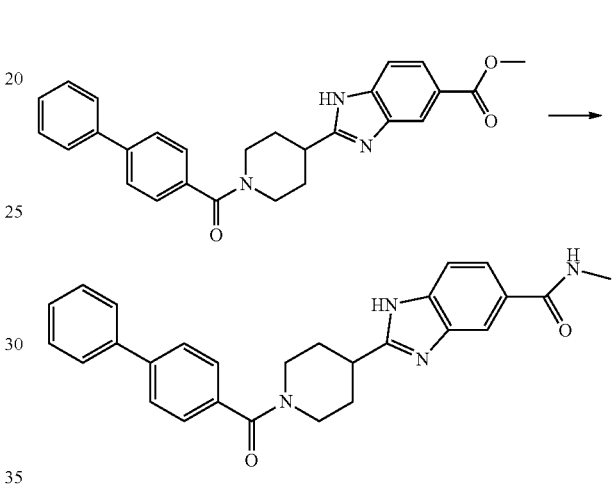

A solution of methyl 2-[1-(biphenyl-4-ylcarbonyl)piperidin-4-yl]-1H-benzimidazole-5-carboxylate (30 mg, 0.068 mmol) in 2M methylamine in EtOH (1 mL) is heated in at 50° C. for 18 h. The reaction is concentrated under reduced pressure and purified by preparative HPLC to give 13 mg of 2-[1-(biphenyl-4-ylcarbonyl)piperidin-4-yl]-N-methyl-1H-benzimidazole-5-carboxamide.

Examples listed in Table 6, Method M are made according to this procedure.

Method N

Synthesis of 2-(1-{[4-(Pyridin-2-yl)phenyl]sulfonyl}piperidin-4-yl)-1H-benzimidazole

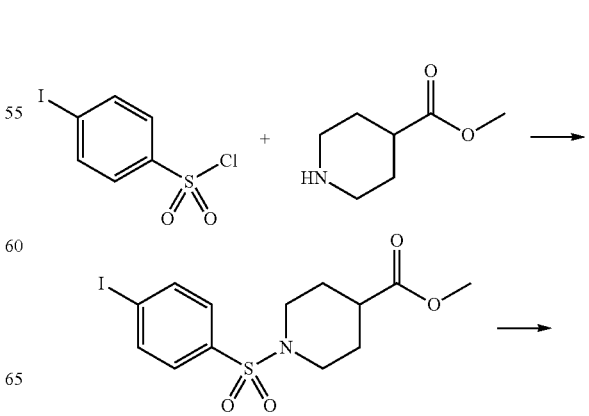

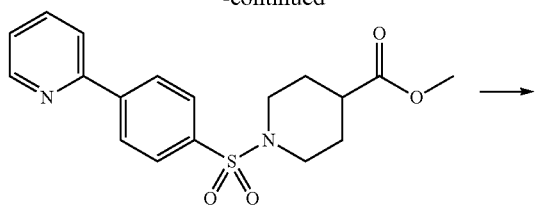

Step 1: Synthesis of Methyl 1-[(4-iodophenyl)sulfonyl]piperidine-4-carboxylate This compound is synthesized according to the procedure described in Method G. Yield=73%. m/z=410 [M⁺+H].

Step 2: Synthesis of Methyl 1-{[4-(pyridin-2-yl)phenyl]sulfonyl}piperidine-4-carboxylate To a stirred suspension of methyl 1-[(4-iodophenyl)sulfonyl]piperidine-4-carboxylate (1.97 g, 4.81 mmol) and 2-(trimethylsilyl)pyridine (2.0 mL), 14.5 mmol) in anhydrous N,N-dimethyl formamide (50 mL) is added silver (I) oxide (1.12 g, 4.82 mmol), tetrakis(triphenylphosphine)palladium (0.28 g, 5 mol %) and tetrabutyl ammonium fluoride (1M in THF, 0.48 mL). The reaction is heated at 90° C. for 18 h. The reaction mixture is filtered and washed with EtOAc. The filtrate is concentrated under reduced pressure. Purification by column chromatography (silica, eluent: heptane, 5-75% EtOAc) gives 0.87 g (50%) of methyl 1-{[4-(pyridin-2-yl)phenyl]sulfonyl}piperidine-4-carboxylate. m/z=361 [M⁺+H].

Step 3: Synthesis of 1-{[4-(Pyridin-2-yl)phenyl]sulfonyl}piperidine-4-carboxylic acid A stirred solution of methyl 1-{[4-(pyridin-2-yl)phenyl]sulfonyl}piperidine-4-carboxylate (0.25 g, 0.69 mmol) in 5M aqueous HCl (2.5 mL) is heated at 80° C. for 18 h. The mixture is cooled to room temperature resulting in formation of a precipitate. The precipitate is filtered, washed sequentially with 5M aqueous HCl and MeCN and dried in air to give 0.10 g (44%) of 1-{[4-(pyridin-2-yl)phenyl]sulfonyl}piperidine-4-carboxylic acid. m/z=347 [M⁺+H].

Step 4: Synthesis of 2-(1-{[4-(Pyridin-2-yl)phenyl]sulfonyl}piperidin-4-yl)-1H-benzimidazole This compound is synthesized according to the procedure described in Method J, Step 3. Examples listed in Table 6, Method N are made according to this procedure.

Method O

Synthesis of 2-(4-{[4-(1H-Imidazol-2-yl)piperidin-1-yl]sulfonyl}phenyl)pyridine

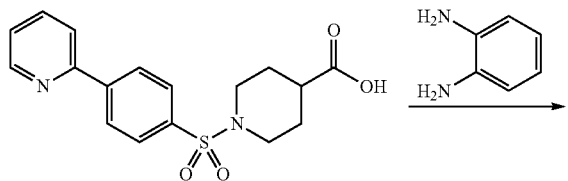

Step 1: Synthesis of (1-{[4-(Pyridin-2-yl)phenyl]sulfonyl}piperidin-4-yl)methanol To a stirred solution of methyl 1-{[4-(pyridin-2-yl)phenyl]sulfonyl}piperidine-4-carboxylate (0.40 g, 1.11 mmol) in anhydrous methanol (8 mL) is added sodium borohydride (0.59 g, 15.5 mmol). After 18 h water (20 mL) is added. The resulting solid is filtered, washed with water and suspended in MeCN. The suspension is concentrated under reduced pressure to give 0.26 g (72%) of 1-{[4-(pyridin-2-yl)phenyl]sulfonyl}piperidin-4-yl)methanol. m/z=333 [M⁺+H].

Step 2: Synthesis of 1-{[4-(Pyridin-2-yl)phenyl]sulfonyl}piperidine-4-carbaldehyde To a stirred solution of oxalyl chloride (92 μL, 1.07 mmol) in DCM (2 mL) at −78° C. is added dropwise a solution of dimethyl sulfoxide (0.15 mL, 2.16 mmol) in DCM (2 mL). After 15 mins a solution of (1-{[4-(pyridin-2-yl)phenyl]sulfonyl}piperidin-4-yl)methanol (0.26 g, 0.79 mmol) in DCM (2 mL) is added dropwise. After another 15 mins, triethylamine (0.425 mL, 3.04 mmol) is added and the reaction is allowed to warm to room temperature. Stirring is continued for 18 h. The mixture is diluted with water and extracted with DCM. The organic layers are combined, dried over $Na_2SO_4$, filtered and concentrated under reduced pressure to give 0.26 g (99%) of 1-{[4-(pyridin-2-yl)phenyl]sulfonyl}piperidine-4-carbaldehyde. m/z=331.

Step 3: Synthesis of 2-(4-{[4-(1H-Imidazol-2-yl)piperidin-1-yl]sulfonyl}phenyl)pyridine To a stirred solution of 1-{[4-(pyridin-2-yl)phenyl]sulfonyl}piperidine-4-carbaldehyde (0.26 g, 0.79 mmol) in MeOH (1 mL) is added 40% aqueous glyoxal (95 μL). The mixture is cooled at 0° C. and ammonia (7N in MeOH, 1.13 mL) is added. After stirring at room temperature for 18 h the mixture is concentrated under reduced pressure. The residue is redissolved in DCM and washed with saturated aqueous $NaHCO_3$. The organic layer is dried over $Na_2SO_4$, filtered and concentrated under reduced pressure to give the crude product. Trituration of the residue with EtOAc gives 0.114 g of 2-(4-{[4-(1H-Imidazol-2-yl)piperidin-1-yl]sulfonyl}phenyl)pyridine.

Examples listed in Table 6, Method O are made according to this procedure.

Method P

Synthesis of 2-(4-{[3-(1H-imidazol-2-yl)azetidin-1-yl]sulfonyl}phenyl)pyridine

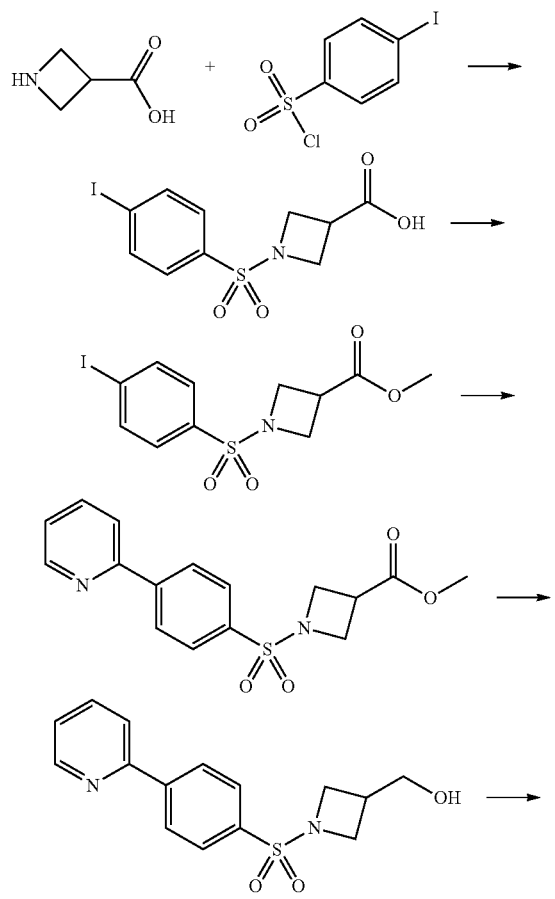

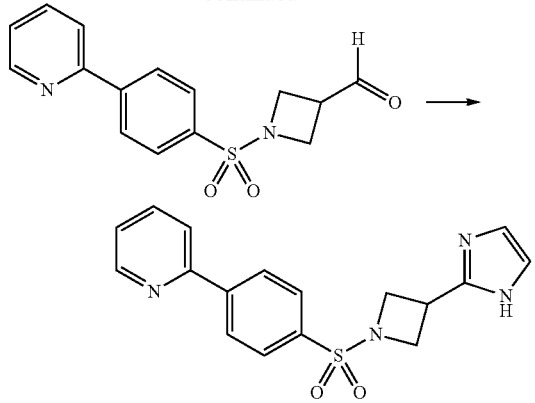

Step 1: Synthesis of 1-[(4-Iodophenyl)sulfonyl]azetidine-3-carboxylic acid

To a stirred solution of azetidine-3-carboxylic acid hydrochloride (1.0 g, 7.27 mmol) in DCM (25 mL) is added 5N aqueous NaOH (10 mL) and water (10 mL). p-Iodobenzenesulfonyl chloride (2.41 g, 7.98 mmol) is added portionwise. After 18 h the reaction mixture is diluted with DCM/water. The basic aqueous layer is acidified with 5N aqueous HCl. The resultant precipitate is filtered, washed with water and MeCN. Drying in air gives 1.17 g (44%) of 1-[(4-iodophenyl)sulfonyl]azetidine-3-carboxylic acid. m/z=368 [$M^++H$].

Step 2: Synthesis of Methyl 1-[(4-iodophenyl)sulfonyl]azetidine-3-carboxylate

To a stirred solution of 1-[(4-iodophenyl)sulfonyl]azetidine-3-carboxylic acid (0.75 g, 2.06 mmol) in THF (15 mL) is added triethylamine (0.43 mL, 3.09 mmol) followed by thionyl chloride (0.18 mL, 2.47 mmol). After stirring for 1 h, MeOH (10 mL) is added. Stirring is continued for another 1 h. The reaction mixture is concentrated under reduced pressure to give a residue which is taken up in EtOAc and washed with saturated aqueous $NaHCO_3$. The organic layer is dried over $Na_2SO_4$, filtered and concentrated under reduced pressure to give 0.60 g (77%) of methyl 1-[(4-iodophenyl)sulfonyl]azetidine-3-carboxylate. m/z=382 [$M^++H$].

Step 3: Synthesis of Methyl 1-{[4-(pyridin-2-yl)phenyl]sulfonyl}azetidine-3-carboxylate This is compound is synthesized as described by adaptation of the procedure described in Method N Step 2. Yield=62%. m/z=333 [$M^++H$].

Step 4: Synthesis of (1-{[4-(Pyridin-2-yl)phenyl]sulfonyl}azetidin-3-yl)methanol To a stirred solution of methyl 1-{[4-(pyridin-2-yl)phenyl]sulfonyl}azetidine-3-carboxylate (0.33 g, 0.99 mmol) in anhydrous methanol (20 mL) is added sodium borohydride (0.25 g, 6.58 mmol) portionwise. After 30 mins water (40 mL) is added followed by 5N aqueous NaOH. The aqueous layer is extracted with DCM. The organic layer is dried over $Na_2SO_4$, filtered and concentrated under reduced pressure to give 0.22 g (72%) of (1-{[4-(pyridin-2-yl)phenyl]sulfonyl}azetidin-3-yl)methanol. m/z=305 [$M^++H$].

Step 5: Synthesis of 1-{[4-(Pyridin-2-yl)phenyl]sulfonyl}azetidine-3-carbaldehyde This compound is synthesized as described by adaptation of the procedure described in Method C Step 3. Yield=100%. m/z=303 [M$^+$+H], 321 [M$^+$+H+H$_2$O].

Step 6: Synthesis of 2-(4-{[3-(1H-Imidazol-2-yl)azetidin-1-yl]sulfonyl}phenyl)pyridine This compound is synthesized as described by adaptation of the procedure described in Method C Step 4.

Examples listed in Table 6, Method Q are made according to this procedure.

Method Q

Synthesis of 2-({1-[(2'-fluorobiphenyl-4-yl)carbonyl]piperidin-4-yl}methyl)-1H-imidazole-4-carbonitrile

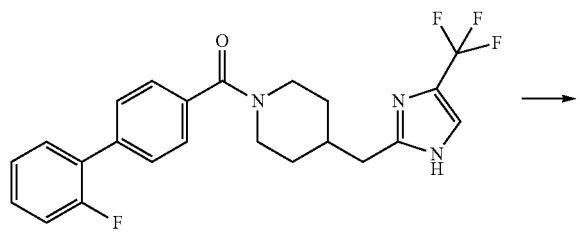

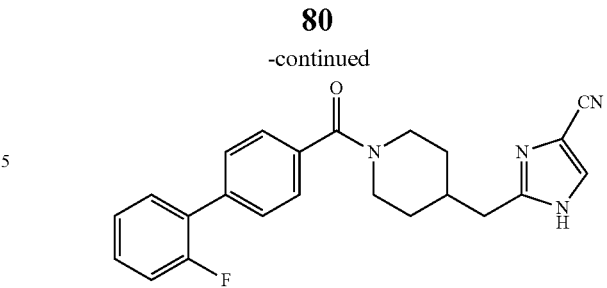

This compound is synthesized as described by adaptation of the following reference: Matthews et al, *J. Org. Chem.*, 1986, 51, 3228. To a stirred solution of (2'-fluorobiphenyl-4-yl)(4-{[4-(trifluoromethyl)-1H-imidazol-2-yl]methyl}piperidin-1-yl)methanone (0.114 g, 0.27 mmol) in MeCN (10 mL) is added hydroxylamine (5% aqueous solution, 40 mL). The reaction is heated at 60° C. for 4 h then allowed to cool to room temperature. The mixture is extracted with DCM and washed with saturated aqueous NaHCO$_3$. The organic layer is dried over Na$_2$SO$_4$, filtered and concentrated under reduced pressure to give the crude product. Purification by column chromatography (silica, eluent: DCM, 0-4% MeOH) gives 12.8 mg (12%) of 2-({1-[(2'-fluorobiphenyl-4-yl)carbonyl]piperidin-4-yl}methyl)-1H-imidazole-4-carbonitrile.

Examples listed in Table 6, Method Q are made according to this procedure.

TABLE 6

Examples prepared via the Methods described above.

| # | Name | m/z [M$^+$ + H] | Method |
|---|------|-----------------|--------|
| 1 | [4-(1H-Benzimidazol-2-yl)piperidin-1-yl](2'-chlorobiphenyl-4-yl)methanone | 416/418 | D |
| 2 | [4-(1H-Benzimidazol-2-yl)piperidin-1-yl](3'-chlorobiphenyl-4-yl)methanone | 416/418 | D |
| 3 | [4-(1H-Benzimidazol-2-yl)piperidin-1-yl](4'-chlorobiphenyl-4-yl)methanone | 416/418 | D |
| 4 | [4-(1H-Benzimidazol-2-yl)piperidin-1-yl](2'-fluorobiphenyl-4-yl)methanone | 400 | D |
| 5 | [4-(1H-Benzimidazol-2-yl)piperidin-1-yl](3'-fluorobiphenyl-4-yl)methanone | 400 | D |
| 6 | [4-(1H-Benzimidazol-2-yl)piperidin-1-yl](4'-fluorobiphenyl-4-yl)methanone | 400 | D |
| 7 | [4-(1H-Benzimidazol-2-yl)piperidin-1-yl][4-(pyridin-3-yl)phenyl]methanone | 383 | D |
| 8 | [4-(1H-Benzimidazol-2-yl)piperidin-1-yl][4-(pyridin-4-yl)phenyl]methanone | 383 | D |
| 9 | [4-(1H-Benzimidazol-2-yl)piperidin-1-yl](5-phenyl-2-thienyl)methanone | 388 | D |
| 10 | [4-(1H-Benzimidazol-2-yl)piperidin-1-yl][4-(2-thienyl)phenyl]methanone | 388 | D |
| 11 | Biphenyl-4-yl[4-(5-fluoro-1H-benzimidazol-2-yl)piperidin-1-yl]methanone | 400 | D |
| 12 | [4-(5-Fluoro-1H-benzimidazol-2-yl)piperidin-1-yl](4'-fluorobiphenyl-4-yl)methanone | 418 | D |
| 13 | Biphenyl-4-yl[4-(5,6-difluoro-1H-benzimidazol-2-yl)piperidin-1-yl]methanone | 418 | D |
| 14 | [4-(5,6-Difluoro-1H-benzimidazol-2-yl)piperidin-1-yl](4'-fluorobiphenyl-4-yl)methanone | 436 | D |
| 15 | [3-(1H-Benzimidazol-2-yl)azetidin-1-yl](biphenyl-4-yl)methanone | 354 | D |
| 16 | [4-(1H-Benzimidazol-2-yl)piperidin-1-yl][4-(5-methyl-1,2,4-oxadiazol-3-yl)phenyl]methanone | 388 | D |
| 17 | [4-(1H-Benzimidazol-2-yl)piperidin-1-yl](4-phenoxyphenyl)methanone | 398 | D |

TABLE 6-continued

Examples prepared via the Methods described above.

| # | Name | m/z [M+ + H] | Method |
|---|------|---------------|--------|
| 18 | [4-(1H-Benzimidazol-2-yl)piperidin-1-yl](4'-methoxybiphenyl-4-yl)methanone | 412 | D |
| 19 | [4-(1H-Benzimidazol-2-yl)piperidin-1-yl](3'-methoxybiphenyl-4-yl)methanone | 412 | D |
| 20 | [4-(1H-Benzimidazol-2-yl)piperidin-1-yl](2'-methoxybiphenyl-4-yl)methanone | 412 | D |
| 21 | [4-(1H-Benzimidazol-2-yl)piperidin-1-yl][4-(phenylsulfonyl)phenyl]methanone | 446 | D |
| 22 | [4-(1H-Benzimidazol-2-yl)piperidin-1-yl][4'-(2-methoxyethoxy)biphenyl-4-yl]methanone | 456 | D |
| 23 | [3-(1H-Benzimidazol-2-yl)piperidin-1-yl](biphenyl-4-yl)methanone | 382 | D |
| 24 | [4-(1H-Benzimidazol-2-yl)piperidin-1-yl][4-(pyridin-2-yl)phenyl]methanone | 383 | D |
| 25 | [4-(1H-Benzimidazol-2-yl)-4-methylpiperidin-1-yl](biphenyl-4-yl)methanone | 396 | D |
| 26 | [4-(1H-Benzimidazol-2-ylmethyl)piperidin-1-yl](biphenyl-4-yl)methanone | 396 | D |
| 27 | [4-(1H-Benzimidazol-2-yl)piperidin-1-yl](2-phenyl-1,3-thiazol-4-yl)methanone | 389 | D |
| 28 | [4-(1H-Benzimidazol-2-yl)piperidin-1-yl](4-ethoxy-2-phenylpyrimidin-5-yl)methanone | 428 | D |
| 29 | [4-(1H-Benzimidazol-2-yl)piperidin-1-yl][6-(3-methoxyphenyl)pyridin-3-yl]methanone | 413 | D |
| 30 | [4-(1H-Benzimidazol-2-yl)piperidin-1-yl](2-phenylpyrimidin-5-yl)methanone | 384 | D |
| 31 | [4-(1H-Benzimidazol-2-yl)piperidin-1-yl](4-phenyl-1,3-thiazol-2-yl)methanone | 389 | D |
| 32 | 3-{[4-(1H-Benzimidazol-2-yl)piperidin-1-yl]carbonyl}-6-phenylpyridin-2(1H)-one | 399 | D |
| 33 | [4-(1H-Benzimidazol-2-yl)piperidin-1-yl](1-phenyl-1H-pyrazol-4-yl)methanone | 372 | D |
| 34 | [4-(1H-Benzimidazol-2-yl)piperidin-1-yl](4-phenyl-2-thienyl)methanone | 388 | D |
| 35 | [4-(1H-Benzimidazol-2-yl)piperidin-1-yl](2-phenyl-1,3-thiazol-5-yl)methanone | 389 | D |
| 36 | [4-(1H-Benzimidazol-2-yl)piperidin-1-yl](2',4'-dimethoxybiphenyl-4-yl)methanone | 442 | D |
| 37 | [4-(1H-Benzimidazol-2-yl)piperidin-1-yl][4'-(trifluoromethoxy)biphenyl-4-yl]methanone | 466 | D |
| 38 | [4-(1H-Benzimidazol-2-yl)piperidin-1-yl][4-(4-fluorophenoxy)phenyl]methanone | 416 | D |
| 39 | Biphenyl-4-yl[4-(1H-imidazol-2-yl)piperidin-1-yl]methanone | 332 | D |
| 40 | [4-(1H-Benzimidazol-2-yl)piperidin-1-yl](5-phenyl-1,2,4-oxadiazol-3-yl)methanone | 374 | D |
| 41 | [4-(1H-Benzimidazol-2-yl)piperidin-1-yl](3',4'-dimethoxybiphenyl-4-yl)methanone | 442 | D |
| 42 | [3-(1H-Benzimidazol-2-yl)azetidin-1-yl][4-(5-methyl-1,2,4-oxadiazol-3-yl)phenyl]methanone | 360 | D |
| 43 | [(2S)-2-(1H-Benzimidazol-2-yl)pyrrolidin-1-yl](biphenyl-4-yl)methanone | 368 | D |
| 44 | [3-(1H-Benzimidazol-2-yl)pyrrolidin-1-yl](biphenyl-4-yl)methanone | 368 | D |
| 45 | [3-(1H-Benzimidazol-2-yl)azetidin-1-yl](2'-methoxybiphenyl-4-yl)methanone | 384 | D |
| 46 | [3-(1H-Benzimidazol-2-yl)azetidin-1-yl](4-phenoxyphenyl)methanone | 370 | D |
| 47 | [3-(1H-Benzimidazol-2-yl)azetidin-1-yl](4-ethoxy-2-phenylpyrimidin-5-yl)methanone | 400 | D |
| 48 | [3-(1H-Benzimidazol-2-yl)azetidin-1-yl][4-(4-fluorophenoxy)phenyl]methanone | 388 | D |
| 49 | [(3S)-3-(1H-Benzimidazol-2-yl)piperidin-1-yl](biphenyl-4-yl)methanone | 382 | D |
| 50 | [(3R)-3-(1H-Benzimidazol-2-yl)piperidin-1-yl](biphenyl-4-yl)methanone | 382 | D |
| 51 | [(2R)-2-(1H-Benzimidazol-2-yl)pyrrolidin-1-yl](biphenyl-4-yl)methanone | 368 | D |
| 52 | [3-(1H-Benzimidazol-2-yl)azetidin-1-yl](2-phenylpyrimidin-5-yl)methanone | 356 | D |
| 53 | [3-(1H-Benzimidazol-2-yl)azetidin-1-yl][4-(pyridin-2-yl)phenyl]methanone | 178 [½M + H], 355 [M + H] | D |

TABLE 6-continued

Examples prepared via the Methods described above.

| # | Name | m/z [M+ + H] | Method |
|---|---|---|---|
| 54 | (4'-Fluorobiphenyl-4-yl)[4-(1H-imidazol-2-yl)piperidin-1-yl]methanone | 350 | D |
| 55 | [4-(1H-Imidazol-2-yl)piperidin-1-yl][4-(pyrimidin-2-yl)phenyl]methanone | 334 | D |
| 56 | [4-(1H-Imidazol-2-yl)piperidin-1-yl][4-(pyridin-2-yl)phenyl]methanone | 167 [½M + H], 333 [M + H] | D |
| 57 | [4-(1H-Benzimidazol-2-ylmethyl)piperidin-1-yl](4'-fluorobiphenyl-4-yl)methanone | 414 | D |
| 58 | [(2S)-2-(1H-Benzimidazol-2-yl)pyrrolidin-1-yl](4'-fluorobiphenyl-4-yl)methanone | 386 | D |
| 59 | [(2S)-2-(1H-Benzimidazol-2-yl)pyrrolidin-1-yl][4-(pyridin-2-yl)phenyl]methanone | 185 [½M + H], 369 [M + H] | D |
| 60 | [4-(1H-Benzimidazol-2-ylmethyl)piperidin-1-yl][4-(pyridin-2-yl)phenyl]methanone | 199 [½M + H], 397 [M + H] | D |
| 61 | Biphenyl-4-yl[(2S)-2-(1H-imidazol-2-yl)pyrrolidin-1-yl]methanone | 318 | D |
| 62 | Biphenyl-4-yl[3-(1H-imidazol-2-yl)azetidin-1-yl]methanone | 304 | D |
| 63 | Biphenyl-4-yl[4-(1H-imidazol-2-ylmethyl)piperidin-1-yl]methanone | 346 | D |
| 64 | (4'-Fluorobiphenyl-4-yl)[4-(1H-imidazol-2-ylmethyl)piperidin-1-yl]methanone | 364 | D |
| 65 | [4-(1H-Imidazol-2-ylmethyl)piperidin-1-yl][4-(pyridin-2-yl)phenyl]methanone | 174 [½M + H], 347 [M + H] | D |
| 66 | (4'-Fluorobiphenyl-4-yl)[(2S)-2-(1H-imidazol-2-yl)pyrrolidin-1-yl]methanone | 336 | D |
| 67 | Biphenyl-4-yl[4-(4-methyl-1H-imidazol-2-yl)piperidin-1-yl]methanone | 346 | D |
| 68 | (4'-Fluorobiphenyl-4-yl)[4-(4-phenyl-1H-imidazol-2-yl)piperidin-1-yl]methanone | 426 | D |
| 69 | [4-(4,5-Dimethyl-1H-imidazol-2-yl)piperidin-1-yl](4'-fluorobiphenyl-4-yl)methanone | 378 | D |
| 70 | (4'-Fluorobiphenyl-4-yl)[3-(1H-imidazol-2-yl)azetidin-1-yl]methanone | 322 | D |
| 71 | [4-(1H-Imidazol-2-yl)piperidin-1-yl](6-phenylpyridin-3-yl)methanone | 167 [½M + H], 333 [M + H] | D |
| 72 | (4-Ethoxy-2-phenylpyrimidin-5-yl)[4-(1H-imidazol-2-yl)piperidin-1-yl]methanone | 189 [½M + H], 378 [M + H] | D |
| 73 | (2'-Fluorobiphenyl-4-yl)[4-(1H-imidazol-2-yl)piperidin-1-yl]methanone | 350 | D |
| 74 | [4-(1H-Imidazol-2-yl)piperidin-1-yl](2'-methoxybiphenyl-4-yl)methanone | 362 | D |
| 75 | (3',4'-Dimethoxybiphenyl-4-yl)[4-(1H-imidazol-2-yl)piperidin-1-yl]methanone | 392 | D |
| 76 | (4'-Fluorobiphenyl-4-yl)[4-(4-methyl-1H-imidazol-2-yl)piperidin-1-yl]methanone | 364 | D |
| 77 | (2'-Fluorobiphenyl-4-yl)[4-(4-methyl-1H-imidazol-2-yl)piperidin-1-yl]methanone | 364 | D |
| 78 | (2'-Fluorobiphenyl-4-yl)[4-(4-phenyl-1H-imidazol-2-yl)piperidin-1-yl]methanone | 426 | D |
| 79 | (2'-Fluorobiphenyl-4-yl){4-[4-(trifluoromethyl)-1H-imidazol-2-yl]piperidin-1-yl}methanone | 418 [M + H], 835 [2M + H] | D |
| 80 | 4'-{[4-(1H-Imidazol-2-yl)piperidin-1-yl]carbonyl}biphenyl-4-carbonitrile | 357 | D |
| 81 | [4-(1H-Benzimidazol-2-ylmethyl)piperidin-1-yl](2'-fluorobiphenyl-4-yl)methanone | 414 | D |
| 82 | (2'-Fluorobiphenyl-4-yl)[4-(1H-imidazol-2-ylmethyl)piperidin-1-yl]methanone | 364 | D |
| 83 | (2'-Fluorobiphenyl-4-yl){4-[(4-methyl-1H-imidazol-2-yl)methyl]piperidin-1-yl}methanone | 378 | D |

TABLE 6-continued

Examples prepared via the Methods described above.

| # | Name | m/z [M⁺ + H] | Method |
|---|------|--------------|--------|
| 84 | Biphenyl-4-yl{4-[(4-methyl-1H-imidazol-2-yl)methyl]piperidin-1-yl}methanone | 360 | D |
| 85 | Biphenyl-4-yl(4-{[4-(trifluoromethyl)-1H-imidazol-2-yl]methyl}piperidin-1-yl)methanone | 414 [M + H], 827 [2M + H] | D |
| 86 | (2'-Fluorobiphenyl-4-yl)(4-{[4-(trifluoromethyl)-1H-imidazol-2-yl]methyl}piperidin-1-yl)methanone | 432 | D |
| 87 | {4-[(5-Fluoro-1H-benzimidazol-2-yl)methyl]piperidin-1-yl}(2'-fluorobiphenyl-4-yl)methanone | 432 | D |
| 88 | (4'-Fluorobiphenyl-4-yl)[2-(1H-imidazol-2-yl)pyrrolidin-1-yl]methanone | | D |
| 89 | [4-(1H-Benzimidazol-2-yl)piperidin-1-yl](6-phenylpyridin-3-yl)methanone | 383 | E |
| 90 | [4-(1H-Benzimidazol-2-yl)piperidin-1-yl](5-phenylpyridin-2-yl)methanone | 383 | E |
| 91 | 4'-{[4-(1H-Benzimidazol-2-yl)piperidin-1-yl]carbonyl}biphenyl-4-carboxamide | 425 | E |
| 92 | [4-(1H-Benzimidazol-2-yl)piperidin-1-yl](2-methylbiphenyl-4-yl)methanone | 396 | E |
| 93 | 4'-{[4-(1H-Benzimidazol-2-yl)piperidin-1-yl]carbonyl}biphenyl-3-carboxamide | 425 | E |
| 94 | 4'-{[4-(1H-Benzimidazol-2-yl)piperidin-1-yl]carbonyl}biphenyl-2-carboxamide | 425 | E |
| 95 | [4-(1H-Benzimidazol-2-yl)piperidin-1-yl][4-(pyrimidin-5-yl)phenyl]methanone | 384 | E |
| 96 | [4-(1H-Benzimidazol-2-yl)piperidin-1-yl][4-(1H-pyrazol-4-yl)phenyl]methanone | 372 | E |
| 97 | [4-(1H-Benzimidazol-2-yl)piperidin-1-yl][4-(3,5-dimethylisoxazol-4-yl)phenyl]methanone | 401 | E |
| 98 | [4-(1H-Benzimidazol-2-yl)piperidin-1-yl](3-methoxybiphenyl-4-yl)methanone | 412 | E |
| 99 | [3-(1H-Benzimidazol-2-yl)azetidin-1-yl](5-phenylpyridin-2-yl)methanone | 355 | E |
| 100 | [3-(1H-Benzimidazol-2-yl)azetidin-1-yl](6-phenylpyridin-3-yl)methanone | 355 | E |
| 101 | [4-(1H-Benzimidazol-2-ylmethyl)piperidin-1-yl](3-methoxybiphenyl-4-yl)methanone | 426 | E |
| 102 | [4-(1H-Benzimidazol-2-ylmethyl)piperidin-1-yl](2'-fluoro-3-methoxybiphenyl-4-yl)methanone | 444 | E |
| 103 | [4-(1H-Imidazol-2-ylmethyl)piperidin-1-yl](3-methoxybiphenyl-4-yl)methanone | 376 | E |
| 104 | (2'-Fluoro-3-methoxybiphenyl-4-yl)[4-(1H-imidazol-2-ylmethyl)piperidin-1-yl]methanone | 394 [M + H], 787 [2M + H] | E |
| 105 | {4-[(5-Fluoro-1H-benzimidazol-2-yl)methyl]piperidin-1-yl}(3-methoxybiphenyl-4-yl)methanone | 223 [½M + H], 444 [M + H] | E |
| 106 | {4-[(5-Fluoro-1H-benzimidazol-2-yl)methyl]piperidin-1-yl}(2'-fluoro-3-methoxybiphenyl-4-yl)methanone | 462 | E |
| 107 | [4-(1H-Benzimidazol-2-yl)piperidin-1-yl][4-(pyrimidin-2-yl)phenyl]methanone | 384 | F |
| 108 | 2-[1-(Biphenyl-4-ylsulfonyl)piperidin-4-yl]-1H-benzimidazole | 418 | G |
| 109 | 2-{1-[(6-Phenoxypyridin-3-yl)sulfonyl]piperidin-4-yl}-1H-benzimidazole | 435 | G |
| 110 | 2-[1-(Biphenyl-4-ylsulfonyl)azetidin-3-yl]-1H-benzimidazole | 390 | G |
| 111 | 2-{[1-(Biphenyl-4-ylsulfonyl)piperidin-4-yl]methyl}-1H-benzimidazole | 432 | G |
| 112 | 2-{1-[(2'-Methoxybiphenyl-4-yl)sulfonyl]azetidin-3-yl}-1H-benzimidazole | 420 | G |
| 113 | 1-(Biphenyl-4-ylsulfonyl)-4-(1H-imidazol-2-yl)piperidine | 368 | G |
| 114 | 2-[(2S)-1-(Biphenyl-4-ylsulfonyl)pyrrolidin-2-yl]-1H-benzimidazole | 404 | G |
| 115 | 2-{1-[(4'-Fluorobiphenyl-4-yl)sulfonyl]azetidin-3-yl}-1H-benzimidazole | 408 | G |
| 116 | 2-[(2S)-1-(Biphenyl-4-ylsulfonyl)pyrrolidin-2-yl]-1H-imidazole | 354 | G |

TABLE 6-continued

Examples prepared via the Methods described above.

| # | Name | m/z [M$^+$ + H] | Method |
|---|------|-----------------|--------|
| 117 | 1-(Biphenyl-4-ylsulfonyl)-4-(1H-imidazol-2-ylmethyl)piperidine | 382 | G |
| 118 | 1-[(4'-Fluorobiphenyl-4-yl)sulfonyl]-4-(1H-imidazol-2-yl)piperidine | 386 | G |
| 119 | 2-{(2S)1-[(4'-Fluorobiphenyl-4-yl)sulfonyl]pyrrolidin-2-yl}-1H-imidazole | 372 | G |
| 120 | [4-(1H-Benzimidazol-2-yl)piperidin-1-yl](2,3'-bipyridin-6'-yl)methanone | 384 | H |
| 121 | [4-(1H-Benzimidazol-2-yl)piperidin-1-yl][4-(5-ethyl-1,2,4-oxadiazol-3-yl)phenyl]methanone | 402 | I |
| 122 | [4-(1H-Benzimidazol-2-yl)piperidin-1-yl][4-(5-cyclopropyl-1,2,4-oxadiazol-3-yl)phenyl]methanone | 414 | I |
| 123 | 2-(1-{[4-(5-Methyl-1,2,4-oxadiazol-3-yl)phenyl]sulfonyl}piperidin-4-yl)-1H-benzimidazole | 424 | I |
| 124 | Methyl 2-[1-(biphenyl-4-ylcarbonyl)piperidin-4-yl]-1H-benzimidazole-5-carboxylate | 400 | J |
| 125 | Biphenyl-4-yl[4-(1H-imidazo[4,5-c]pyridin-2-yl)piperidin-1-yl]methanone | 383 | J |
| 126 | Biphenyl-4-yl[4-(1H-imidazo[4,5-b]pyridin-2-yl)piperidin-1-yl]methanone | 383 | J |
| 127 | Biphenyl-4-yl[4-(5-methoxy-1H-benzimidazol-2-yl)piperidin-1-yl]methanone | 412 | J |
| 128 | Biphenyl-4-yl[4-(5-hydroxy-1H-benzimidazol-2-yl)piperidin-1-yl]methanone | 398 | K |
| 129 | 2-[1-(Biphenyl-4-ylcarbonyl)piperidin-4-yl]-1H-benzimidazole-5-carboxylic acid | 426 | L |
| 130 | 2-[1-(Biphenyl-4-ylcarbonyl)piperidin-4-yl]-N-methyl-1H-benzimidazole-5-carboxamide | 439 | M |
| 131 | 2-(1-{[4-(Pyridin-2-yl)phenyl]sulfonyl}piperidin-4-yl)-1H-benzimidazole | 210 [½M + H], 419 [M + H] | N |
| 132 | 2-(4-{[4-(1H-Imidazol-2-yl)piperidin-1-yl]sulfonyl}phenyl)pyridine | 185 [½M + H], 369 [M + H] | O |
| 133 | 2-(4-{[3-(1H-Imidazol-2-yl)azetidin-1-yl]sulfonyl}phenyl)pyridine | 171 [½M + H], 341 [M + H] | P |
| 134 | 2-{1-[(2'-Fluorobiphenyl-4-yl)carbonyl]piperidin-4-yl}-1H-imidazole-4-carbonitrile | 375 [M + H], 749 [2M + H] | Q |
| 135 | 2-{[1-(Biphenyl-4-ylcarbonyl)piperidin-4-yl]methyl}-1H-imidazole-4-carbonitrile | 371 [M + H], 741 [2M + H] | Q |
| 136 | 2-({1-[(2'-Fluorobiphenyl-4-yl)carbonyl]piperidin-4-yl}methyl)-1H-imidazole-4-carbonitrile | 389 [M + H], 777 [2M + H] | Q |

Assessment of Biological Properties

The biological properties of the compounds of the formula I were assessed using the assays described below.
Inhibition of 5HT2B mediated Ca2+ Flux in 5-HT$_{2B}$ Stably Transfected CHO-K Cells.
Method 1: Ca$^{2+}$ Detection Via FLIPR.

In each well of a 384 well plate are diluted 5-5HT$_{2B}$ stably transfected CHO-K cells to a final concentration of $4 \times 10^5$ cells/mL in 25 µL of UltraCho media with 0.2% Zeocin. The plate is incubated at 37° C. in a 5% CO$_2$ atmosphere overnight to yield 10,000 cells/well. Media is removed, and 25 µL of 1× Calcium 4 dye in HBSS and 2 mM probenicid are added to each well. The plate is incubated for 1 h at 37° C./5% CO$_2$. 5 µL of test compound in 0.4% DMSO in HBSS is added from a 3-fold serially diluted master plate. After incubating for 15 minutes, 10 µL of 5-HT at 4 times its EC$_{70}$ concentration in HBSS is added. Fluorescence is measured immediately on a fluorescence plate reader. Percents of control are plotted versus inhibitor concentration, and IC$_{50}$'s are determined from the inflection point.
Method 2: Ca$^{2+}$ Detection Via Chemiluminescence.

5-HT$_{2B}$ and aequorin stably transfected CHO-K cells are suspended in 1;1 DMEM/F12 and 0.1% BSA to a concentration of $5 \times 10^6$ cells/mL. Ceolenterazine is added to a final concentration of 5 µM. The mixture is incubated overnight at room temperature, and then diluted with 1:1 DMEM/F12 media to a final concentration of $6 \times 10^5$ cells/mL. Into each well of a black clear bottom 384 well plate is added 25 µL of the cell suspension (15,000 cells/well). 5 µL of test compound in 0.4% DMSO in DMEM is added from a 3-fold serially diluted master plate. After incubating for 15 minutes, 10 µL of 5-HT at 4 times its $EC_{70}$ concentration in HBSS is added. Chemiluminescence is read immediately on a Hammamatsu instrument. Percents of control are plotted versus inhibitor concentration, and $IC_{50}$'s are determined from the inflection point.

"Most preferred" examples of this invention have $IC_{50}$'s<20 nM. "Preferred" examples of this invention have $IC_{50}$'s<1000 nM.

Therapeutic Use

The compounds described herein are potent antagonists of serotonin receptor 5-HT2B. They may be used to treat diseases characterized by dysfunctional or overly active 5-HT$_{2B}$ receptors, including cardiovascular disorders such as chronic heart disease and hypertension; vascular disorders such as systemic hypertension, pulmonary hypertension, migraine, and erectile dysfunction; gastrointestinal disorders such as inflammatory bowel syndrome, and GI motility disorders; CNS disorders such as depression, anxiety, sleeping disorders, ADHD, Alzheimer's disease and Parkinson's disease; pulmonary disorders such as asthma and COPD; other disorders including prostatic hyperplasia and pain.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

The invention claimed is:
1. A compound of the formula (I)

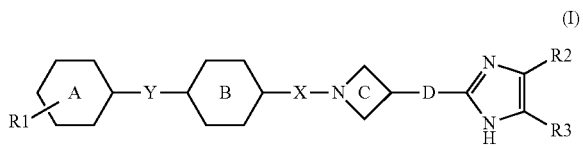

wherein:
Ring A is a 6 membered aryl optionally each substituted by one to three $R^1$;
Ring B is aryl optionally substituted by one to three $R^1$;
Ring C is piperidine ring optionally substituted with $R^4$;
Y is a bond;
X is C=O;
D is a bond;
$R^1$ is independently halogen, CN, $C_{1-6}$alkyl, $C_{3-6}$ cycloalkyl $C_{1-6}$alkoxy, $C_{1-3}$alkoxy$C_{1-3}$alkoxy, hydroxy, oxo, substituted amino, $C_{1-6}$acylamino, $C_{1-6}$ acyl, —$CO_2H$, —$CO_2(C_{1-6}$alkyl) or —$CO_2NR^7_2$;
$R^2$ and $R^3$ taken together to form a fused benzo ring further substituted with one or more $R^5$;
$R^4$ is halogen, hydroxy, $C_{1-4}$alkoxy or $C_{1-6}$alkyl;
$R^5$ is halogen, —$CO_2H$, —$CO_2(C_{1-6}$alkyl), —$CO_2NR_2$, hydroxy, $C_{1-6}$alkoxy or $C_{1-6}$alkyl, wherein 2 $R^5$'s may be taken together to form a carbocyclic, heterocylic or heteroaryl ring;
$R^6$ is hydrogen, halogen, hydroxy, $C_{1-4}$alkoxy or $C_{1-6}$alkyl wherein 2 $R^6$'s may be taken together to form a carbocyclic, heterocylic or heteroaryl ring;
$R^7$ is hydrogen or $C_{1-6}$alkyl wherein two $R^7$'s may be taken together to form a 3-7 membered heterocycle;
wherein each $R^1$-$R^6$ is optionally partially or fully halogenated where possible;
or a pharmaceutically acceptable salt thereof;
with the proviso that [4-(1H-benzimidazol-2-yl)-piperidin-1-yl]-biphenyl-4-yl-methanone is exluded.
2. The compound according to claim 1 and wherein:
Ring A is phenyl optionally substituted by one to two $R^1$;
Ring B is a phenyl optionally substituted by one $R^1$;

$R^1$ is independently halogen, $C_{1-3}$alkyl, —$OCF_3$, cyclopropyl, $C_{1-3}$alkoxy, $C_{1-3}$alkoxy$C_{1-3}$alkoxy, oxo or $C_{1-3}$acylamino;

$R^5$ is halogen, —$CO_2H$, —$CO_2(C_{1-6}$alkyl), —$CO_2NR_2$, hydroxy, $C_{1-6}$alkoxy or $C_{1-6}$alkyl;

$R^6$ is hydrogen, halogen, hydroxy, $C_{1-4}$alkoxy or $C_{1-6}$alkyl.

3. The compound according to claim 1 and wherein:

$R^1$ is independently F, Cl, $C_{1-3}$alkyl, —$OCF_3$, cyclopropyl, $C_{1-3}$alkoxy, $C_{1-3}$alkoxy$C_{1-3}$alkoxy or $C_{1-3}$acylamino;

$R^5$ is F, —$CO_2H$, —$CO_2(C_{1-6}$alkyl), —$CO_2NR_2$, hydroxy, $C_{1-6}$alkoxy or $C_{1-6}$alkyl.

4. A compound chosen from

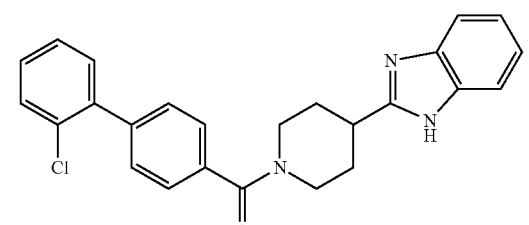

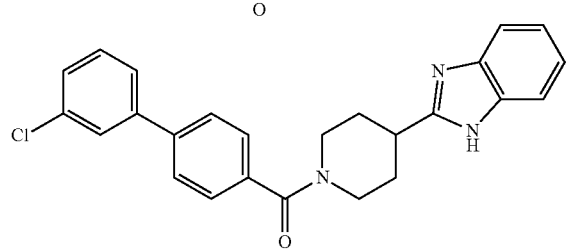

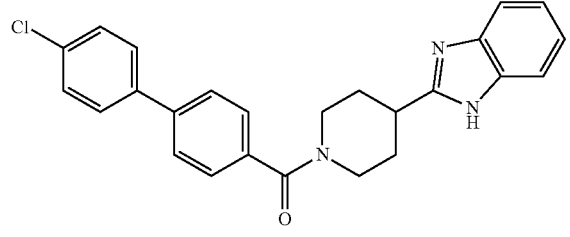

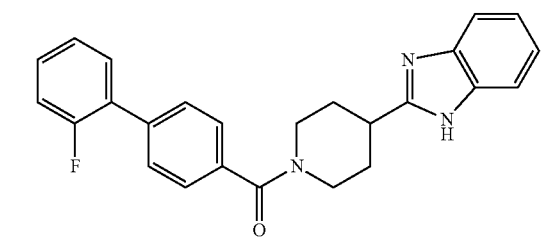

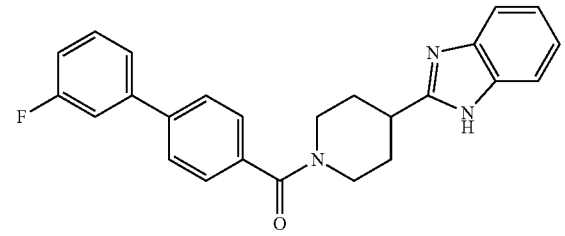

-continued

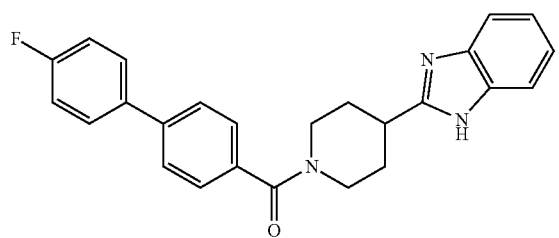

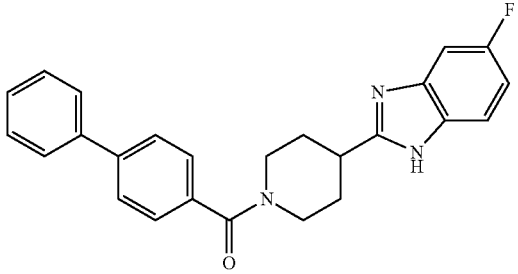

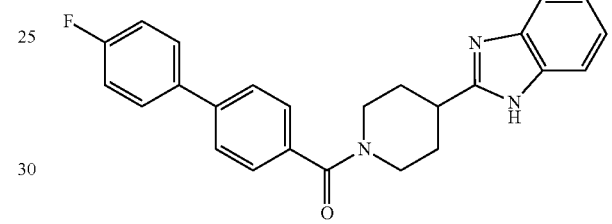

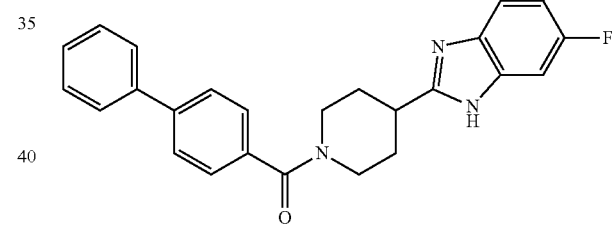

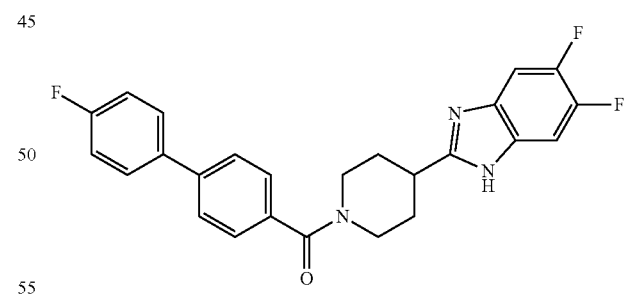

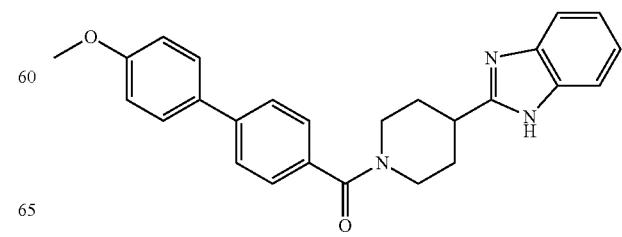

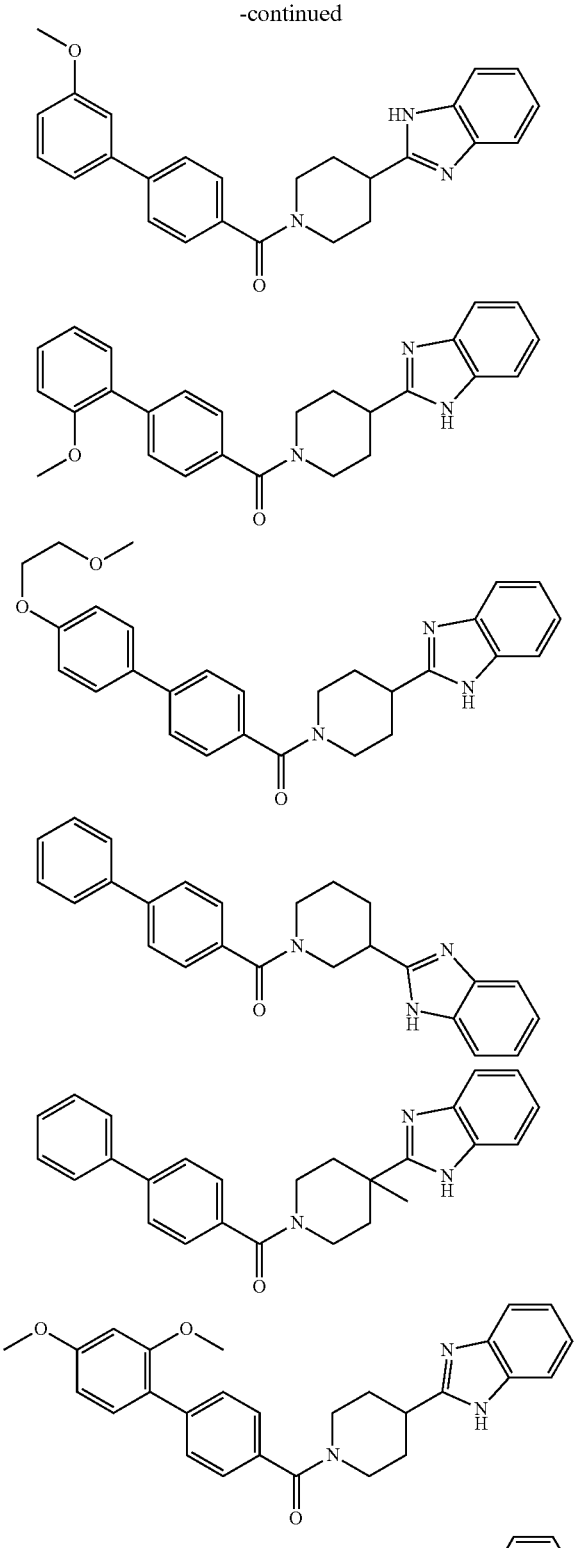
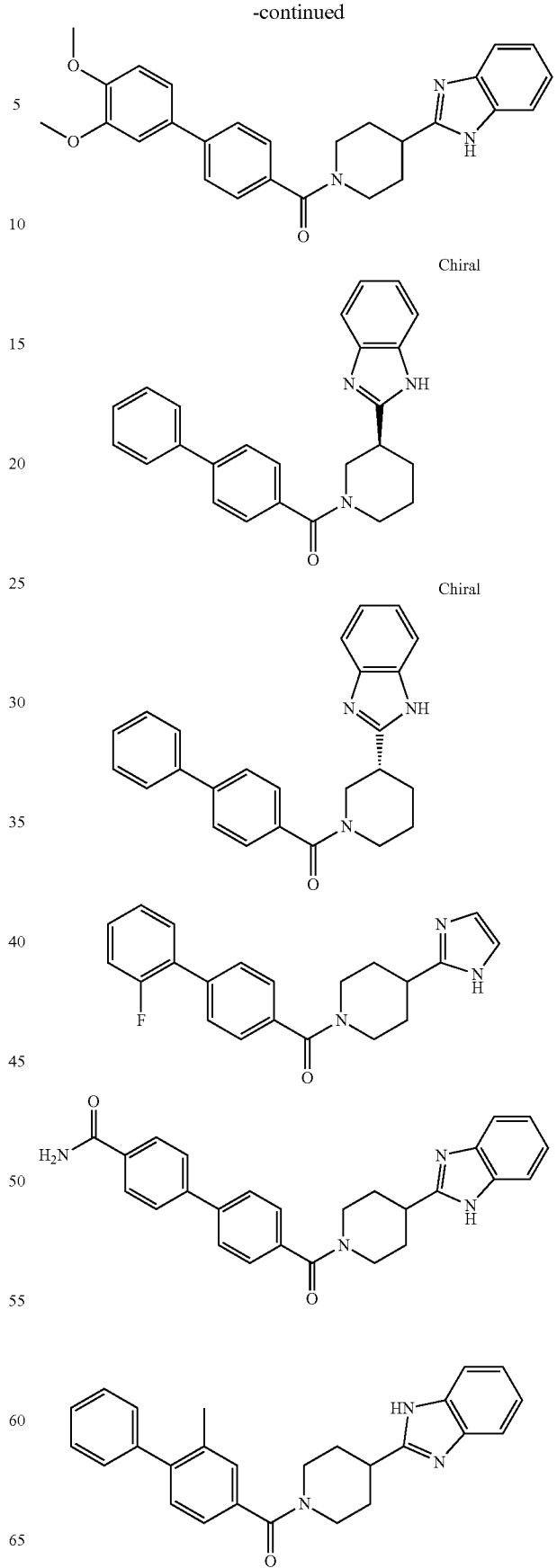

-continued
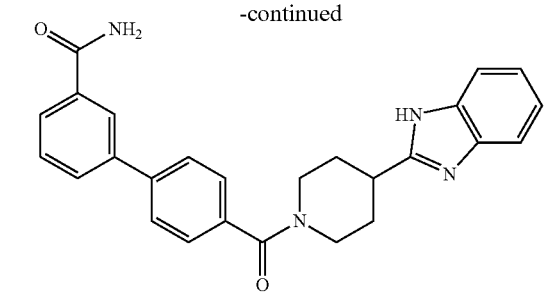
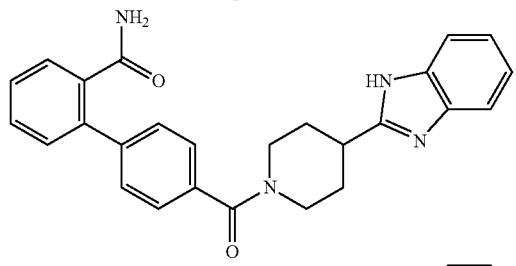
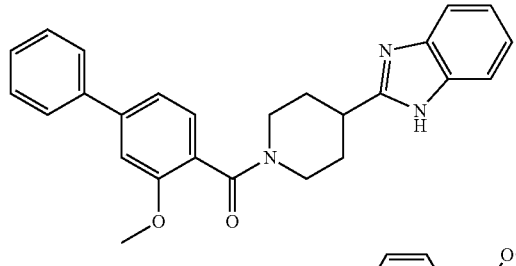
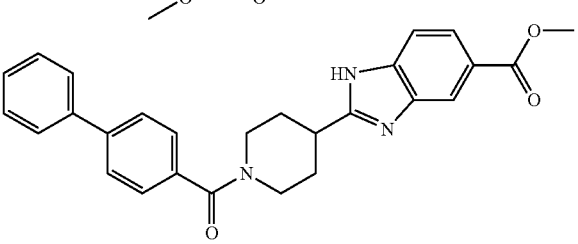
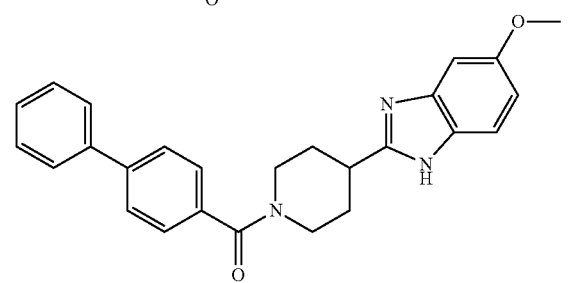
-continued
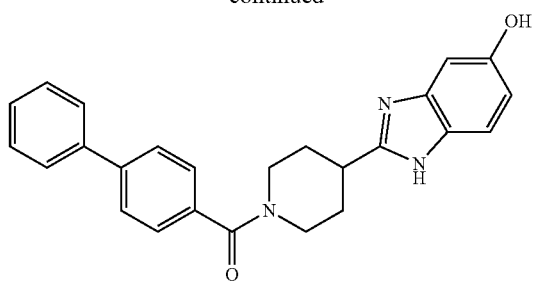
and
or a pharmaceutically acceptable salt thereof.
5. A composition comprising therapeutically effective amount of a compound according to claim 1 and one or more pharmaceutically acceptable carriers and/or adjuvants.
* * * * *

UNITED STATES PATENT AND TRADEMARK OFFICE
CERTIFICATE OF CORRECTION

PATENT NO.        : 8,609,696 B2                                    Page 1 of 1
APPLICATION NO. : 13/139363
DATED             : December 17, 2013
INVENTOR(S)       : Cogan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 151 days.

Signed and Sealed this
Twenty-second Day of September, 2015

Michelle K. Lee
*Director of the United States Patent and Trademark Office*